United States Patent [19]
Hill et al.

[11] Patent Number: 6,028,033
[45] Date of Patent: Feb. 22, 2000

[54] N-AMINOPYRIDONE DERIVATIVES AND THEIR USE AS HERBICIDES

[75] Inventors: Regina Luise Hill, Speyer; Wolfgang von Deyn, Neustadt; Uwe Kardorff, Mannheim; Stefan Engel, Idstein; Martina Otten, Ludwigshafen; Marcus Vossen, Mannheim; Ralf Klintz, Gruenstadt; Helmut Walter, Obrigheim; Ulf Misslitz, Neustadt; Karl-Otto Westphalen, Speyer, all of Germany

[73] Assignee: BASF Aktiengesellschaft, Ludwigshafen, Germany

[21] Appl. No.: 08/952,251

[22] PCT Filed: May 8, 1996

[86] PCT No.: PCT/EP96/01923

§ 371 Date: Nov. 6, 1997

§ 102(e) Date: Nov. 6, 1997

[87] PCT Pub. No.: WO96/37471

PCT Pub. Date: Nov. 28, 1996

[30] Foreign Application Priority Data

May 22, 1995 [DE] Germany ............... 195 18 739

[51] Int. Cl.[7] ............... C07D 211/98; C07D 213/89; C07C 59/48; A01N 43/40
[52] U.S. Cl. ............... 504/244; 546/283.7; 546/300; 549/323; 549/324; 549/325
[58] Field of Search ............... 546/300, 283.7; 504/244; 549/323, 324, 325

[56] References Cited

U.S. PATENT DOCUMENTS 4,152,136  5/1979  Taylor ............... 71/90
5,234,895  8/1993  Felix ............... 504/254

OTHER PUBLICATIONS

*Synthesis*, No. 10, 1974, p. 717–719.
*Pat. Abst. of Japan*, vol. 6, No. 44 (C–095), Mar. 19, 1982 (English abstract of JP 56 161348).
*Organic Synthesis, Voll. I vol II.* 1946, pp. 81–83, XP002009451.
Cignarella, *Eur. J. Med. Chem.*, 30, 9, 1995, pp. 721–726.

*Primary Examiner*—Alan L. Rotman
*Attorney, Agent, or Firm*—Keil & Weinkauf

[57] ABSTRACT

There are described N-aminopyridone derivatives of the formula I:

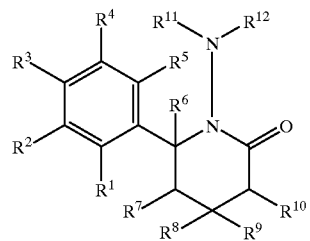

where the substituents $R^1$ to $R^{12}$ have the meanings given in claim 1, a process for their preparation, and their use for controlling undesirable vegetation.

13 Claims, No Drawings

N-AMINOPYRIDONE DERIVATIVES AND THEIR USE AS HERBICIDES

CROSS-REFERENCE

This application is a 371 of PCT/EP96/01923 filed May 8, 1996.

The present invention relates to N-aminopyridone derivatives of the formula I:

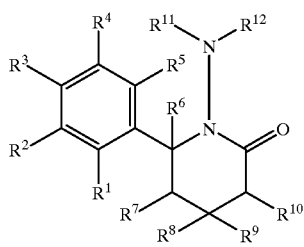

where the substituents have the following meanings:
$R^1$–$R^5$ can be identical or different substituents:
  hydrogen, OH, $NO_2$, CN, halogen, OCN, SCN, $SF_5$, $OR^{15}$, $(CH_2)_mSO_nR^{16}$, $ZCOR^{17}$, $NR^{20}SO_nR^{13}$, $OSO_nR^{13}$, $C_1$–$C_4$-alkyl, $C_1$–$C_4$-alkoxy, $C_1$–$C_4$-alkylamino, $C_1$–$C_3$-dialkylamino, $C_2$–$C_4$-alkenyl, $C_2$–$C_4$-alkynyl, it being possible for the carbon radicals to be unbranched or branched and to -have attached to them in each case one to five halogen atoms and/or one to two of the following groups: alkoxy, alkylthio, cyano, nitro;
  two adjacent radicals of $R^1$ to $R^5$ are part of a cyclic acetal having five ring members, it being possible for the ring carbon atom to be substituted by one to two halogen atoms;
Z is —O—, —$NR^{20}$—, a bond;
$R^6$ and $R^7$ are in each case hydrogen or together form a bond;
$R^9$ and $R^{10}$ are in each case hydrogen or together form a bond;
$R^8$ is hydrogen, $C_3$–$C_6$-cycloalkyl, $ZCOR^{17}$, $C_1$–$C_4$-alkyl, $C_1$–$C_4$-alkoxyalkyl, $C_1$–$C_4$-haloalkyl;
$R^{11}$ is hydrogen, $C_1$–$C_4$-alkyl, $C_3$–$C_6$-cycloalkyl, $(CH_2)_mSO_nR^{16}$, $C_2$–$C_4$-alkynyl, $C_2$–$C_4$-alkenyl, it being possible for the carbon radicals to be unbranched or branched and to have attached to them in each case one to five halogen atoms and/or one to two of the following groups: alkoxy, alkylthio, nitro, cyano;
  phenylsulfonyl, phenylsulfinyl which is unsubstituted or can have attached to it one to three of the following radicals: halogen, nitro, cyano, unbranched or branched $C_1$–$C_3$-alkyl, $C_1$–$C_3$-alkoxyalkyl or $C_1$–$C_3$-haloalkyl, OCN, SCN;
phenyl which is unsubstituted or can have attached to it one to five of the following substituents: halogen, nitro, cyano, unbranched or branched: $C_1$–$C_4$-alkyl, $C_1$–$C_4$-alkoxy, $C_1$–$C_4$-alkoxyalkyl, $C_1$–$C_4$-haloalkyl, $C_1$–$C_4$-alkylamino, $C_1$–$C_4$-dialkylamino, $C_1$–$C_4$-alkylcarbonyloxyalkyl, OCN, $SF_5$, SCN, $(CH_2)_mSO_nR^{16}$, $NSO_nR^{13}$, $OSO_nR^{13}$, $ZCOR^{17}$;

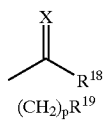

a 5-membered saturated, unsaturated or aromatic heterocycle having one to four nitrogen atoms or one to three nitrogen atoms and additionally one sulfur or oxygen atom in the ring, which can have attached to it one to three halogen atoms and/or one to three of the following radicals: nitro, cyano, alkyl, alkoxy, alkylthio, haloalkyl, haloalkoxy, $ZCOR^{17}$;
  a thienyl- or furyl radical which can have attached to it one to three halogen atoms and/or one to three of the following radicals: nitro, cyano, alkyl, alkoxy, alkylthio, haloalkyl, haloalkoxy, $ZCOR^{17}$;
  a 6-membered saturated, unsaturated or aromatic heterocycle having one to four nitrogen atoms or one to three nitrogen atoms and additionally one sulfur or oxygen atom in the ring, which can have attached to it one to three halogen atoms and/or one to three of the following radicals: nitro, cyano, alkyl, alkoxy, alkylthio, haloalkyl, haloalkoxy, $ZCOR^{17}$;
  $(CH_2)_pCHR^{21}R^{22}$;
$R^{12}$ is hydrogen, $C_1$–$C_4$-alkyl, $C_3$–$C_6$-cycloalkyl.
$R^{11}$ and $R^{12}$ together form a double bond which can be substituted by two identical or different substituents $R^{14}$;
$R^{11}$ and $R^{12}$ together form a double bond which can be substituted by the radicals $R^{23}$ and $R^{24}$;
$R^{11}$ and $R^{12}$ together with the adjacent N atom form a nitro group; $R^{11}$ and $R^{12}$ are part of a 5- or 6-membered saturated, unsaturated or aromatic heterocycle which is bonded via nitrogen and has one to four nitrogen atoms or one to three nitrogen atoms and additionally one sulfur or oxygen atom in the ring, which has attached to it one to three halogen atoms and/or one to three of the following radicals: oxo, nitro, cyano, alkyl, alkoxy, alkylthio, haloalkyl, haloalkoxy;
X is O, S, $NR^{20}$,
$R^{13}$ is $C_1$–$C_4$-alkyl, $C_3$–$C_6$-cycloalkyl, it being possible for the carbon radicals to be unbranched or branched and to have attached to them in each case one to five halogen atoms and/or one to two of the following groups: alkoxy, alkylthio, cyano, nitro;
$R^{14}$ is hydrogen, $C_1$–$C_6$-alkyl, $C_3$–$C_6$-cycloalkyl, $C_2$–$C_6$-alkynyl, $C_2$–$C_6$-alkenyl, it being possible for the carbon radicals to be unbranched or branched and to have attached to them in each case one to five halogen atoms and/or one to two of the following groups: OH, $C_1$–$C_4$-alkoxy, $C_1$–$C_4$-alkoxyalkyl, alkylthio, cyano, substituted or unsubstituted phenyl, nitro, $ZCOR^{17}$;
  phenyl which is unsubstituted or can have attached to it one to five of the following substituents: halogen, nitro, cyano, $C_1$–$C_4$-alkyl, $C_1$–$C_4$-alkoxy, $C_1$–$C_4$-haloalkyl, $C_1$–$C_4$-alkoxyalkyl, $C_1$–$C_4$-alkylamino, $C_1$–$C_4$-dialkylamino, it being possible for the alkyl radicals to be unbranched or branched, OCN, SCN, OH, $(CH_2)_mSO_nR^{16}$, $NSO_nR^{13}$, $OSO_nR^{13}$, $ZCOR^{17}$, $SF_5$;
  a 5-membered saturated, unsaturated or aromatic heterocycle having one to four nitrogen atoms or one to three nitrogen atoms and additionally one sulfur or oxygen atom in the ring, which can have attached to it one to three halogen atoms and/or one to three of the following radicals: nitro, cyano, alkyl, alkoxy, alkylthio, haloalkyl, haloalkoxy, $ZCOR^{17}$;
  a thienyl or furyl radical which can have attached to it one to three halogen atoms and/or one to three of the following radicals: nitro, cyano, alkyl, alkoxy, alkylthio, haloalkyl, haloalkoxy, $ZCOR^{17}$;
  a 6-membered saturated, unsaturated or aromatic heterocycle having one to four nitrogen atoms in the ring which can have attached to it one to three halogen atoms and/or one to three of the following radicals: nitro, cyano, alkyl, alkoxy, alkylthio, haloalkyl, haloalkoxy, $ZCOR^{17}$;
$R^{15}$ is hydrogen, $C_1$–$C_4$-alkyl, $C_1$–$C_4$-alkylcarbonyl, $C_1$–$C_4$-alkoxycarbonyl, $C_1$–$C_4$-alkylaminocarbonyl, it being possible for the carbon radicals to be unbranched or branched and to have attached to them in each case one to five halogen atoms and/or one to two of the following groups: cyano, nitro;

$R^{16}$ is hydroxyl, amino, $C_1$–$C_4$-alkyl, $C_1$–$C_4$-alkoxy, $C_1$–$C_4$-alkylamino, $C_1$–$C_4$-dialkylamino, it being possible for the carbon radicals to be unbranched or branched and to have attached to them in each case one to five halogen atoms and/or one to two of the following groups: cyano, nitro;

$R^{17}$ is hydrogen, amino, hydroxyl, $C_1$–$C_4$-alkoxy, $C_1$–$C_4$-alkyl, $C_1$–$C_4$-alkylamino, $C_1$–$C_4$-dialkylamino, it being possible for the carbon radicals to be unbranched or branched and to have attached to them in each case one to five halogen atoms and/or one to two of the following groups: alkoxy, alkylthio, cyano, nitro;

- phenyl which is unsubstituted or can have attached to it one to five of the following substituents: halogen, nitro, cyano, $C_1$–$C_4$-alkyl, $C_1$–$C_4$-alkoxy, $C_1$–$C_4$-haloalkyl, $C_1$–$C_4$-alkoxyalkyl, $C_1$–$C_4$-alkylamino, $C_1$–$C_4$-dialkylamino, it being possible for the alkyl radicals to be unbranched or branched, OCN, SCN, OH, $ZCOR^{17}$;
- phenoxy which can have attached to it one to five of the following substituents: halogen, nitro, cyano, $C_1$–$C_4$-alkyl, $C_1$–$C_4$-alkoxy, $C_1$–$C_4$-haloalkyl, $C_1$–$C_4$-alkoxyalkyl, $C_1$–$C_4$-alkylamino, $C_1$–$C_4$-dialkylamino, it being possible for the alkyl radicals to be unbranched or branched, OCN, SCN, OH, $ZCOR^{17}$, $SF_5$;

$R^{18}$ is hydrogen, $C_1$–$C_6$-alkyl, $C_3$–$C_6$-cycloalkyl, $C_1$–$C_6$-alkoxy, $C_2$–$C_6$-alkynyl, $C_2$–$C_6$-alkenyl, $C_1$–$C_6$-alkylamino, $C_1$–$C_6$-dialkylamino, it being possible for the carbon radicals to be unbranched or branched and to have attached to them in each case one to five halogen atoms and/or one to two of the following groups: $C_1$–$C_4$-alkoxy, alkylthio, cyano, nitro, $C_1$–$C_4$-alkylamino, OCN, SCN, OH, $(CH_2)_m SO_n R^{16}$, $NSO_n R^{13}$, $OSO_n R^{13}$, $ZCOR^{17}$;

- phenyl which is unsubstituted or can have attached to it one to five of the following substituents: halogen, nitro, cyano, $C_1$–$C_4$-alkyl, $C_1$–$C_4$-alkoxy, $C_1$–$C_4$-haloalkyl, $C_1$–$C_4$-alkoxyalkyl, $C_1$–$C_4$-alkoxyalkyloxy, $C_1$–$C_4$-alkylamino, $C_1$–$C_4$-dialkylamino, it being possible for the alkyl radicals to be unbranched or branched, OCN, SCN, OH, $(CH_2)_m SO_n R^{16}$, $NSO_n R^{13}$, $OSO_n R^{13}$, $ZCOR^{17}$, $SF_5$;
- phenoxy which can have attached to it one to five of the following substituents: halogen, nitro, cyano, $C_1$–$C_4$-alkyl, $C_1$–$C_4$-alkoxy, $C_1$–$C_4$-haloalkyl, $C_1$–$C_4$-alkoxyalkyl, $C_1$–$C_4$-alkylamino, $C_1$–$C_4$-dialkylamino, it being possible for the alkyl radicals to be unbranched or branched, OCN, SCN, OH, $(CH_2)_m SO_n R^{16}$, $NSO_n R^{13}$, $OSO_n R^{13}$, $ZCOR^{17}$, $SF_5$;
- a 5-membered saturated, unsaturated or aromatic heterocycle having one to four nitrogen atoms or one to three nitrogen atoms and additionally one sulfur or oxygen atom in the ring, which can have attached to it one to three halogen atoms and/or one to three of the following radicals: nitro, cyano, alkyl, alkoxy, alkylthio, haloalkyl, haloalkoxy, $ZCOR^{17}$;
- a thienyl or furyl radical which can have attached to it one to three halogen atoms and/or one to three of the following radicals: nitro, cyano, alkyl, alkoxy, alkylthio, haloalkyl, haloalkoxy, $ZCOR^{17}$;
- a 6-membered saturated, unsaturated or aromatic heterocycle having one to four nitrogen atoms in the ring which can have attached to it one to three halogen atoms and/or one to three of the following radicals: nitro, cyano, alkyl, alkoxy, alkylthio, haloalkyl, haloalkoxy, $ZCOR^{17}$;

$R^{19}$ is $C_1$–$C_4$-alkylamino, $C_1$–$C_4$-dialkylamino, $(CH_2)_m SO_n R^{16}$, $NSO_n R^{13}$, $OSO_n R^{13}$, $ZCOR^{17}$, $C_3$–$C_6$-cycloalkyl which can be substituted by one to four halogen atoms or $C_1$–$C_4$-alkoxy;

- phenyl which is unsubstituted or can have attached to it one to five of the following substituents: halogen, nitro, cyano, $C_1$–$C_4$-alkyl, $C_1$–$C_4$-alkoxy, $C_1$–$C_4$-haloalkyl, $C_1$–$C_4$-alkoxyalkyl, $C_1$–$C_4$-alkoxyalkyloxy, $C_1$–$C_4$-alkylamino, $C_1$–$C_4$-dialkylamino, it being possible for the carbon radicals to be unbranched or branched, OCN, SCN, OH, $(CH_2)_m SO_n R^{16}$, $NSO_n R^{13}$, $OSO_n R^{13}$, $ZCOR^{17}$, $SF_5$;
- phenyl which has attached to it a fused five- or six-membered ring with or without one to two hetero atoms such as nitrogen, sulfur or oxygen and whose carbon atoms can be unsubstituted or substituted by halogen;
- phenoxy which can have attached to it one to five of the following substituents: halogen, nitro, cyano, $C_1$–$C_4$-alkyl, $C_1$–$C_4$-alkoxy, $C_1$–$C_4$-haloalkyl, $C_1$–$C_4$-alkoxyalkyl, $C_1$–$C_4$-alkoxyalkyloxy, $C_1$–$C_4$-alkylamino, $C_1$–$C_4$-dialkylamino, it being possible for the alkyl radicals to be unbranched or branched, OCN, SCN, OH, $(CH_2)_m SO_n R^{16}$, $NSO_n R^{13}$, $OSO_n R^{13}$, $ZCOR^{17}$, $SF_5$;
- a 5-membered saturated, unsaturated or aromatic heterocycle having one to four nitrogen atoms or one to three nitrogen atoms and additionally one sulfur or oxygen atom in the ring, which can have attached to it one to three halogen atoms and/or one to three of the following radicals: nitro, cyano, alkyl, alkoxy, alkylthio, haloalkyl, haloalkoxy;
- a thienyl or furyl radical which can have attached to it one to three halogen atoms and/or one to three of the following radicals: nitro, cyano, alkyl, alkoxy, alkylthio, haloalkyl, haloalkoxy;

$R^{20}$ is hydrogen, $C_1$–$C_4$-alkyl, $C_3$–$C_6$-cycloalkyl, it being possible for the carbon radicals to be unbranched or branched and to have attached to them in each case one to five halogen atoms and/or one to two of the following groups: alkoxy, cyano, nitro;

$R^{21}$ and $R^{22}$ are part of a cyclic acetal or thioacetal having five or six ring members;

$C_1$–$C_4$-alkoxy which can be unsubstituted or can have attached to it one to five of the following radicals: cyano, nitro, halogen;

$R^{23}$ and $R^{24}$ are part of a cyclic system having five to six ring members which can be unsubstsituted or can have attached to it one to five of the following radicals: $NO_2$, CN, halogen, OCN, SCN, OH, $(CH_2)_m SO_n R^{16}$, $ZCOR^{17}$, $NSO_n R^{13}$, $OSO_n R^{13}$, $C_1$–$C_4$-alkyl, $C_1$–$C_4$-alkoxy, $C_1$–$C_4$-alkoxyalkyloxy, $C_1$–$C_4$-alkylamino, $C_1$–$C_4$-dialkylamino, $C_2$–$C_4$-alkenyl, $C_2$–$C_4$-alkynyl, it being possible for the alkyl radicals to be unbranched or branched and to have attached to them in each case one to five halogen atoms and/or one to two of the following groups: alkoxy, alkylthio, cyano, alkylcarbonyl, alkoxycarbonyl, alkylamino, dialkylamino;

m=0–4 n=0–2 p=1–4, to a process for their preparation, and to their use for controlling undesirable vegetation.

The literature, such as, for example, U.S. Pat. No. 5,234,895, discloses herbicidally active N-alkyl-substituted 6-aryl-α-pyridones.

The herbicidal properties of the known compounds and their tolerance by crop plants are, however, only moderately satisfactory.

It was an object of the present invention to find novel N-substituted arylpyridones having improved properties and also a process for their preparation.

We have found that this object is achieved with the N-aminopyridone derivatives of the general formula I mentioned at the outset.

Compounds of the formula I are accessible by reducing compounds of the formula Ia with Raney Nickel in ethanol:

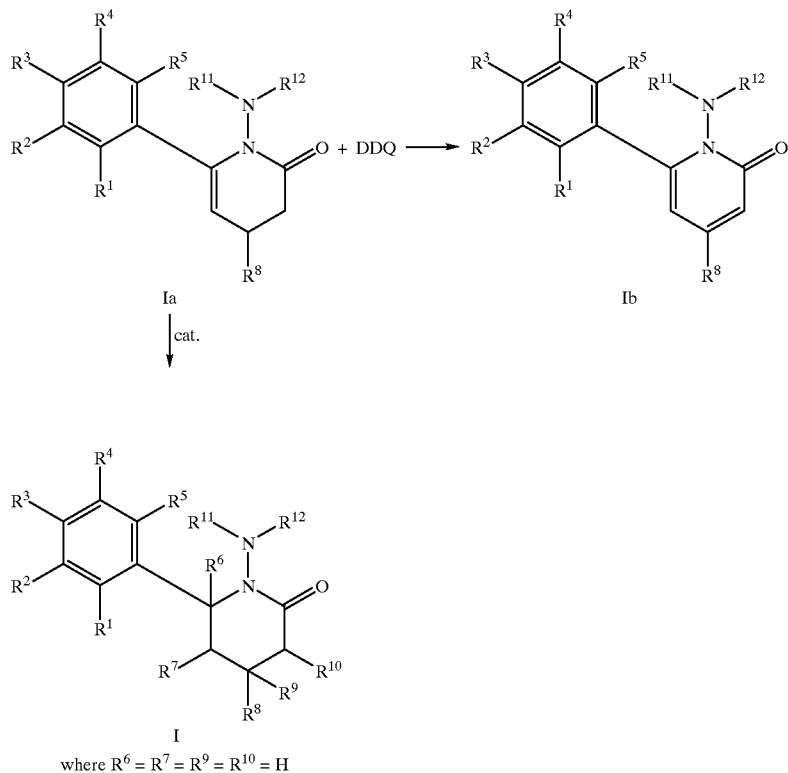

The novel compounds of the formula Ib are obtained, for example, by dehydrogenating compounds of the formula Ia using DDQ (2,3-dichloro-3,4-dicyanoquinone). In the abovementioned formulae, the substituents $R^1$–$R^5$ and also $R^8$ and $R^{11}$ and $R^{12}$ have the meanings given at the outset. The reaction is carried out by adding a 10-fold excess of DDQ to a solution of the N-amino-substituted dihydropyridone Ia. Solvents which may be used are toluene, acetonitrile and/or xylenes. The reaction solution is stirred at from 50–150° C., in particular at 110° C., until the reaction has ended. The product is worked up by filtration through Alox n III.

The novel compounds of the formula Ia are obtained by reacting 6-aryl-2H-dihydro-α-pyrones of the general formula II with hydrazine/hydrazide hydrochlorides.

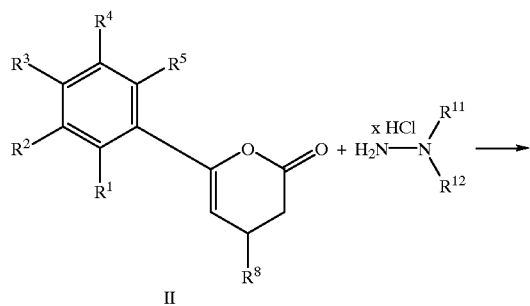

-continued

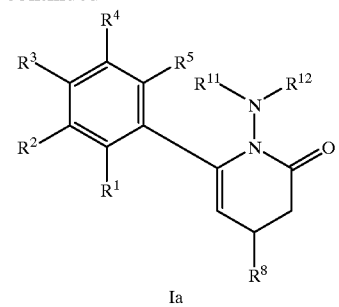

In the abovementioned formulae, the substituents $R^1$–$R^5$, $R^8$ and $R^{11}$–$R^{12}$ have the meanings given-at the outset. The reaction is effected by adding a hydrazine/hydrazide to a solution of a dihydropyrone II in the presence of an auxiliary base. To react the dihydropyrone II completely, it is expedient to add at least a two-fold excess of hydrazide/hydrazine and an excess of auxiliary base. Suitable auxiliary bases are tertiary alkylamines or pyridine. Solvents which can be used are methylene chloride, dichloroethane or diethyl ether. After the reaction solution has been stirred overnight, it is worked up by extraction by shaking with aqueous HCl and aqueous $NaHCO_3$ solution. The residue obtained after the solvent has been evaporated is taken up in toluene, catalytic amounts of PTSA (p-toluenesulfonic acid) are added, and the mixture is refluxed on a water separator.

After the reaction is complete, the reaction solution is worked up by partitioning between ether and dilute NaHCO$_3$ solution.

The access to 6-aryl-3,4-2H-dihydro-α-pyrones of the structure IIa where R$^8$=methyl is known from the literature. For example, this can be achieved by cyclizing 5-aryl-5-oxopentanoic acids IIIa (R$^8$=CH$_3$) which, in turn, are obtained by processes known from the literature, either from substituted benzaldehydes V via the compound IVa (R$^8$=CH$_3$; cf. U.S. Pat. No. 5,234,895) (see route 1, diagram 1), or by a Michael addition reaction of substituted acetophenones VII with crotonic esters IX (see route 4, diagram 1).

6-Aryl-3,4-2H-dihydro-α-pyrones of the structure IIb where R$^8$=CF$_3$ are obtained by cyclizing compounds of the structure IIIb, which, in turn, are accessible by a Michael addition reaction of malonic ester and 1-aryl-4,4,4-trifluoro-2-buten-1-one IVb. The latter compound is synthesized by subjecting trifluoromethyliminium salt VI and aryl methyl ketone VII to a condensation reaction (cf. Tetrahedron Lett., 1993, 34, 5711–5714) (see route 2, diagram 1).

6-Aryl-3,4-2H-dihydro-α-pyrones of the structure IIc with the cyclopropyl ring in the 4-position (R$^8$=cyclo-C$_3$H$_5$) are accessible from 1-aryl-3-cyclopropyl-α-propen-1-one IVc, which, in turn, can be synthesized by a Knoevenagel reaction of cyclopropanecarbaldehyde VIII with arylmethyl ketone VII (cf. J. Am. Chem. Soc., 1951, 73, 3831–3837) (see route 3, diagram 1).

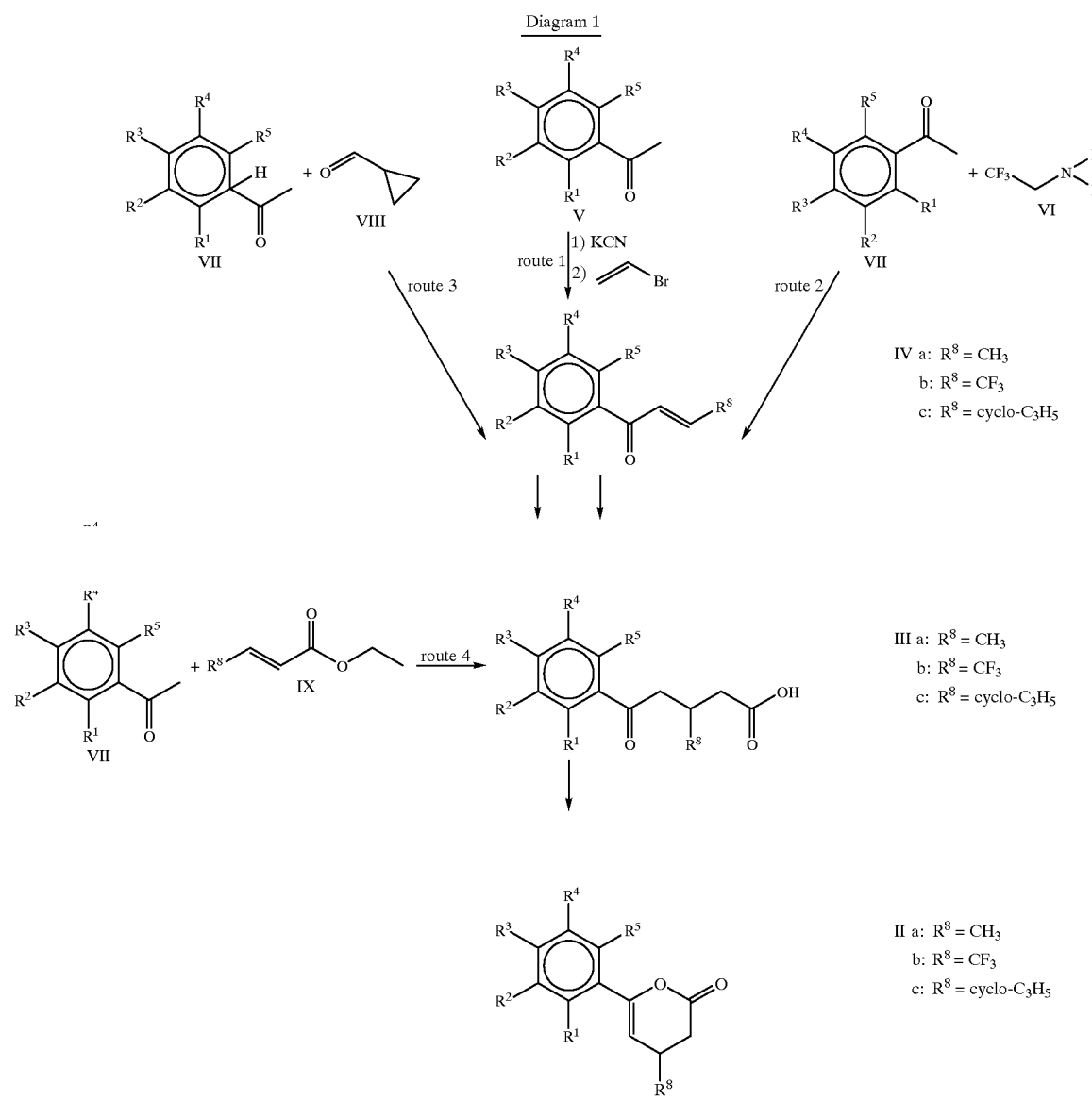

Diagram 1

Other ways of obtaining access to 6-aryl-3,4-2H-dihydropyrones of the general structure II are shown in diagram 2. The reaction of ketene acetals X with aryl vinyl ketones IV results in compounds of the structure II (diagram 2, route 1). These are also accessible by reacting metallated aromatics XI with 3-substituted glutaric anhydrides XII. The 5-keto-5-arylcarboxylic acids of the structure III which are first obtained can be subjected to cyclocondensation by the above-described methods to give 6-aryl-3,4-2H-dihydropyrans II (diagram 2, route 2).

Diagram 2

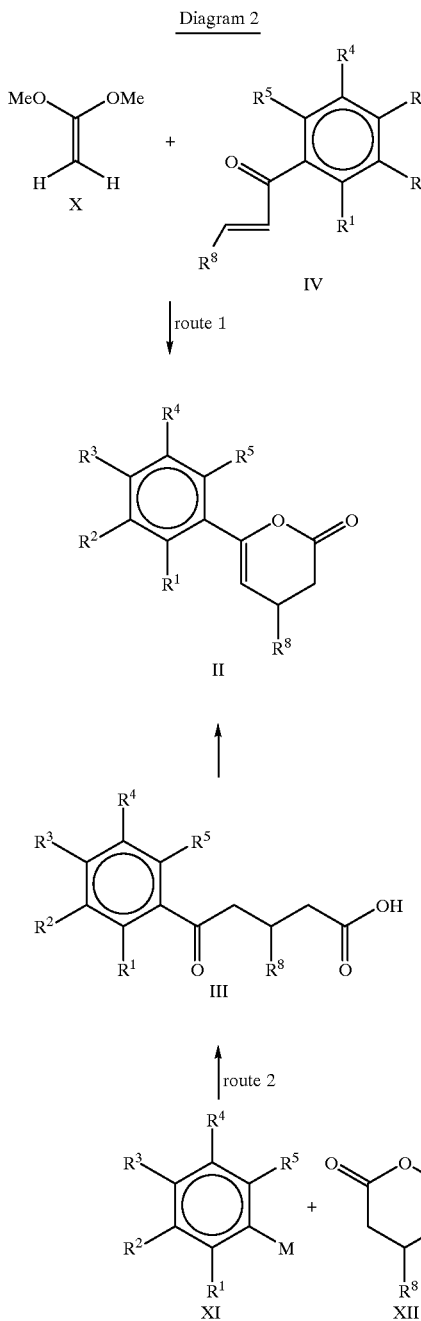

Other ways of gaining access to compounds of the formula Ib are possible via the corresponding 6-aryl-α-pyrones of the structure IIa.

For example, the reaction of an a-pyrone of the formula IIa with hydrazine hydrochloride, of the formula XIII, results in N-amino-substituted pyridones of the formula Ic (cf. J. Chem. Soc. Perkin Trans., 1979, Part 1, 8, 1957–1960).

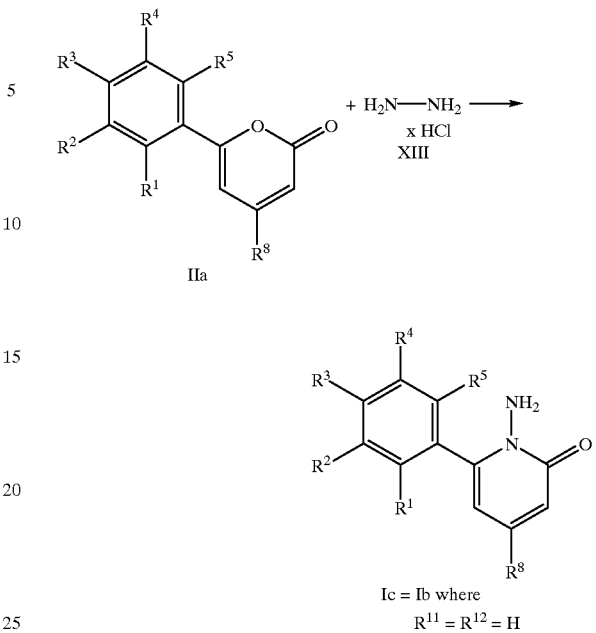

Using protocols known from the literature, these N-amino-α-pyridones of the structure Ic can then be, for example, N-acylated ($R^{11}$=H, $R^{12}$=$COR^{18}$, see route 1, diagram 3), N-alkylated ($R^{11}$=$C_1$–$C_4$-alkyl, $R^{12}$=H, see route 2, diagram 3) (Perkin Trans., 1982, N 2, 351–355; Synthesis, 1983, 1, 49–50) or converted to the N-alkenylidene compound (see route 3, diagram 3) (cf. J. Chem. Soc. Perkin Trans., 1979, Part 1, 8, 1957–1960).

Those 6-aryl-α-pyrones of the structure IIa which are used as starting compounds and which are not already known can be obtained readily by known synthesis methods. For example, 5-aryl-α-pyrones IIb ($R^8$=H) are accessible from dichlorobutadienearyl ketones (Bull. Soc. Chim. Fr., 1960, 23–28) which, in turn, can be obtained from phenyl methyl ketones and 3,3-dichloroacrolein (Bull. Soc. Chim. Fr., 1960, 23–28, see route 1, diagram 4).

A further possibility of synthesizing 6-aryl-α-pyrones of the structure IIb is to subject aryl vinyl ketones and chloroketene dimethyl acetal to a condensation reaction, followed by dehydrohalogenation hydrolysis (cf. J. Chem. Soc. Chem. Commun. 1972, 863–864; Can. J. Chem., 1975, 53, 195–200, see route 2, diagram 4).

6-Aryl-α-pyrones of the structure IIa are furthermore accessible by acid-induced cyclization of 5-aryl-3-hydroxypent-4-ynoic esters, which, in turn, are obtained by subjecting arylacetylene methyl ketones and α-bromocarboxylic esters to a Reformatzki reaction (cf. Arch. Pharm. 1961, 294, 234–239, see route 3, diagram 4).

A further example of synthesizing 6-aryl-α-pyrones of the structure IIc which may be mentioned is the cyclocondensation of α,β-unsaturated δ-keto esters, which, in turn, can be synthesized by reacting α-silyl-β,γ-unsaturated esters with arylcarbonyl chlorides (cf. J. Org. Chem, 1983, 48, 5288–5302, see route 4, diagram 4).

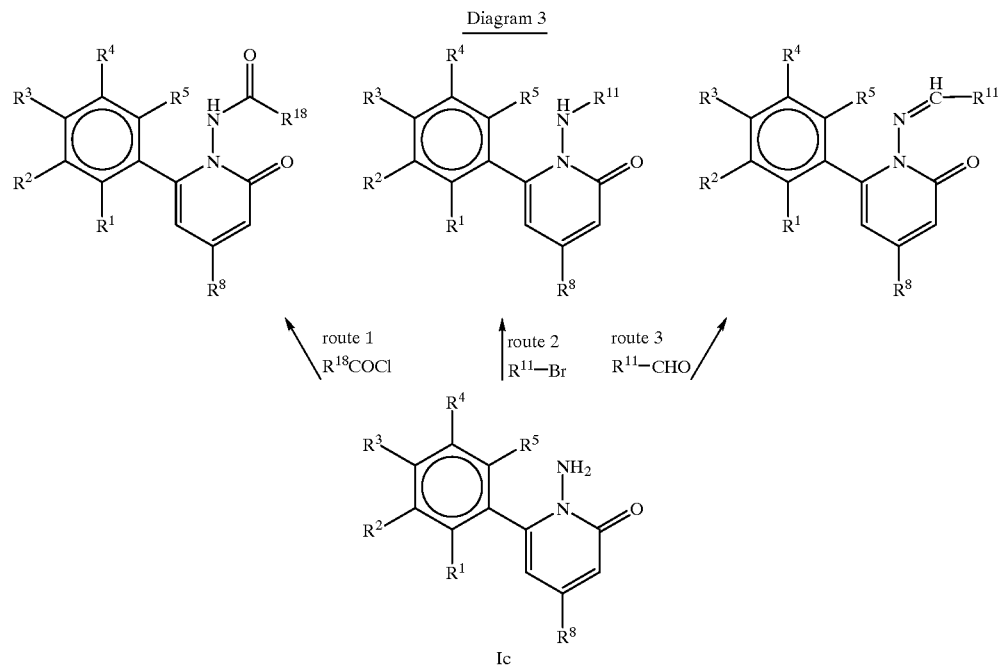

With a view to the intended use of the N-aminopyridone derivatives of the general formula I, the following radicals are suitable:

$R^1$ can be:

halogen, such as fluorine, bromine, chlorine, iodine, particularly preferably fluorine and chlorine;

$C_1$–$C_4$-alkyl, such as methyl, ethyl, propyl, 1-methylethyl, butyl, 1-methylpropyl, 2-methylpropyl, 1,1-dimethylethyl;

in particular methyl, ethyl, 1-methylethyl;

partially or fully halogenated $C_1$–$C_4$-alkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl;

$C_1$–$C_4$-alkoxy-$C_1$–$C_4$-alkyl, such as methoxymethyl, ethoxymethyl, n-propyloxymethyl, (1-methylethoxy)methyl, n-butoxymethyl, (1-methylpropoxy)methyl, (2-methylpropoxy)methyl, (1,1-dimethylethoxy)methyl, methoxyethyl, ethoxyethyl, n-propoxyethyl, (1-methylethoxy)ethyl, n-butoxyethyl, (1-methylpropoxy)ethyl, (2-methylpropoxy)ethyl, (1,1-dimethylethoxy)ethyl, 3-(methoxy)propyl, 2-(methoxy)propyl and 2-(ethoxy)propyl;

preferably $C_1$–$C_4$-alkoxy-$C_1$–$C_2$-alkyl, such as methoxymethyl, ethoxymethyl, 2-methoxyethyl and 2-ethoxyethyl;

N-$C_1$–$C_4$-alkylamino, such as N-methylamino, N-ethylamino, N-propylamino, N-1-methylethylamino, N-butylamino, N-1-methylpropylamino, N-2-methylpropylamino, N-1,1-dimethylethylamino;

in particular N-methylamino, N-ethylamino, N-1-methylethylamino;

N,N-$C_1$–$C_4$-dialkylamino, such as N,N-dimethylamino, N-ethyl-N-methylamino, N,N-diethylamino; in particular N,N-dimethylamino;

$C_2$–$C_4$-alkenyl, such as ethenyl, 1-propenyl, 2-propenyl, 1-butenyl, 2-butenyl, 3-butenyl, 1-methyl-1-ethenyl, 1-methyl-1-propenyl, 2-methyl-1-propenyl, 1-methyl-2-propenyl, 2-methyl-2-propenyl, in particular ethenyl, 1-propenyl;

$C_2$–$C_4$-alkynyl, such as propargyl, 1-butynyl, 2-butynyl, 3-butynyl;

in particular propargyl;

The above-defined group $(CH_2)_m SO_n R^{16}$ is, for example, sulfonyl, sulfonamide, $C_1$–$C_4$-alkylthio, such as methylthio, ethylthio, n-propylthio, 1-methylethylthio, n-butylthio, 1-methylpropylthio, 2-methylpropylthio and 1,1-dimethylethylthio, in particular methylthio;

$C_1$–$C_4$-alkylthioethyl, such as methylthioethyl, ethylpropylthioethyl, n-propylthioethyl, 1-methylethylthioethyl, n-butylthioethyl, 1-methylpropylthioethyl, 2-methylpropylthioethyl and 1,1-dimethylthioethyl, in particular methylthioethyl;

$C_1$–$C_4$-alkylthiomethyl, such as methylthiomethyl, ethylthiomethyl, n-propylthiomethyl, 1-methylethylthiomethyl, n-butylthiomethyl, 1-methylpropylthiomethyl, 2-methylpropylthiomethyl and 1,1-dimethylethylthiomethyl, in particular methylthiomethyl;

$C_1$–$C_4$-haloalkylthio, such as chloromethylthio, dichloromethylthio, trichloromethylthio, fluoromethylthio, difluoromethylthio, trifluoromethylthio, chlorofluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, in particular trifluoromethylthio;

$C_1$–$C_4$-haloalkylthiomethyl, such as chloromethylthiomethyl, dichloromethylthiomethyl, trichloromethylthiomethyl, fluoromethylthiomethyl, difluoromethylthiomethyl, trifluoromethylthiomethyl, chlorofluoromethylthiomethyl, chlorodifluoromethylthiomethyl, 1-fluoroethylthiomethyl, 2-fluoroethylthiomethyl, 2,2-difluoroethylthiomethyl, 2,2,2-trifluoroethylthiomethyl, 2-chloro-2,2-difluoroethylthiomethyl, 2,2-dichloro-2-fluoroethylthiomethyl, 2,2,2-trichloroethylthiomethyl and pentafluoroethylthiomethyl, in particular trifluoromethylthiomethyl;

$C_1$–$C_4$-haloalkylthioethyl, such as chloromethylthioethyl, dichloromethylthioethyl, trichloromethylthioethyl, fluoromethylthioethyl, difluoromethylthioethyl, trifluoromethylthioethyl, chlorofluoromethylthioethyl, chlorodifluoromethylthioethyl, 1-fluoroethylthioethyl, 2-fluoroethylthioethyl, 2,2-difluoroethylthioethyl, 2,2,2-trifluoroethylthioethyl, 2-chloro-2,2-difluoroethylthioethyl, 2,2-dichloro-2-fluoroethylthioethyl, 2,2,2-trichloroethylthioethyl and pentafluoroethylthioethyl, in particular trifluoromethylthioethyl;

hydroxysulfonyl-$C_1$–$C_4$-alkyl, such as hydroxysulfonylmethyl, hydroxysulfonylethyl, hydroxysulfonylpropyl, hydroxysulfonylbutyl, in particular hydroxysulfonylmethyl;

$C_1$–$C_4$-alkylsulfinyl, such as methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl, in particular methylsulfinyl;

$C_1$–$C_4$-alkylsulfonyl, such as methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, in particular methylsulfonyl;

$C_1$–$C_4$-alkoxysulfonyl, such as methoxysulfonyl, ethoxysulfonyl, n-propoxysulfonyl, 1-methylethoxysulfonyl, n-butoxysulfonyl, 1-methylpropoxysulfonyl, 2-methylpropoxysulfonyl and 1,1-dimethylethoxysulfonyl, in particular methoxysulfonyl;

N-$C_1$–$C_4$-alkylsulfamoyl, such as N-methylsulfamoyl, N-ethylsulfamoyl, N-n-propylsulfamoyl, N-1-methylethylsulfamoyl, N-n-butylsulfamoyl, N-1-methylpropylsulfamoyl, N-2-methylpropylsulfamoyl and N-1,1-dimethylethylsulfamoyl, in particular N-methylsulfamoyl;

N-$C_1$–$C_4$-alkylsulfinamoyl, such as N-methylsulfinamoyl, N-ethylsulfinamoyl, N-n-propylsulfinamoyl, N-1-methylethylsulfinamoyl, N-n-butylsulfinamoyl, N-1-methylpropylsulfinamoyl, N-2-methylpropylsulfinamoyl and N-1,1-dimethylethylsulfinamoyl, in particular N-methylsulfinamoyl;

di-$C_1$–$C_4$-alkylsulfamoyl, such as dimethylsulfamoyl, diethylsulfamoyl, dipropylsulfamoyl, N-methyl-N-ethylsulfamoyl, N-methyl-N-propylsulfamoyl, N-methyl-N-1-methylethylsulfamoyl, N-methyl-N-1,1-dimethylethylsulfamoyl, N-ethyl-N-1-methylethylsulfamoyl and N-ethyl-N-1,1-dimethylethylsulfamoyl; in particular dimethylsulfamoyl, di-$C_1$–$C_4$-alkylsulfinamoyl, such as dimethylsulfinamoyl, diethylsulfinamoyl, dipropylsulfinamoyl, dibutylsulfinamoyl, N-methyl-N-ethylsulfinamoyl, N-methyl-N-propylsulfinamoyl, N-methyl-N-1-methylethylsulfinamoyl, N-methyl-N-1,1-dimethylethylsulfinamoyl, N-ethyl-N-1-methylethylsulfinamoyl and N-ethyl-N-1,1-dimethylethylsulfinamoyl; in particular dimethylsulfinamoyl.

The above-defined group $OSO_nR^{13}$ is, for example, $C_1$–$C_4$-alkylsulfinyloxy, such as methylsulfinyloxy, ethylsulfinyloxy, n-propylsulfinyloxy, 1-methylethylsulfinyloxy, n-butylsulfinyloxy, 1-methylpropylsulfinyloxy, 2-methylpropylsulfinyloxy and 1,l-dimethylethylsulfinyloxy, in particular methylsulfinyloxy;

$C_1$–$C_4$-alkylsulfonyloxy, such as methylsulfonyloxy, ethylsulfonyloxy, n-propylsulfonyloxy, 1-methylethylsulfonyloxy, n-butylsulfonyloxy, 1-methylpropylsulfonyloxy, 2-methylpropylsulfonyloxy and 1,1-dimethylethylsulfonyloxy, in particular methylsulfonyloxy;

$C_1$–$C_2$-haloalkylsulfonyloxy, such as chloromethylsulfonyloxy, dichloromethylsulfonyloxy, trichloromethylsulfonyloxy, fluoromethylsulfonyloxy, difluoromethylsulfonyloxy, trifluoromethylsulfonyloxy, chlorofluoromethylsulfonyloxy, dichlorofluoromethylsulfonyloxy, chlorodifluoromethylsulfonyloxy, 1-fluoroethylsulfonyloxy, 2-fluoroethylsulfonyloxy, 2,2-difluoroethylsulfonyloxy, 2,2,2-trifluoroethylsulfonyloxy, 2-chloro-2-fluoroethylsulfonyloxy, 2-chloro-2,2-difluoroethylsulfonyloxy, 2,2-dichloro-2-fluoroethylsulfonyloxy, 2,2,2-trichloroethylsulfonyloxy and pentafluoroethylsulfonyloxy, preferably trichloromethylsulfonyloxy and trifluoromethylsulfonyloxy;

The above-defined group $NR^{20}SO_nR^{13}$ is, for example, $C_1$–$C_4$-alkylsulfinylamino, such as methylsulfinylamino, ethylsulfinylamino, n-propylsulfinylamino, 1-methylethylsulfinylamino, n-butylsulfinylamino, 1-methylpropylsulfinylamino, 2-methylpropylsulfinylamino and 1,1-dimethylethylsulfinylamino, in particular methylsulfinylamino;

$C_1$–$C_4$-alkylsulfonylamino, such as methylsulfonylamino, ethylsulfonylamino, n-propylsulfonylamino, 1-methylethylsulfonylamino, n-butylsulfonylamino, 1-methylpropylsulfonylamino, 2-methylpropylsulfonylamino and 1,1-dimethylethylsulfonylamino, in particular methylsulfonylamino;

N-$C_1$–$C_4$-alkylsulfinyl-N-methylamino, such as N-methylsulfinyl-N-methylamino, N-ethylsulfinyl-N-methylamino, N-n-propylsulfinyl-N-methylamino, N-1-methylethylsulfinyl-N-methylamino, N-n-butylsulfinyl-N-methylamino, N-1-methylpropylsulfinyl-N-methylamino, N-2-methylpropylsulfinyl-N-methylamino and N-1,1-dimethylethylsulfinyl-N-methylamino, in particular N-methylsulfinyl-N-methylamino;

N-$C_1$–$C_4$-alkylsulfinyl-N-ethylamino, such as N-methylsulfinyl-N-ethylamino, N-ethylsulfinyl-N-ethylamino, N-n-propylsulfinyl-N-ethylamino, N-1-methylethylsulfinyl-N-ethylamino, N-n-butylsulfinyl-N-ethylamino, N-1-methylpropylsulfinyl-N-ethylamino, N-2-methylpropylsulfinyl-N-ethylamino and N-1,1-dimethylethylsulfinyl-N-ethylamino, in particular N-methylsulfinyl-N-ethylamino;

N-$C_1$–$C_4$-alkylsulfonyl-N-methylamino, such as N-methylsulfonyl-N-methylamino, N-ethylsulfonyl-N-methylamino, N-n-propylsulfonyl-N-methylamino, N-1-methylethylsulfonyl-N-methylamino, N-n-butylsulfonyl-N-methylamino, N-1-methylpropylsulfonyl-N-methylamino, N-2-methylpropylsulfonyl-N-methylamino and N-1,1-dimethylethylsulfonyl-N-methylamino, in particular N-methylsulfonyl-N-methylamino;

N-$C_1$–$C_4$-alkylsulfonyl-N-ethylamino, such as N-methylsulfonyl-N-ethylamino, N-ethylsulfonyl-N-ethylamino, N-n-propylsulfonyl-N-ethylamino, N-1-methylethylsulfonyl-N-ethylamino, N-n-butylsulfonyl-N-ethylamino, N-1-methylpropylsulfonyl-N-ethylamino, N-2-methylpropylsulfonyl-N-ethylamino and N-1,1-dimethylethylsulfonyl-N-ethylamino, in particular N-methylsulfonyl-N-ethylamino;

The above-defined group $OR^{15}$ is, for example, hydroxyl;

$C_1$–$C_4$-alkoxy, such as methoxy, ethoxy, n-propoxy, 1-methylethoxy, n-butoxy, 1-methylpropoxy, 2-methylpropoxy and 1,1-dimethylethoxy, in particular methoxy and ethoxy;

partially or fully halogenated $C_1$–$C_4$-alkoxy, such as chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 1,1-difluoro-2,2-difluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy, preferably $C_1$–$C_2$-haloalkoxy, such as trifluoromethoxy, difluoromethoxy, 1,1-difluoro-2,2-difluoroethyloxy;

N-$C_1$–$C_4$-alkylcarbamoyl, such as N-methylcarbamoyl, N-ethylcarbamoyl, N-n-propylcarbamoyl, N-1-methylethylcarbamoyl, N-n-butylcarbamoyl, N-1-methylpropylcarbamoyl, N-2-methylpropylcarbamoyl and N-,1l-dimethylethylcarbamoyl, in particular N-methylcarbamoyl;

di-$C_1$–$C_4$-alkylcarbamoyl, such as dimethylcarbamoyl, diethylcarbamoyl, dipropylcarbamoyl, dibutylcarbamoyl, N-methyl-N-ethylcarbamoyl, N-methyl-N-propylcarbamoyl, N-methyl-N-1-methylethylcarbamoyl, N-methyl-N-1,1-dimethylethylcarbamoyl, N-ethyl-N-1-methylethylcarbamoyl and N-ethyl-N-1,1-dimethylethylcarbamoyl, in particular dimethylcarbamoyl;

$C_1$–$C_4$-alkylcarbonyloxy, such as methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy and 1,1-dimethylethylcarbonyloxy, in particular methylcarbonyloxy;

$C_1$–$C_2$-haloalkylcarbonyloxy, such as chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, alpha-fluoropropionyl, beta-fluoropropionyl, beta,beta-difluoropropionyl, beta,beta,beta-trifluoropropionyl, beta-chloro-beta-fluoropropionyl, beta-chloro-beta,beta-difluoropropionyl, beta,beta-dichloro-beta-fluoropropionyl, beta,beta,beta-trichloropropionyl and pentafluoropropionyl, preferably trichloroacetyl and trifluoroacetyl;

The above-defined group $ZCOR^{17}$ is, for example, $C_1$–$C_4$-alkylcarbonyl, such as methylcarbonyl, ethylcarbonyl, n-propylcarbonyl, 1-methylethylcarbonyl, n-butylcarbonyl, 1-methylpropylcarbonyl, 2-methylpropylcarbonyl and 1,1-dimethylethylcarbonyl, in particular methylcarbonyl;
aminocarbonyl, hydroxycarbonyl;
$C_1$–$C_4$-alkoxycarbonyl, such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, in particular methoxycarbonyl;
$C_1$–$C_4$-alkylcarbonylamino, such as methylcarbonylamino, ethylcarbonylamino, n-propylcarbonylamino, 1-methylethylcarbonylamino, n-butylcarbonylamino, 1-methylpropylcarbonylamino, 2-methylpropylcarbonylamino and 1,1-dimethylethylcarbonylamino, in particular methylcarbonylamino;
$C_1$–$C_4$-alkylcarbonyl-N-methylamino, such as N-methylcarbonyl-N-methylamino, N-ethylcarbonyl-N-methylamino, N-n-propylcarbonyl-N-methylamino, N-1-methylethylcarbonyl-N-methylamino, N-n-butylcarbonyl-N-methylamino, N-1-methylpropylcarbonyl-N-methylamino, N-2-methylpropylcarbonyl-N-methylamino and N-1,1-dimethylethylcarbonyl-N-methylamino, in particular N-methylcarbonyl-N-methylamino;
N-$C_1$–$C_4$-alkylaminocarbonylamino, such as N-methylaminocarbonylamino, N-ethylaminocarbonylamino, N-n-propylaminocarbonylamino, N-1-methylethylaminocarbonylamino, N-n-butylaminocarbonylamino, N-1-methylpropylaminocarbonylamino, N-2-methylpropylaminocarbonylamino and N-1,1-dimethylethylaminocarbonylamino, in particular methylaminocarbonylamino;
N-$C_1$–$C_4$-alkylaminocarbonyl-N-methylamino, such as N-methylaminocarbonyl-N-methylamino, N-ethylaminocarbonyl-N-methylamino, N-n-propylaminocarbonyl-N-methylamino, N-1-methylethylaminocarbonyl-N-methylamino, N-n-butylaminocarbonyl-N-methylamino, N-1-methylpropylaminocarbonyl-N-methylamino, N-2-methylpropylaminocarbonyl-N-methylamino and N-1,1-dimethylethylaminocarbonyl-N-methylamino, in particular N-methylaminocarbonyl-N-methylamino;
N,N-di-$C_1$–$C_4$-alkylaminocarbonylamino, such as N,N-dimethylaminocarbonylamino, N,N-diethylaminocarbonylamino, N,N-dipropylaminocarbonylamino, N,N-dibutylaminocarbonylamino, N-methyl-N-ethylaminocarbonylamino, N-methyl-N-propylaminocarbonylamino, N-methyl-N-1-methylethylaminocarbonylamino, N-methyl-N-1,1-dimethylethylaminocarbonylamino, di-1-methylethylaminocarbonylamino, N-ethyl-N-1-methylethylaminocarbonylamino and N-ethyl-N-1,1-dimethylethylaminocarbonylamino, in particular dimethylaminocarbonylamino;
N,N-di-$C_1$–$C_4$-alkylaminocarbonyl-N-methylamino, such as N,N-dimethylaminocarbonyl-N-methylamino, N,N-diethylaminocarbonyl-N-methylamino, N,N-dipropylaminocarbonyl-N-methylamino, N,N-dibutylaminocarbonyl-N-methylamino, N-methyl-N-ethylaminocarbonyl-N-methylamino, N-methyl-N-propylaminocarbonyl-N-methylamino, N-methyl-N-1-methylethylaminocarbonyl-N-methylamino, N-methyl-N-1,1-dimethylethylaminocarbonyl-N-methylamino, di-1-methylethylaminocarbonyl-N-methylamino, N-ethyl-N-1-methylethylaminocarbonyl-N-methylamino and N-ethyl-N-1,1-dimethylethylaminocarbonyl-N-methylamino, in particular dimethylaminocarbonyl-N-methylamino;
$C_1$–$C_4$-alkylcarbonate, such as methylcarbonate, ethylcarbonate, propylcarbonate, 1-methylethylcarbonate, butylcarbonate, 1-methylpropylcarbonate, 2-methylpropylcarbonate, 1,1-dimethylethylcarbonate;
all carbon radicals of the above-defined groups can be unsubstituted or substituted by one to five halogen atoms, such as fluorine, chlorine, bromine and iodine, preferably fluorine and chlorine, $C_1$–$C_4$-alkoxy, preferably methoxy and ethoxy, $C_1$–$C_4$-alkylthio, preferably methylthio and ethylthio, cyano, nitro or phenyl;
$R^2$ can be a substituent mentioned under $R^1$ which is identical to or different from $R^1$;
$R^3$ can be a substituent mentioned under $R^1$ which is identical to or different from $R^1$;
$R^4$ can be a substituent mentioned under $R^1$ which is identical to or different from $R^1$;
$R^5$ can be a substituent mentioned under $R^1$ which is identical to or different from $R^1$;
two adjacent radicals $R^1$ and $R^2$, $R^2$ and $R^3$, $R^3$ and $R^4$, $R^4$ and $R^5$ preferably $R^1$ and $R^2$, form a cyclic, five-membered acetal/carbonate, it being possible for the ring carbon atom to have attached to it a divalent oxygen, two bromine atoms, two chlorine atoms or two fluorine atoms, preferably two fluorine atoms;
$R^8$ can be:
$C_3$–$C_6$-Cycloalkyl, such as cyclopropyl, 1-methylcyclopropyl, cyclobutyl, cyclopentyl, cyclohexyl, preferably cyclopropyl, 1-methylcyclopropyl;
$C_1$–$C_4$-alkyl as defined above for $R^1$;
partially or fully halogenated $C_1$–$C_4$-alkyl as defined for $R^1$;
$C_1$–$C_4$-alkoxy-$C_1$–$C_4$-alkyl as defined above for $R^1$;
$ZCOR^{17}$ as defined above for $R^1$.
$R^{11}$ can be:
$C_1$–$C_4$-alkyl as defined above for $R^1$;
partially or fully halogenated $C_1$–$C_4$-alkyl as defined for $R^1$;
$C_2$–$C_4$-alkenyl as defined above for $R^1$;
$C_2$–$C_4$-alkynyl as defined above for $R^1$;
$C_3$–$C_6$-cycloalkyl as defined above for $R^8$;
$(CH_2)_m SO_n R^{16}$ as defined above for $R^1$;
it being possible for all carbon radicals of the above-defined groups to be unsubstituted or substituted by one to five halogen atoms, such as fluorine, chlorine, bromine and iodine, preferably fluorine and chlorine, or by one to two of the following groups: $C_1$–$C_4$-alkoxy, preferably methoxy and ethoxy, $C_1$–$C_4$-alkylthio, preferably methylthio and ethylthio, cyano, nitro;
substituted phenylsulfonyl, such as 2,4-difluorophenylsulfonyl, 2,4-dichlorophenylsulfonyl, 2',2'-difluoro-4,5-benzodioxolan-3-ylsulfonyl, 3-trifluoromethylphenylsulfonyl, 3-fluorophenylsulfonyl, 3-chlorophenylsulfonyl,
preferably 2,4-difluorophenylsulfonyl, 2',2'-difluoro-4,5-benzodioxolan-3-ylsulfonyl, 3-trifluoromethylphenylsulfonyl;
substituted phenylsulfinyl, such as 2,4-difluorophenylsulfinyl, -2,4-dichlorophenylsulfinyl, 2',2'-difluoro-4,5-benzodioxolan-3-ylsulfinyl, 3-trifluoromethylphenylsulfinyl, 3-fluorophenylsulfinyl, 3-chlorophenylsulfinyl,
preferably 2,4-difluorophenylsulfinyl, 2',2'-difluoro-4,5-benzo-dioxolan-3-ylsulfinyl, 3-trifluoromethylphenylsulfinyl;

substituted phenyl, such as 2,4-difluorophenyl, 2,4-dichlorophenyl, 2',2'-difluoro-4,5-benzodioxolan-3-ylphenyl, 3-trifluoromethylphenyl, 3-fluorophenyl, 3-chlorophenyl, 2-cyano-4-fluorophenyl, 2-nitro-4-fluorophenyl, 2-dimethylamino-4-fluorophenyl, 2-sulfonylmethyl-4-fluorophenyl, 2-fluoro-4-nitrophenyl, 2-fluoro-4-sulfonylmethylphenyl, 2-sulfonylmethyl-4-trifluoromethylphenyl, preferably 2,4-difluorophenyl, 2',2'-difluoro-4,5-benzodioxolan-3-ylphenyl, 3-trifluoromethylphenyl, 2-sulfonylmethyl-4-trifluoromethylphenyl;

$R^{11}$ may also be a group $CXR^{18}$ where X=O;

$R^{18}$ can be:

hydrogen;

$C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropylcarbonyl or 1-ethyl-2-methylpropyl in particular methyl, ethyl, 1-methylethyl;

$C_1$–$C_6$-alkoxy, such as methoxy, ethoxy, propyloxy, 1-methylethoxy, butyloxy, 1-methylpropyloxy, 2-methylpropyloxy, 2 1,-dimethylethoxy, pentyloxy, 1-methylbutyloxy, 2-methylbutyloxy, 3-methylbutyloxy, 1,1-dimethylpropyloxy, 1,2-dimethylpropyloxy, 2,2-dimethylpropyloxy, 1-ethylpropyloxy, hexyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 1,1,2-trimethylpropyloxy, 1,2,2-trimethylpropyloxy, 1-ethyl-1-methylpropyloxycarbonyl or 1-ethyl-2-methyl-propyloxy, in particular methoxy, ethoxy, 1-methylethoxy, 1,1-dimethylethoxy;

partially or fully halogenated $C_1$–$C_6$-alkoxy, such as chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy, preferably $C_1$–$C_2$-haloalkoxy, such as trifluoromethoxy;

$C_2$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2$–$C_6$-alkynyl, such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably propargyl;

$C_3$–$C_6$-cycloalkyl, such as cyclopropyl, 1-methylcyclopropyl, cyclobutyl, cyclopentyl, cyclohexyl, preferably cyclopropyl, 1-methylcyclopropyl;

partially or fully halogenated $C_1$–$C_4$-alkyl, such as defined for $R^1$;

$C_1$–$C_4$-alkoxy-$C_1$–$C_2$-alkyl, such as methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, methoxyethyl, ethoxyethyl, n-propoxyethyl, (1-methylethoxy)ethyl, n-butoxyethyl, (1-methylpropoxy)ethyl, (2-methylpropoxy)ethyl, (1,1-dimethylethoxy)ethyl, 3-(methoxy)propyl, 2-(methoxy)propyl and 2-(ethoxy)propyl, preferably $C_1$–$C_4$-alkoxy-$C_1$–$C_2$-alkyl, such as methoxymethyl, ethoxymethyl, 2-methoxyethyl and 2-ethoxyethyl;

cyano($C_1$–$C_6$)alkyl, such as cyanomethyl, 1-cyanoeth-1-yl, 2-cyanoeth-1-yl, l-cyanoprop-1-yl, 2-cyanoprop-1-yl, 3-cyanoprop-1-yl, 1-cyanoprop-2-yl, 2-cyanoprop-2-yl, l-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, and 2-cyanomethylprop-2-yl, preferably cyanomethyl, 2-cyanoeth-1-yl;

N-$C_1$–$C_4$-alkylamino, such as N-methylamino, N-ethylamino, N-n-propylamino, N-1-methylethylamino, N-n-butylamino, N-1-methylpropylamino, N-2-methylpropylamino and N-1,1-dimethylethylamino, in particular N-methylamino, N-1-methylethylamino;

N,N-di-$C_1$–$C_4$-alkylamino, such as N,N-dimethylamino, N,N-diethylamino, N,N-dipropylamino, N,N-dibutylamino, N-methyl-N-ethylamino, N-methyl-N-propylamino, N-methyl-N-1-methylethylamino, N-methyl-N-1,1-dimethylethylamino, di-1-methylethylamino, N-ethyl-N-1-methylethylamino and N-ethyl-N-1,1-dimethylethylamino, in particular dimethylamino, N,N-diethylamino;

$R^{11}$ may also be a group $CXR^{18}$ where X=S and $R^{18}$ is as already defined above:

in this case, $R^{11}$ would preferably be:

thioformyl, methylthiocarbonyl, ethylthiocarbonyl, 1-methylethylthiocarbonyl;

methoxythiocarbonyl, ethoxythiocarbonyl, 1-methylethoxythiocarbonyl, 2,2-dimethylethoxythiocarbonyl;

$C_1$–$C_2$-haloalkoxythiocarbonyl, such as trifluoromethoxythiocarbonyl;

1-methyl-2-propenylthiocarbonyl, 1-methyl-2-butenylthiocarbonyl, 1,1-dimethyl-2-propenyl and 1,1-dimethyl-2-butenylthiocarbonyl;

propargylthiocarbonyl, cyclopropylthiocarbonyl, 1-methylcyclopropylthiocarbonyl;

trifluoromethylthiocarbonyl;

$C_1$–$C_4$-alkoxy-$C_1$–$C_2$-alkylthiocarbonyl, such as methoxymethylthiocarbonyl, ethoxymethylthiocarbonyl, 2-methoxyethylthiocarbonyl and 2-ethoxyethylthiocarbonyl;

cyanomethylthiocarbonyl, 2-cyanoeth-1-ylthiocarbonyl;

methylaminothiocarbonyl, N-1-methylethylaminothiocarbonyl;

dimethylaminothiocarbonyl, N,N-diethylaminothiocarbonyl;

$R^{11}$ may also be a group $CXR^{18}$ where X=NH and $R^{18}$ is as already defined above:

in this case, $R^{11}$ would preferably be:

1-iminomethyl, 1-iminoethyl, 1-imino-2-methylpropyl;

1-imino-1-methoxymethyl, 1-ethoxy-1-iminomethyl;

1-imino-1-(1-methylethoxy)methyl, 1-(2,2-dimethylethoxy)-1-iminomethyl;

$C_1$–$C_2$-haloalkoxyiminomethyl, such as 1-trifluoromethoxy-1-iminomethyl;

1-imino-2-methyl-2-propenyl, 1-imino-2-methyl-2-butenyl, 1-imino-2,3-dimethyl-2-propenyl and 1-imino-3-methyl-2-butenyl;

1-imino-2-butynyl;

iminomethylcyclopropyl, 1-iminomethyl-1-methylcyclopropyl;

1-imino-2,2,2-trifluoroethyl;

1-imino-2-methoxyethyl, 1-imino-2-ethoxyethyl, 1-imino-2-(1-methylethoxy)ethyl;

2-cyano-1-iminoethyl, 3-cyano-1-iminopropyl;

1-imino-N-methylaminomethyl, 1-imino-N-ethylaminomethyl, 1-imino(N-1-methylethylamino)methyl;

N,N-dimethylaminoiminomethyl, N,N-diethylaminoiminomethyl;

$R^{11}$ may also be a group $CXR^{18}$ where X is =N-$C_1$–$C_4$-alkyl and $R^{18}$ is as already defined above:

in this case, $R^{11}$ would preferably be:

methyliminomethyl, 1-methyliminoethyl, 1-methylimino-2-methylpropyl, ethyliminomethyl, 1-ethyliminoethyl, 1-ethylimino-2-methylpropyl, (1-methylethyl)iminomethyl, 1-(1-methylethyl)iminoethyl, 1-(1-methylethyl)imino-2-methylpropyl;

1-methoxy-1-methyliminomethyl, 1-ethoxy-1-methyliminomethyl, 1-(1-methylethoxy)-1-methyliminomethyl, 1-(2,2-dimethylethoxy)-1-methyliminomethyl, 1-methoxy-1-ethyliminomethyl, 1-ethoxy-1-ethyliminomethyl, 1-(1-methylethoxy)-1-ethyliminomethyl, 1-(2,2-dimethylethoxy)-1-ethyliminomethyl;

$C_1$–$C_2$-haloalkoxyiminomethyl, such as trifluoromethoxymethyliminomethyl;

2-methyl-1-methylimino-2-propenyl, 2-methyl-1-methylimino-2-butenyl, 2,3-dimethyl-1-methylimino-2-propenyl and 3-methyl-1-methylimino-2-butenyl, 1-ethylimino-2-methyl-2-propenyl, 1-ethylimino-2-methyl-2-butenyl, 2,3-dimethyl-1-ethylimino-2-propenyl and 1-ethylimino-3-methyl-2-butenyl;

1-methylimino-2-butynyl, 1-ethylimino-2-butynyl;

methyliminomethylcyclopropyl, 1-methyl-1-methyliminomethyl-cyclopropyl;

1-methylimino-2,2,2-trifluoroethyl;

2-methoxy-1-methyliminoethyl, 2-ethoxy-1-methyliminoethyl, 2-(1-methylethoxy)-1-methyliminoethyl, 1-ethylimino-2-methoxyethyl, 2-ethoxy-1-ethyliminoethyl, 1-ethylimino-2-(1-methylethoxy)ethyl;

2-cyano-1-methyliminoethyl, 3-cyano-1-methyliminopropyl, 2-cyano-1-ethyliminoethyl, 3-cyano-1-ethyliminopropyl;

1-N-methylamino-1-methyliminomethyl, 1-N-ethylamino-1-methyliminomethyl, 1-(N-1-methylethylamino)-1-methyliminomethyl, 1-ethylimino-1-N-methylaminomethyl, 1-N-ethylamino-1-ethyliminomethyl, 1-ethylimino-1-(N-1-methylethylamino)methyl;

N,N-dimethylaminomethyliminomethyl, N,N-diethylaminomethyliminomethyl, N,N-dimethylaminoethyliminomethyl, N,N-diethylaminoethyliminomethyl;

it being possible for all carbon radicals in the definition of Rll to be unsubstituted or substituted by one to five halogen atoms, such as fluorine, chlorine, bromine and iodine, preferably fluorine and chlorine, $C_1$–$C_4$-alkoxy as mentioned for $R^1$, preferably methoxy and ethoxy, $C_1$–$C_4$-alkylthio as mentioned for $R^1$, preferably methylthio and ethylthio, cyano, nitro, $C_1$–$C_4$-alkylamino as mentioned for $R^1$, cyanato, thiocyanato, $OR^{15}$ as defined above, $(CH_2)_m SO_n R^{16}$ as defined above, $NSO_n R^{13}$ as defined above, $OSO_n R^{13}$ as defined above, $ZCOR^{17}$ as defined above;

$R^{11}$ can furthermore be:

a 5- or 6-membered heterocyclic, saturated or unsaturated ring containing one to four hetero atoms selected from the group consisting of oxygen, sulfur or nitrogen, for example a five-membered heteroaromatic ring, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl, 1,2,4-triazol-3-yl, 1,3,4-triazol-2-yl, 1,2,3-triazol-4-yl, 1,2,3-triazol-5-yl, 1,2,4-triazol-5-yl, tetrazol-5-yl, in particular 2-thiazolyl and 3-isoxazolyl;

a six-membered heteroaromatic ring, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-5-yl and 1,2,4-triazin-3-yl, 1,2,4-triazin-6-yl, 1,2,4,5-tetrazin-3-yl;

a 5- to 6-membered saturated or partially unsaturated heterocycle containing one to three nitrogen atoms and/or one or two oxygen or sulfur atoms, such as 2-tetrahydrofuranyl, 3-tetrahydrofuranyl, 2-tetrahydrothienyl, 3-tetrahydrothienyl, tetrahydrothiopyran-2-yl, tetrahydrothiopyran-3-yl, tetrahydrothiopyran-4-yl, 1,3-dithiolan-2-yl, 1,3-dithiolan-4-yl, 1-3-dithian-2-yl, 1,3-dithian-4-yl, 5,6-dihydro-4H-1,3-thiazin-2-yl, 1,3-oxathiolan-2-yl, 1,3-oxathian-2-yl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 1,3-dioxolan-2-yl, 1,3-dioxolan-4-yl, 1,3-dioxan-5-yl, 1,4-dioxan-2-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, in particular 2-tetrahydrofuranyl, 1,3-dioxolan-2-yl and 1,3-dioxan-2-yl;

All the abovementioned ring systems can be unsubstituted or substituted by the following substituents:

halogen as mentioned above, in particular fluorine or chlorine;

cyano, nitro;

a group —$ZCOR^{17}$, for example alkylcarbonyl as mentioned above, alkoxycarbonyl as mentioned above, N-alkylcarbamoyl as mentioned above, dialkylcarbamoyl as mentioned above;

$C_1$–$C_4$-alkyl as mentioned above;

$C_1$–$C_4$-haloalkyl, such as, for example, chloromethyl, difluoromethyl, dichloromethyl, trifluoromethyl, trichloromethyl, chlorodifluoromethyl, 1-fluoroethyl, 2-fluoroethyl, 2,2-difluoroethyl, 1,1,2,2-tetrafluoroethyl, 2,2,2-trifluoroethyl, 2-chloro-1,1,2-trifluoroethyl and pentafluoroethyl, decafluorobutyl, 1,1-bis-trifluoromethyl-2,2,2-trifluoroethyl, preferably difluoromethyl, trifluoromethyl, trichloromethyl and chlorodifluoromethyl;

$C_1$–$C_4$-alkoxy as mentioned above;

$C_1$–$C_4$-haloalkoxy such as, for example, chloromethoxy, dichloromethoxy, trichloromethoxy, fluoromethoxy, difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular $C_1$–$C_3$-haloalkoxy, such as 2,2,2-trifluoroethoxy and 2-chloro-2,2-difluoroethoxy;

$C_1$–$C_4$-alkylthio as mentioned above;

$C_1$–$C_4$-haloalkylthio as mentioned above;

or a divalent oxygen which may also exist as hydroxyl group in the tautomeric form, for example thiazolin-4,5-dion-2-yl, 3-oxo-3H-1,2,4-dithiazolyl or 2-oxo-2H-1,3,4-dithiazolyl;

examples of benzo-fused 5- or 6-membered heteroaromatic rings are benzofuranyl, benzothienyl, indolyl, benzoxazolyl, benzoisoxazolyl, benzothiazolyl, benzoisothiazolyl, benzopyrazolyl, indazolyl, 1,2,3-benzothiadiazolyl, 2,1,3-benzothiadiazolyl, benzotriazolyl, benzofuroxanyl, quinolinyl, isoquinolinyl, cinnolinyl, quinazolinyl, quinoxalinyl or phthalazinyl;

$R^{11}$ can furthermore be:

$(CH_2)_p R^{19}$: an above-defined $C_1$–$C_4$-alkyl chain which can be substituted by the following radicals:

2,2-difluorobenzodioxolan-5-yl $C_1$–$C_4$-alkylamino as defined above for $R^1$, $C_1$–$C_4$-dialkylamino as defined above for $R^1$, $(CH_2)_m SO_n R^{16}$ as defined above;

$NSO_n R^{13}$ as defined above;

$OSO_n R^{13}$ as defined above;

$ZOCR^{17}$ as defined above;

$C_3$–$C_6$-cycloalkyl as defined above which can be unsubstituted or substituted by one to four halogen atoms, fluorine, chlorine bromine, iodine or $C_1$–$C_4$-alkoxy as defined for $R^1$;

phenyl which is unsubstituted or can have attached to it one to five of the following substituents: fluorine, chlorine, bromine, iodine, nitro, cyano, $C_1$–$C_4$-alkyl as defined for $R^1$, $C_1$–$C_4$-haloalkyl as defined for $R^1$, $C_1$–$C_4$-alkylamino as defined for $R^1$, $C_1$–$C_4$-dialkylamino as defined for $R^1$, OCN, $OR^{15}$ as defined for $R^1$, $SF_5$, SCN, $(CH_2)_m SO_n R^{16}$ as defined for-$R^1$, $NSO_n R^{13}$ as defined for $R^1$, $OSO_n R^{13}$ as defined for $R^1$, $ZCOR^{17}$ as defined for $R^1$;

phenoxy which is unsubstituted or can have attached to it one to five of the following substituents: fluorine, chlorine, bromine, iodine, nitro, cyano, $C_1$–$C_4$-alkyl as defined for $R^1$, $C_1$–$C_4$-haloalkyl as defined for $R^1$, $C_1$–$C_4$-alkylamino as defined for $R^1$, $C_1$–$C_4$-dialkylamino as defined for $R^1$, OCN, $OR^{15}$ as defined for $R^1$, $SF_5$, SCN, $(CH_2)_m SO_n R^{16}$ as defined for $R^1$, $NSO_n R^{13}$ as defined for $R^1$, $OSO_n R^{13}$ as defined for $R^1$, $ZCOR^{17}$ as defined for $R^1$;

a 5- or 6-membered heterocyclic, saturated or unsaturated radical containing one to three hetero atoms selected from the group consisting of oxygen, sulfur or nitrogen, for example a five-membered heteroaromatic ring, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl, 1,2,4-triazol-3-yl, 1,3,4-triazol-2-yl, 1,2,3-triazol-4-yl, 1,2,3-triazol-5-yl, 1,2,4-triazol-5-yl, tetrazol-5-yl, in particular 2-thiazolyl and 3-isoxazolyl;

a six-membered heteroaromatic ring, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-5-yl and 1,2,4-triazin-3-yl, 1,2,4-triazin-6-yl, 1,2,4,5-tetrazin-3-yl;

a 5- to 6-membered saturated or partially unsaturated heterocycle containing one to three nitrogen atoms and/or one or two oxygen or sulfur atoms, such as 2-tetrahydrofuranyl, 3-tetrahydrofuranyl, 2-tetrahydrothienyl, 3-tetrahydrothienyl, tetrahydrothiopyran-2-yl, tetrahydrothiopyran-3-yl, tetrahydrothiopyran-4-yl, 1,3-dithiolan-2-yl, 1,3- dithiolan-4-yl, 1–3-dithian-2-yl, 1,3-dithian-4-yl, 5,6-dihydro-4H-1,3-thiazin-2-yl, 1,3-oxathiolan-2-yl, 1,3-oxathian-2-yl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 1,3-dioxolan-2-yl, 1,3-dioxolan-4-yl, 1,3-dioxan-5-yl, 1,4-dioxan-2-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, in particular 2-tetrahydrofuranyl, 1,3-dioxolan-2-yl and 1,3-dioxan-2-yl;

All the abovementioned ring systems can be unsubstituted or substituted by the following substituents:

halogen as mentioned above, in particular fluorine or chlorine;

cyano, nitro;

a group —ZCOR$^{17}$, for example alkylcarbonyl as mentioned above, alkoxycarbonyl as mentioned above, N-alkylcarbamoyl as mentioned above, dialkylcarbamoyl as mentioned above;

$C_1$–$C_4$-alkyl as mentioned above;

$C_1$–$C_4$-haloalkyl, such as, for example, chloromethyl, difluoromethyl, dichloromethyl, trifluoromethyl, trichloromethyl, chlorodifluoromethyl, 1-fluoroethyl, 2-fluoroethyl, 2,2-difluoroethyl, 1,1,2,2-tetrafluoroethyl, 2,2,2-trifluoroethyl, 2-chloro-1,1,2-trifluoroethyl and pentafluoroethyl, decafluorobutyl, 1,1-bis-trifluoromethyl-2,2,2-trifluoroethyl, preferably difluoromethyl, trifluoromethyl, trichloromethyl and chlorodifluoromethyl;

$C_1$–$C_4$-alkoxy as mentioned above;

$C_1$–$C_4$-haloalkoxy such as, for example, chloromethoxy, dichloromethoxy, trichloromethoxy, fluoromethoxy, difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular $C_1$–$C_3$-haloalkoxy, such as 2,2,2-trifluoroethoxy and 2-chloro-2,2-difluoroethoxy;

$C_1$–$C_4$-alkylthio as mentioned above;

$C_1$–$C_4$-haloalkylthio as mentioned above;

or a divalent oxygen which may also exist as hydroxyl group in the tautomeric form, for example thiazolin-4,5-dion-2-yl, 3-oxo-3H-1,2,4-dithiazolyl or 2-oxo-2H-1,3,4-dithiazolyl;

examples of benzo-fused 5- or 6-membered heteroaromatic rings are benzofuranyl, benzothienyl, indolyl, benzoxazolyl, benzisoxazolyl, benzthiazolyl, benzisothiazolyl, benzpyrazolyl, indazolyl, 1,2,3-benzothiadiazolyl, 2,1,3-benzothiadiazolyl, benzotriazolyl, benzofuroxanyl, quinolinyl, isoquinolinyl, cinnolinyl, quinazolinyl, quinoxalinyl or phthalazinyl;

$R^{11}$ can furthermore be:

an above-defined $C_1$–$C_4$-alkyl which is substituted a) by a 5- or 6-membered cyclic (thio)acetal, preferably dioxolan-2-yl;

b) by above-defined $C_1$–$C_4$-alkoxy which, in turn, can have attached to it cyano, nitro or, if appropriate, halogen radicals.

$R^{12}$ can be:

hydrogen;

an above-defined $C_1$–$C_4$-alkyl;

an above-defined $C_3$–$C_6$-cycloalkyl.

$R^{11}$ and $R^{12}$ may also form a double bond which can be substituted by two identical or different substituents $R^{14}$ from amongst the following:

$R^{14}$: hydrogen;

$C_1$–$C_6$-alkyl as defined for $R^{18}$;

$C_3$–$C_6$-cycloalkyl as defined for $R^{18}$;

$C_2$–$C_6$-alkynyl as defined for $R^{18}$;

$C_1$–$C_6$-alkenyl as defined for $R^{18}$;

it being possible for all carbon radicals which have been defined to be unsubstituted or substituted by one to five halogen atoms, such as fluorine, chlorine, bromine and iodine, preferably fluorine and chlorine, $C_1$–$C_4$-alkoxy as mentioned for $R^1$, preferably methoxy and ethoxy, $C_1$–$C_4$-alkylthio as mentioned for $R^1$, preferably methylthio and ethylthio, cyano, nitro, substituted phenyl as defined above, $OR^{15}$ as defined above, $ZCOR^{17}$ as defined above.

Phenyl which is unsubstituted or substituted as defined above for $R^{11}$;

a 5- or 6-membered heterocyclic, saturated or unsaturated ring containing one to four hetero atoms selected from the group consisting of oxygen, sulfur or nitrogen, for example five- and six-membered heterocycles as described for $R^5$.

Preferred N-aminopyridone derivatives are those of the general formulae Id-m whose substituents have the meanings mentioned at the outset:

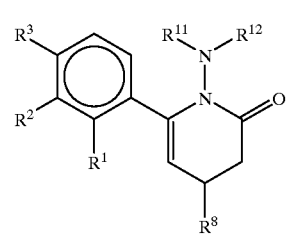

Id

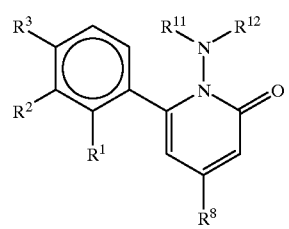
Ie

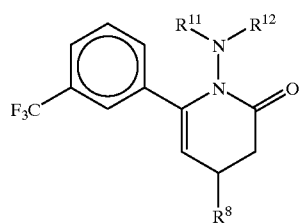
If

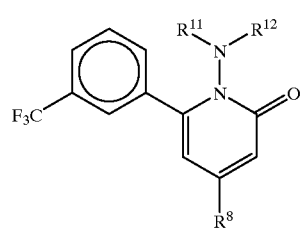
Ig

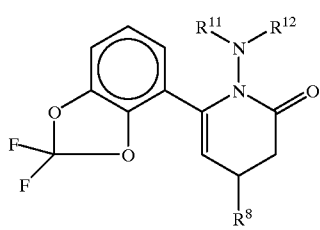
Ih

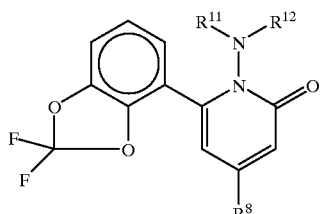
Ii

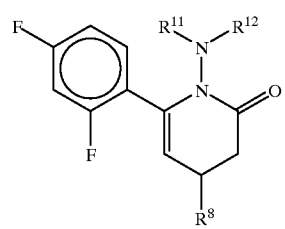
Ij

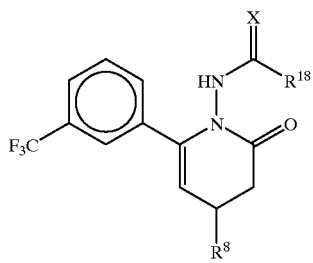
Il

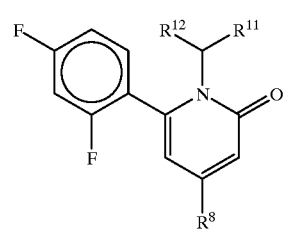
Ik

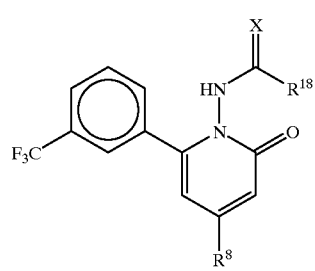
Im

TABLE 1

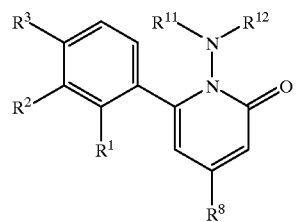
Ie

| No. | $R^1$ | $R^2$ | $R^3$ | $R^8$ | $R^{12}$ | $R^{11}$ |
|---|---|---|---|---|---|---|
| 1.1 | F | H | F | $CH_3$ | H | —$CH_3$ |
| 1.2 | F | H | F | $CH_3$ | H | —H |
| 1.3 | F | H | F | $CH_3$ | H | —$C_2H_5$ |
| 1.4 | F | H | F | $CH_3$ | H | -$^i$Pr |
| 1.5 | F | H | F | $CH_3$ | H | -$^t$Bu |
| 1.6 | F | H | F | $CH_3$ | H | —$CH_2OCH_3$ |
| 1.7 | F | H | F | $CH_3$ | H | —$CH_2OC_2H_5$ |
| 1.8 | F | H | F | $CH_3$ | H | —$COOCH_3$ |
| 1.9 | F | H | F | $CH_3$ | H | —$COOC_2H_5$ |
| 1.10 | F | H | F | $CH_3$ | H | —$COO^iPr$ |
| 1.11 | F | H | F | $CH_3$ | H | —$COO^tBu$ |
| 1.12 | F | H | F | $CH_3$ | H | —$COOCF_3$ |
| 1.13 | F | H | F | $CH_3$ | H | —$COOCHF_2$ |
| 1.14 | F | H | F | $CH_3$ | H | —$COOCH_2CF_3$ |
| 1.15 | F | H | F | $CH_3$ | H | —$COOCH_2CHF_2$ |
| 1.16 | F | H | F | $CH_3$ | H | —$COCH_3$ |
| 1.17 | F | H | F | $CH_3$ | H | —$COC_2H_5$ |
| 1.18 | F | H | F | $CH_3$ | H | —$CO^iPr$ |
| 1.19 | F | H | F | $CH_3$ | H | —$CO^tBu$ |
| 1.20 | F | H | F | $CH_3$ | H | —$COCH_2CN$ |
| 1.21 | F | H | F | $CH_3$ | H | —$COCH_2CH_2CN$ |
| 1.22 | F | H | F | $CH_3$ | H | —$CH_2COOCH_3$ |

TABLE 1-continued

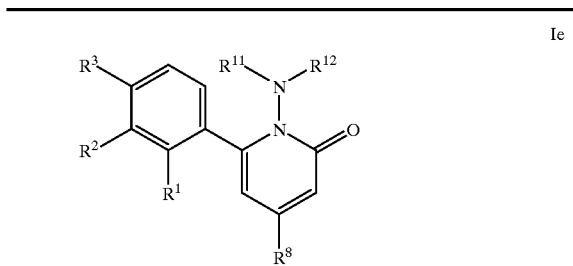

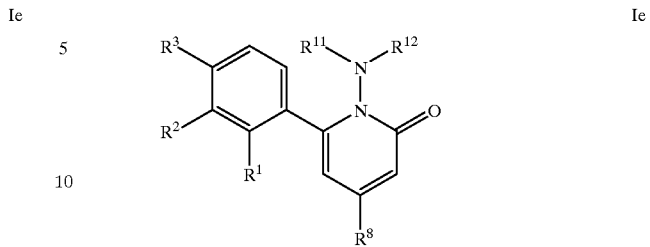

| No. | R¹ | R² | R³ | R⁸ | R¹² | R¹¹ |
|---|---|---|---|---|---|---|
| 1.23 | F | H | F | CH₃ | H | —CH₂COOC₂H₅ |
| 1.24 | F | H | F | CH₃ | H | —CH₂COOⁱPr |
| 1.25 | F | H | F | CH₃ | H | -Ph |
| 1.26 | F | H | F | CH₃ | H | -3-F-Ph |
| 1.27 | F | H | F | CH₃ | H | -3-NO₂-Ph |
| 1.28 | F | H | F | CH₃ | H | -3-SO₂Me-Ph |
| 1.29 | F | H | F | CH₃ | H | -3-F-Ph |
| 1.30 | F | H | F | CH₃ | H | -3-CF₃-Ph |
| 1.31 | F | H | F | CH₃ | H | -2,4-F₂-Ph |
| 1.32 | F | H | F | CH₃ | H | -2-CF₃-Ph |
| 1.33 | F | H | F | CH₃ | H | -4-CF₃Ph |
| 1.34 | F | H | F | CH₃ | H | —COCF₃ |
| 1.35 | F | H | F | CH₃ | H | —COCH₂CF₃ |
| 1.36 | F | H | F | CH₃ | H | —COPh |
| 1.37 | F | H | F | CH₃ | H | —CO-3-Cl-Ph |
| 1.38 | F | H | F | CH₃ | H | —CO-3-F-Ph |
| 1.39 | F | H | F | CH₃ | H | —CO-3-NO₂Ph |
| 1.40 | F | H | F | CH₃ | H | —CO-3-SO₂CH₃-Ph |
| 1.41 | F | H | F | CH₃ | H | —CO-3-CF₃-Ph |
| 1.42 | F | H | F | CH₃ | H | —CO-2,4-F₂-Ph |
| 1.43 | F | H | F | CH₃ | H | —CH₂—CF₃ |
| 1.44 | F | H | F | CH₃ | H | —CH₂—CH₂—CF₃ |
| 1.45 | F | H | F | CH₃ | H | —CF₃ |
| 1.46 | F | H | F | CH₃ | H | —CONHCH₃ |
| 1.47 | F | H | F | CH₃ | H | —CONHC₂H₅ |
| 1.48 | F | H | F | CH₃ | H | —CONHⁱPr |
| 1.49 | F | H | F | CH₃ | H | —CONHᵗBu |
| 1.50 | F | H | F | CH₃ | H | —CONH₂ |
| 1.51 | F | H | F | CF₃ | H | —CH₃ |
| 1.52 | F | H | F | CF₃ | H | —H |
| 1.53 | F | H | F | CF₃ | H | —C₂H₅ |
| 1.54 | F | H | F | CF₃ | H | -ⁱPr |
| 1.55 | F | H | F | CF₃ | H | -ᵗBu |
| 1.56 | F | H | F | CF₃ | H | —CH₂OCH₃ |
| 1.57 | F | H | F | CF₃ | H | —CH₂OC₂H₅ |
| 1.58 | F | H | F | CF₃ | H | —COOCH₃ |
| 1.59 | F | H | F | CF₃ | H | —COOC₂H₅ |
| 1.60 | F | H | F | CF₃ | H | —COOⁱPr |
| 1.61 | F | H | F | CF₃ | H | —COOᵗBu |
| 1.62 | F | H | F | CF₃ | H | —COOCF₃ |
| 1.63 | F | H | F | CF₃ | H | —COOCHF₂ |
| 1.64 | F | H | F | CF₃ | H | —COOCH₂CF₃ |
| 1.65 | F | H | F | CF₃ | H | —COOCH₂CHF₂ |
| 1.66 | F | H | F | CF₃ | H | —COCH₃ |
| 1.67 | F | H | F | CF₃ | H | —COC₂H₅ |
| 1.68 | F | H | F | CF₃ | H | —COⁱPr |
| 1.69 | F | H | F | CF₃ | H | —COᵗBu |
| 1.70 | F | H | F | CF₃ | H | —COCH₂CN |
| 1.71 | F | H | F | CF₃ | H | —COCH₂CH₂CN |
| 1.72 | F | H | F | CF₃ | H | —CH₂COOCH₃ |
| 1.73 | F | H | F | CF₃ | H | —CH₂COOC₂H₅ |
| 1.74 | F | H | F | CF₃ | H | —CH₂COOⁱPr |
| 1.75 | F | H | F | CF₃ | H | -Ph |
| 1.76 | F | H | F | CF₃ | H | -3-F-Ph |
| 1.77 | F | H | F | CF₃ | H | -3-NO₂-Ph |
| 1.78 | F | H | F | CF₃ | H | -3-SO₂Me-Ph |
| 1.79 | F | H | F | CF₃ | H | -3-F-Ph |
| 1.80 | F | H | F | CF₃ | H | -3-CF₃-Ph |
| 1.81 | F | H | F | CF₃ | H | -2,4-F₂-Ph |
| 1.82 | F | H | F | CF₃ | H | -2-CF₃-Ph |
| 1.83 | F | H | F | CF₃ | H | -4-CF₃Ph |
| 1.84 | F | H | F | CF₃ | H | —COCF₃ |
| 1.85 | F | H | F | CF₃ | H | —COCH₂CF₃ |
| 1.86 | F | H | F | CF₃ | H | —COPh |
| 1.87 | F | H | F | CF³ | H | —CO-3-Cl-Ph |
| 1.88 | F | H | F | CF₃ | H | —CO-3-F-Ph |
| 1.89 | F | H | F | CF₃ | H | —CO-3-NO₂Ph |
| 1.90 | F | H | F | CF₃ | H | —CO-3-SO₂CH₃-Ph |
| 1.91 | F | H | F | CF₃ | H | —CO-3-CF₃-Ph |
| 1.92 | F | H | F | CF₃ | H | —CO-2,4-F₂-Ph |
| 1.93 | F | H | F | CF₃ | H | —CH₂—CF₃ |
| 1.94 | F | H | F | CF₃ | H | —CH₂—CH₂—CF₃ |
| 1.95 | F | H | F | CF₃ | H | —CF₃ |
| 1.96 | F | H | F | CF₃ | H | —CONHCH₃ |
| 1.97 | F | H | F | CF₃ | H | —CONHC₂H₅ |
| 1.98 | F | H | F | CF₃ | H | —CONHⁱPr |
| 1.99 | F | H | F | CF₃ | H | —CONHᵗBu |
| 1.100 | F | H | F | CF₃ | H | —CONH₂ |
| 1.101 | F | H | F | cPr | H | —CH₃ |
| 1.102 | F | H | F | cPr | H | —H |
| 1.103 | F | H | F | cPr | H | —C₂H₅ |
| 1.104 | F | H | F | cPr | H | -ⁱPr |
| 1.105 | F | H | F | cPr | H | -ᵗBu |
| 1.106 | F | H | F | cPr | H | —CH₂OCH₃ |
| 1.107 | F | H | F | cPr | H | —CH₂OC₂H₅ |
| 1.108 | F | H | F | cPr | H | —COOCH₃ |
| 1.109 | F | H | F | cPr | H | —COOC₂H₅ |
| 1.110 | F | H | F | cPr | H | —COOⁱPr |
| 1.111 | F | H | F | cPr | H | —COOᵗBu |
| 1.112 | F | H | F | cPr | H | —COOCF₃ |
| 1.113 | F | H | F | cPr | H | —COOCHF₂ |
| 1.114 | F | H | F | cPr | H | —COOCH₂CF₃ |
| 1.115 | F | H | F | cPr | H | —COOCH₂CHF₂ |
| 1.116 | F | H | F | cPr | H | —COCH₃ |
| 1.117 | F | H | F | cPr | H | —COC₂H₅ |
| 1.118 | F | H | F | cPr | H | —COⁱPr |
| 1.119 | F | H | F | cPr | H | —COᵗBu |
| 1.120 | F | H | F | cPr | H | —COCH₂CN |
| 1.121 | F | H | F | cPr | H | —COCH₂CH₂CN |
| 1.122 | F | H | F | cPr | H | —CH₂COOCH₃ |
| 1.123 | F | H | F | cPr | H | —CH₂COOC₂H₅ |
| 1.124 | F | H | F | cPr | H | —CH₂COOⁱPr |
| 1.125 | F | H | F | cPr | H | -Ph |
| 1.126 | F | H | F | cPr | H | -3-F-Ph |
| 1.127 | F | H | F | cPr | H | -3-NO₂-Ph |
| 1.128 | F | H | F | cPr | H | -3-SO₂Me-Ph |
| 1.129 | F | H | F | cPr | H | -3-F-Ph |
| 1.130 | F | H | F | cPr | H | -3-CF₃-Ph |
| 1.131 | F | H | F | cPr | H | -2,4-F₂-Ph |
| 1.132 | F | H | F | cPr | H | -2-CF₃-Ph |
| 1.133 | F | H | F | cPr | H | -4-CF₃Ph |
| 1.134 | F | H | F | cPr | H | —COCF₃ |
| 1.135 | F | H | F | cPr | H | —COCH₂CF₃ |
| 1.136 | F | H | F | cPr | H | —COPh |
| 1.137 | F | H | F | cPr | H | —CO-3-Cl-Ph |
| 1.138 | F | H | F | cPr | H | —CO-3-F-Ph |
| 1.139 | F | H | F | cPr | H | —CO-3-NO₂Ph |
| 1.140 | F | H | F | cPr | H | —CO-3-SO₂CH₃-Ph |
| 1.141 | F | H | F | cPr | H | —CO-3-CF₃-Ph |
| 1.142 | F | H | F | cPr | H | —CO-2,4-F₂-Ph |
| 1.143 | F | H | F | cPr | H | —CH₂—CF₃ |
| 1.144 | F | H | F | cPr | H | —CH₂—CH₂—CF₃ |
| 1.145 | F | H | F | cPr | H | —CF₃ |
| 1.146 | F | H | F | cPr | H | —CONHCH₃ |
| 1.147 | F | H | F | cPr | H | —CONHC₂H₅ |
| 1.148 | F | H | F | cPr | H | —CONHⁱPr |
| 1.149 | F | H | F | cPr | H | —CONHᵗBu |
| 1.150 | F | H | F | cPr | H | —CONH₂ |

TABLE 1-continued

Ie

[Structure: a phenyl ring with R³ (top), R² (middle-left), R¹ (bottom) substituents, connected to a 2-oxopyridine ring bearing N-R¹¹R¹² (on the pyridine N) and R⁸ at the 4-position]

| No. | R¹ | R² | R³ | R⁸ | R¹² | R¹¹ |
|---|---|---|---|---|---|---|
| 1.151 | H | CF₃ | H | CH₃ | H | —CH₃ |
| 1.152 | H | CF₃ | H | CH₃ | H | —H |
| 1.153 | H | CF₃ | H | CH₃ | H | —C₂H₅ |
| 1.154 | H | CF₃ | H | CH₃ | H | -ⁱPr |
| 1.155 | H | CF₃ | H | CH₃ | H | -ᵗBu |
| 1.156 | H | CF₃ | H | CH₃ | H | —CH₂OCH₃ |
| 1.157 | H | CF₃ | H | CH₃ | H | —CH₂OC₂H₅ |
| 1.158 | H | CF₃ | H | CH₃ | H | —COOCH₃ |
| 1.159 | H | CF₃ | H | CH₃ | H | —COOC₂H₅ |
| 1.160 | H | CF₃ | H | CH₃ | H | —COOⁱPr |
| 1.161 | H | CF₃ | H | CH₃ | H | —COOᵗBu |
| 1.162 | H | CF₃ | H | CH₃ | H | —COOCF₃ |
| 1.163 | H | CF₃ | H | CH₃ | H | —COOCHF₂ |
| 1.164 | H | CF₃ | H | CH₃ | H | —COOCH₂CF₃ |
| 1.165 | H | CF₃ | H | CH₃ | H | —COOCH₂CHF₂ |
| 1.166 | H | CF₃ | H | CH₃ | H | —COCH₃ |
| 1.167 | H | CF₃ | H | CH₃ | H | —COC₂H₅ |
| 1.168 | H | CF₃ | H | CH₃ | H | —COⁱPr |
| 1.169 | H | CF₃ | H | CH₃ | H | —COᵗBu |
| 1.170 | H | CF₃ | H | CH₃ | H | —COCH₂CN |
| 1.171 | H | CF₃ | H | CH₃ | H | —COCH₂CH₂CN |
| 1.172 | H | CF₃ | H | CH₃ | H | —CH₂COOCH₃ |
| 1.173 | H | CF₃ | H | CH₃ | H | —CH₂COOC₂H₅ |
| 1.174 | H | CF₃ | H | CH₃ | H | —CH₂COOⁱPr |
| 1.175 | H | CF₃ | H | CH₃ | H | -Ph |
| 1.176 | H | CF₃ | H | CH₃ | H | -3-F-Ph |
| 1.177 | H | CF₃ | H | CH₃ | H | -3-NO₂-Ph |
| 1.178 | H | CF₃ | H | CH₃ | H | -3-SO₂Me-Ph |
| 1.179 | H | CF₃ | H | CH₃ | H | -3-F-Ph |
| 1.180 | H | CF₃ | H | CH₃ | H | -3-CF₃-Ph |
| 1.181 | H | CF₃ | H | CH₃ | H | -2,4-F₂-Ph |
| 1.182 | H | CF₃ | H | CH₃ | H | -2-CF₃-Ph |
| 1.183 | H | CF₃ | H | CH₃ | H | -4-CF₃Ph |
| 1.184 | H | CF₃ | H | CH₃ | H | —COCF₃ |
| 1.185 | H | CF₃ | H | CH₃ | H | —COCH₂CF₃ |
| 1.186 | H | CF₃ | H | CH₃ | H | —COPh |
| 1.187 | H | CF₃ | H | CH₃ | H | —CO-3-Cl-Ph |
| 1.188 | H | CF₃ | H | CH₃ | H | —CO-3-F-Ph |
| 1.189 | H | CF₃ | H | CH₃ | H | —CO-3-NO₂Ph |
| 1.190 | H | CF₃ | H | CH₃ | H | —CO-3-SO₂CH₃-Ph |
| 1.191 | H | CF₃ | H | CH₃ | H | —CO-3-CF₃-Ph |
| 1.192 | H | CF₃ | H | CH₃ | H | —CO-2,4-F₂-Ph |
| 1.193 | H | CF₃ | H | CH₃ | H | —CH₂—CF₃ |
| 1.194 | H | CF₃ | H | CH₃ | H | —CH₂—CH₂—CF₃ |
| 1.195 | H | CF₃ | H | CH₃ | H | —CF₃ |
| 1.196 | H | CF₃ | H | CH₃ | H | —CONHCH₃ |
| 1.197 | H | CF₃ | H | CH₃ | H | —CONHC₂H₅ |
| 1.198 | H | CF₃ | H | CH₃ | H | —CONHⁱPr |
| 1.199 | H | CF₃ | H | CH₃ | H | —CONHᵗBu |
| 1.200 | H | CF₃ | H | CH₃ | H | —CONH₂ |
| 1.201 | H | CF₃ | H | CF₃ | H | —CH₃ |
| 1.202 | H | CF₃ | H | CF₃ | H | —H |
| 1.203 | H | CF₃ | H | CF₃ | H | —C₂H₅ |
| 1.204 | H | CF₃ | H | CF₃ | H | -ⁱPr |
| 1.205 | H | CF₃ | H | CF₃ | H | -ᵗBu |
| 1.206 | H | CF₃ | H | CF₃ | H | —CH₂OCH₃ |
| 1.207 | H | CF₃ | H | CF₃ | H | —CH₂OC₂H₅ |
| 1.208 | H | CF₃ | H | CF₃ | H | —COOCH₃ |
| 1.209 | H | CF₃ | H | CF₃ | H | —COOC₂H₅ |
| 1.210 | H | CF₃ | H | CF₃ | H | —COOⁱPr |
| 1.211 | H | CF₃ | H | CF₃ | H | —COOᵗBu |
| 1.212 | H | CF₃ | H | CF₃ | H | —COOCF₃ |
| 1.213 | H | CF₃ | H | CF₃ | H | —COOCHF₂ |
| 1.214 | H | CF₃ | H | CF₃ | H | —COOCH₂CF₃ |
| 1.215 | H | CF₃ | H | CF₃ | H | —COOCH₂CHF₂ |
| 1.216 | H | CF₃ | H | CF₃ | H | —COCH₃ |
| 1.217 | H | CF₃ | H | CF₃ | H | —COC₂H₅ |
| 1.218 | H | CF₃ | H | CF₃ | H | —COⁱPr |
| 1.219 | H | CF₃ | H | CF₃ | H | —COᵗBu |
| 1.220 | H | CF₃ | H | CF₃ | H | —COCH₂CN |
| 1.221 | H | CF₃ | H | CF₃ | H | —COCH₂CH₂CN |
| 1.222 | H | CF₃ | H | CF₃ | H | —CH₂COOCH₃ |
| 1.223 | H | CF₃ | H | CF₃ | H | —CH₂COOC₂H₅ |
| 1.224 | H | CF₃ | H | CF₃ | H | —CH₂COOⁱPr |
| 1.225 | H | CF₃ | H | CF₃ | H | -Ph |
| 1.226 | H | CF₃ | H | CF₃ | H | -3-F-Ph |
| 1.227 | H | CF₃ | H | CF₃ | H | -3-NO₂-Ph |
| 1.228 | H | CF₃ | H | CF₃ | H | -3-SO₂Me-Ph |
| 1.229 | H | CF₃ | H | CF₃ | H | -3-F-Ph |
| 1.230 | H | CF₃ | H | CF₃ | H | -3-CF₃-Ph |
| 1.231 | H | CF₃ | H | CF₃ | H | -2,4-F₂-Ph |
| 1.232 | H | CF₃ | H | CF₃ | H | -2-CF₃-Ph |
| 1.233 | H | CF₃ | H | CF₃ | H | -4-CF₃Ph |
| 1.234 | H | CF₃ | H | CF₃ | H | —COCF₃ |
| 1.235 | H | CF₃ | H | CF₃ | H | —COCH₂CF₃ |
| 1.236 | H | CF₃ | H | CF₃ | H | —COPh |
| 1.237 | H | CF₃ | H | CF₃ | H | —CO-3-Cl-Ph |
| 1.238 | H | CF₃ | H | CF₃ | H | —CO-3-F-Ph |
| 1.239 | H | CF₃ | H | CF₃ | H | —CO-3-NO₂Ph |
| 1.240 | H | CF₃ | H | CF₃ | H | —CO-3-SO₂CH₃-Ph |
| 1.241 | H | CF₃ | H | CF₃ | H | —CO-3-CF₃-Ph |
| 1.242 | H | CF₃ | H | CF₃ | H | —CO-2,4-F₂-Ph |
| 1.243 | H | CF₃ | H | CF₃ | H | —CH₂—CF₃ |
| 1.244 | H | CF₃ | H | CF₃ | H | —CH₂—CH₂—CF₃ |
| 1.245 | H | CF₃ | H | CF₃ | H | —CF₃ |
| 1.246 | H | CF₃ | H | CF₃ | H | —CONHCH₃ |
| 1.247 | H | CF₃ | H | CF₃ | H | —CONHC₂H₅ |
| 1.248 | H | CF₃ | H | CF₃ | H | —CONHⁱPr |
| 1.249 | H | CF₃ | H | CF₃ | H | —CONHᵗBu |
| 1.250 | H | CF₃ | H | CF₃ | H | —CONH₂ |
| 1.251 | H | CF₃ | H | cPr | H | —CH₃ |
| 1.252 | H | CF₃ | H | cPr | H | —H |
| 1.253 | H | CF₃ | H | cPr | H | —C₂H₅ |
| 1.254 | H | CF₃ | H | cPr | H | -ⁱPr |
| 1.255 | H | CF₃ | H | cPr | H | -ᵗBu |
| 1.256 | H | CF₃ | H | cPr | H | —CH₂OCH₃ |
| 1.257 | H | CF₃ | H | cPr | H | —CH₂OC₂H₅ |
| 1.258 | H | CF₃ | H | cPr | H | —COOCH₃ |
| 1.259 | H | CF₃ | H | cPr | H | —COOC₂H₅ |
| 1.260 | H | CF₃ | H | cPr | H | —COOⁱPr |
| 1.261 | H | CF₃ | H | cPr | H | —COOᵗBu |
| 1.262 | H | CF₃ | H | cPr | H | —COOCF₃ |
| 1.263 | H | CF₃ | H | cPr | H | —COOCHF₂ |
| 1.264 | H | CF₃ | H | cPr | H | —COOCH₂CF₃ |
| 1.265 | H | CF₃ | H | cPr | H | —COOCH₂CHF₂ |
| 1.266 | H | CF₃ | H | cPr | H | —COCH₃ |
| 1.267 | H | CF₃ | H | cPr | H | —COC₂H₅ |
| 1.268 | H | CF₃ | H | cPr | H | —COⁱPr |
| 1.269 | H | CF₃ | H | cPr | H | —COᵗBu |
| 1.270 | H | CF₃ | H | cPr | H | —COCH₂CN |
| 1.271 | H | CF₃ | H | cPr | H | —COCH₂CH₂CN |
| 1.272 | H | CF₃ | H | cPr | H | —CH₂COOCH₃ |
| 1.273 | H | CF₃ | H | cPr | H | —CH₂COOC₂H₅ |
| 1.274 | H | CF₃ | H | cPr | H | —CH₂COOⁱPr |
| 1.275 | H | CF₃ | H | cPr | H | -Ph |
| 1.276 | H | CF₃ | H | cPr | H | -3-F-Ph |
| 1.277 | H | CF₃ | H | cPr | H | -3-NO₂-Ph |
| 1.278 | H | CF₃ | H | cPr | H | -3-SO₂Me-Ph |

TABLE 1-continued

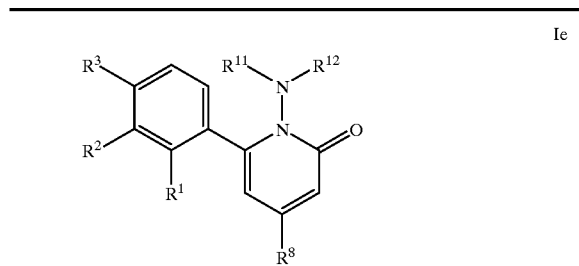

Ie

| No. | R¹ | R² | R³ | R⁸ | R¹² | R¹¹ |
|---|---|---|---|---|---|---|
| 1.279 | H | CF³ | H | cPr | H | -3-F-Ph |
| 1.280 | H | CF₃ | H | cPr | H | -3-CF₃-Ph |
| 1.281 | H | CF₃ | H | cPr | H | -2,4-F₂-Ph |
| 1.282 | H | CF₃ | H | cPr | H | -2-CF₃-Ph |
| 1.283 | H | CF₃ | H | cPr | H | -4-CF₃Ph |
| 1.284 | H | CF₃ | H | cPr | H | —COCF₃ |
| 1.285 | H | CF₃ | H | cPr | H | —COCH₂CF₃ |
| 1.286 | H | CF₃ | H | cPr | H | —COPh |
| 1.287 | H | CF₃ | H | cPr | H | —CO-3-Cl-Ph |
| 1.288 | H | CF₃ | H | cPr | H | —CO-3-F-Ph |
| 1.289 | H | CF₃ | H | cPr | H | —CO-3-NO₂Ph |
| 1.290 | H | CF₃ | H | cPr | H | —CO-3-SO₂CH₃-Ph |
| 1.291 | H | CF₃ | H | cPr | H | —CO-3-CF₃-Ph |
| 1.292 | H | CF₃ | H | cPr | H | —CO-2,4-F₂-Ph |
| 1.293 | H | CF₃ | H | cPr | H | —CH₂—CF₃ |
| 1.294 | H | CF₃ | H | cPr | H | —CH₂—CH₂—CF₃ |
| 1.295 | H | CF₃ | H | cPr | H | —CF₃ |
| 1.296 | H | CF₃ | H | cPr | H | —CONHCH₃ |
| 1.297 | H | CF₃ | H | cPr | H | —CONHC₂H₅ |
| 1.298 | H | CF₃ | H | cPr | H | —CONHⁱPr |
| 1.299 | H | CF₃ | H | cPr | H | —CONHᵗBu |
| 1.300 | H | CF₃ | H | cPr | H | —CONH₂ |
| 1.301 | H | H | H | CH₃ | H | —CH₃ |
| 1.302 | H | H | H | CH₃ | H | —H |
| 1.303 | H | H | H | CH₃ | H | —C₂H₅ |
| 1.304 | H | H | H | CH₃ | H | -ⁱPr |
| 1.305 | H | H | H | CH₃ | H | -ᵗBu |
| 1.306 | H | H | H | CH₃ | H | —CH₂OCH₃ |
| 1.307 | H | H | H | CH₃ | H | —CH₂OC₂H₅ |
| 1.308 | H | H | H | CH₃ | H | —COOCH₃ |
| 1.309 | H | H | H | CH₃ | H | —COOC₂H₅ |
| 1.310 | H | H | H | CH₃ | H | —COOⁱPr |
| 1.311 | H | H | H | CH₃ | H | —COOᵗBu |
| 1.312 | H | H | H | CH₃ | H | —COOCF₃ |
| 1.313 | H | H | H | CH₃ | H | —COOCHF₂ |
| 1.314 | H | H | H | CH₃ | H | —COOCH₂CF₃ |
| 1.315 | H | H | H | CH₃ | H | —COOCH₂CHF₂ |
| 1.316 | H | H | H | CH₃ | H | —COCH₃ |
| 1.317 | H | H | H | CH₃ | H | —COC₂H₅ |
| 1.318 | H | H | H | CH₃ | H | —COⁱPr |
| 1.319 | H | H | H | CH₃ | H | —COᵗBu |
| 1.320 | H | H | H | CH₃ | H | —COCH₂CN |
| 1.321 | H | H | H | CH₃ | H | —COCH₂CH₂CN |
| 1.322 | H | H | H | CH₃ | H | —CH₂COOCH₃ |
| 1.323 | H | H | H | CH₃ | H | —CH₂COOC₂H₅ |
| 1.324 | H | H | H | CH₃ | H | —CH₂COOⁱPr |
| 1.325 | H | H | H | CH₃ | H | -Ph |
| 1.326 | H | H | H | CH₃ | H | -3-F-Ph |
| 1.327 | H | H | H | CH₃ | H | -3-NO₂-Ph |
| 1.328 | H | H | H | CH₃ | H | -3-SO₂Me-Ph |
| 1.329 | H | H | H | CH₃ | H | -3-F-Ph |
| 1.330 | H | H | H | CH₃ | H | -3-CF₃-Ph |
| 1.331 | H | H | H | CH₃ | H | -2,4-F₂-Ph |
| 1.332 | H | H | H | CH₃ | H | -2-CF₃-Ph |
| 1.333 | H | H | H | CH₃ | H | -4-CF₃Ph |
| 1.334 | H | H | H | CH₃ | H | —COCF₃ |
| 1.335 | H | H | H | CH₃ | H | —COCH₂CF₃ |
| 1.336 | H | H | H | CH₃ | H | —COPh |
| 1.337 | H | H | H | CH₃ | H | —CO-3-Cl-Ph |
| 1.338 | H | H | H | CH₃ | H | —CO-3-F-Ph |
| 1.339 | H | H | H | CH₃ | H | —CO-3-NO₂Ph |
| 1.340 | H | H | H | CH₃ | H | —CO-3-SO₂CH₃-Ph |
| 1.341 | H | H | H | CH₃ | H | —CO-3-CF₃-Ph |
| 1.342 | H | H | H | CH₃ | H | —CO-2,4-F₂-Ph |
| 1.343 | H | H | H | CH³ | H | —CH₂—CF₃ |
| 1.344 | H | H | H | CH₃ | H | —CH₂—CH₂—CF₃ |
| 1.345 | H | H | H | CH₃ | H | —CF₃ |
| 1.346 | H | H | H | CH₃ | H | —CONHCH₃ |
| 1.347 | H | H | H | CH₃ | H | —CONHC₂H₅ |
| 1.348 | H | H | H | CH₃ | H | —CONHⁱPr |
| 1.349 | H | H | H | CH₃ | H | —CONHᵗBu |
| 1.350 | H | H | H | CH₃ | H | —CONH₂ |
| 1.351 | H | H | H | CF₃ | H | —CH₃ |
| 1.352 | H | H | H | CF₃ | H | —H |
| 1.353 | H | H | H | CF₃ | H | —C₂H₅ |
| 1.354 | H | H | H | CF₃ | H | -ⁱPr |
| 1.355 | H | H | H | CF₃ | H | -ᵗBu |
| 1.356 | H | H | H | CF₃ | H | —CH₂OCH₃ |
| 1.357 | H | H | H | CF₃ | H | —CH₂OC₂H₅ |
| 1.358 | H | H | H | CF₃ | H | —COOCH₃ |
| 1.359 | H | H | H | CF₃ | H | —COOC₂H₅ |
| 1.360 | H | H | H | CF₃ | H | —COOⁱPr |
| 1.361 | H | H | H | CF₃ | H | —COOᵗBu |
| 1.362 | H | H | H | CF₃ | H | —COOCF₃ |
| 1.363 | H | H | H | CF₃ | H | —COOCHF₂ |
| 1.364 | H | H | H | CF₃ | H | —COOCH₂CF₃ |
| 1.365 | H | H | H | CF₃ | H | —COOCH₂CHF₂ |
| 1.366 | H | H | H | CF₃ | H | —COCH₃ |
| 1.367 | H | H | H | CF₃ | H | —COC₂H₅ |
| 1.368 | H | H | H | CF₃ | H | —COⁱPr |
| 1.369 | H | H | H | CF₃ | H | —COᵗBu |
| 1.370 | H | H | H | CF₃ | H | —COCH₂CN |
| 1.371 | H | H | H | CF₃ | H | —COCH₂CH₂CN |
| 1.372 | H | H | H | CF₃ | H | —CH₂COOCH₃ |
| 1.373 | H | H | H | CF₃ | H | —CH₂COOC₂H₅ |
| 1.374 | H | H | H | CF₃ | H | —CH₂COOⁱPr |
| 1.375 | H | H | H | CF₃ | H | -Ph |
| 1.376 | H | H | H | CF₃ | H | -3-F-Ph |
| 1.377 | H | H | H | CF₃ | H | -3-NO₂-Ph |
| 1.378 | H | H | H | CF₃ | H | -3-SO₂Me-Ph |
| 1.379 | H | H | H | CF₃ | H | -3-F-Ph |
| 1.380 | H | H | H | CF₃ | H | -3-CF₃-Ph |
| 1.381 | H | H | H | CF₃ | H | -2,4-F₂-Ph |
| 1.382 | H | H | H | CF₃ | H | -2-CF₃-Ph |
| 1.383 | H | H | H | CF₃ | H | -4-CF₃Ph |
| 1.384 | H | H | H | CF₃ | H | —COCF₃ |
| 1.385 | H | H | H | CF₃ | H | —COCH₂CF₃ |
| 1.386 | H | H | H | CF₃ | H | —COPh |
| 1.387 | H | H | H | CF₃ | H | —CO-3-Cl-Ph |
| 1.388 | H | H | H | CF₃ | H | —CO-3-F-Ph |
| 1.389 | H | H | H | CF₃ | H | —CO-3-NO₂Ph |
| 1.390 | H | H | H | CF₃ | H | —CO-3-SO₂CH₃-Ph |
| 1.391 | H | H | H | CF₃ | H | —CO-3-CF₃-Ph |
| 1.392 | H | H | H | CF₃ | H | —CO-2,4-F₂-Ph |
| 1.393 | H | H | H | CF₃ | H | —CH₂—CF₃ |
| 1.394 | H | H | H | CF₃ | H | —CH₂—CH₂—CF₃ |
| 1.395 | H | H | H | CF₃ | H | —CF₃ |
| 1.396 | H | H | H | CF₃ | H | —CONHCH₃ |
| 1.397 | H | H | H | CF₃ | H | —CONHC₂H₅ |
| 1.398 | H | H | H | CF₃ | H | —CONHⁱPr |
| 1.399 | H | H | H | CF₃ | H | —CONHᵗBu |
| 1.400 | H | H | H | CF₃ | H | —CONH₂ |
| 1.401 | H | H | H | cPr | H | —CH₃ |
| 1.402 | H | H | H | cPr | H | —H |
| 1.403 | H | H | H | cPr | H | —C₂H₅ |
| 1.404 | H | H | H | cPr | H | -ⁱPr |
| 1.405 | H | H | H | cPr | H | -ᵗBu |
| 1.406 | H | H | H | cPr | H | —CH₂OCH₃ |

TABLE 1-continued

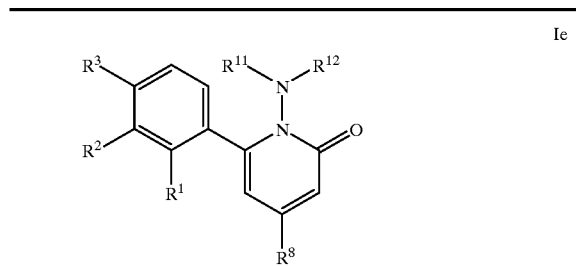

Ie

| No. | R¹ | R² | R³ | R⁸ | R¹² | R¹¹ |
|---|---|---|---|---|---|---|
| 1.407 | H | H | H | cPr | H | —CH₂OC₂H₅ |
| 1.408 | H | H | H | cPr | H | —COOCH₃ |
| 1.409 | H | H | H | cPr | H | —COOC₂H₅ |
| 1.410 | H | H | H | cPr | H | —COOⁱPr |
| 1.411 | H | H | H | cPr | H | —COOCF₃ |
| 1.412 | H | H | H | cPr | H | —COOCHF₂ |
| 1.413 | H | H | H | cPr | H | —COOCH₂CF₃ |
| 1.414 | H | H | H | cPr | H | —COOCH₂CHF₂ |
| 1.415 | H | H | H | cPr | H | —COOᵗBu |
| 1.416 | H | H | H | cPr | H | —COCH₃ |
| 1.417 | H | H | H | cPr | H | —COC₂H₅ |
| 1.418 | H | H | H | cPr | H | —COⁱPr |
| 1.419 | H | H | H | cPr | H | —COᵗBu |
| 1.420 | H | H | H | cPr | H | —COCH₂CN |
| 1.421 | H | H | H | cPr | H | —COCH₂CH₂CN |
| 1.422 | H | H | H | cPr | H | —CH₂COOCH₃ |
| 1.423 | H | H | H | cPr | H | —CH₂COOC₂H₅ |
| 1.424 | H | H | H | cPr | H | —CH₂COOⁱPr |
| 1.425 | H | H | H | cPr | H | -Ph |
| 1.426 | H | H | H | cPr | H | -3-F-Ph |
| 1.427 | H | H | H | cPr | H | -3-NO₂-Ph |
| 1.428 | H | H | H | cPr | H | -3-SO₂Me-Ph |
| 1.429 | H | H | H | cPr | H | -3-F-Ph |
| 1.430 | H | H | H | cPr | H | -3-CF₃-Ph |
| 1.431 | H | H | H | cPr | H | -2,4-F₂-Ph |
| 1.432 | H | H | H | cPr | H | -2-CF₃-Ph |
| 1.433 | H | H | H | cPr | H | -4-CF₃Ph |
| 1.434 | H | H | H | cPr | H | —COCF₃ |
| 1.435 | H | H | H | cPr | H | —COCH₂CF₃ |
| 1.436 | H | H | H | cPr | H | —COPh |
| 1.437 | H | H | H | cPr | H | —CO-3-Cl-Ph |
| 1.438 | H | H | H | cPr | H | —CO-3-F-Ph |
| 1.439 | H | H | H | cPr | H | —CO-3-NO₂Ph |
| 1.440 | H | H | H | cPr | H | —CO-3-SO₂CH₃-Ph |
| 1.441 | H | H | H | cPr | H | —CO-3-CF₃-Ph |
| 1.442 | H | H | H | cPr | H | —CO-2,4-F₂-Ph |
| 1.443 | H | H | H | cPr | H | —CH₂—CF₃ |
| 1.444 | H | H | H | cPr | H | —CH₂—CH₂—CF₃ |
| 1.445 | H | H | H | cPr | H | —CF₃ |
| 1.446 | H | H | H | cPr | H | —CONHCH₃ |
| 1.447 | H | H | H | cPr | H | —CONHC₂H₅ |
| 1.448 | H | H | H | cPr | H | —CONHⁱPr |
| 1.449 | H | H | H | cPr | H | —CONHᵗBu |
| 1.450 | H | H | H | cPr | H | —CONH₂ |
| 1.451 | F | H | F | H | H | —CH₃ |
| 1.452 | F | H | F | H | H | —H |
| 1.453 | F | H | F | H | H | —C₂H₅ |
| 1.454 | F | H | F | H | H | -ⁱPr |
| 1.455 | F | H | F | H | H | -ᵗBu |
| 1.456 | F | H | F | H | H | —CH₂OCH₃ |
| 1.457 | F | H | F | H | H | —CH₂OC₂H₅ |
| 1.458 | F | H | F | H | H | —COOCH₃ |
| 1.459 | F | H | F | H | H | —COOC₂H₅ |
| 1.460 | F | H | F | H | H | —COOⁱPr |
| 1.461 | F | H | F | H | H | —COOᵗBu |
| 1.462 | F | H | F | H | H | —COOCF₃ |
| 1.463 | F | H | F | H | H | —COOCHF₂ |
| 1.464 | F | H | F | H | H | —COOCH₂CF₃ |
| 1.465 | F | H | F | H | H | —COOCH₂F₂ |
| 1.466 | F | H | F | H | H | —COCH₃ |
| 1.467 | F | H | F | H | H | —COC₂H₅ |
| 1.468 | F | H | F | H | H | —COⁱPr |
| 1.469 | F | H | F | H | H | —COᵗBu |
| 1.470 | F | H | F | H | H | —COCH₂CN |
| 1.471 | F | H | F | H | H | —COCH₂CH₂CN |
| 1.472 | F | H | F | H | H | —CH₂COOCH₃ |
| 1.473 | F | H | F | H | H | —CH₂COOC₂H₅ |
| 1.474 | F | H | F | H | H | —CH₂COOⁱPr |
| 1.475 | F | H | F | H | H | -Ph |
| 1.476 | F | H | F | H | H | -3-F-Ph |
| 1.477 | F | H | F | H | H | -3-NO₂-Ph |
| 1.478 | F | H | F | H | H | -3-SO₂Me-Ph |
| 1.479 | F | H | F | H | H | -3-F-Ph |
| 1.480 | F | H | F | H | H | -3-CF₃-Ph |
| 1.481 | F | H | F | H | H | -2,4-F₂-Ph |
| 1.482 | F | H | F | H | H | -2-CF₃-Ph |
| 1.483 | F | H | F | H | H | -4-CF₃Ph |
| 1.484 | F | H | F | H | H | —COCF₃ |
| 1.485 | F | H | F | H | H | —COCH₂CF₃ |
| 1.486 | F | H | F | H | H | —COPh |
| 1.487 | F | H | F | H | H | —CO-3-Cl-Ph |
| 1.488 | F | H | F | H | H | —CO-3-F-Ph |
| 1.489 | F | H | F | H | H | —CO-3-NO₂Ph |
| 1.490 | F | H | F | H | H | —CO-3-SO₂CH₃-Ph |
| 1.491 | F | H | F | H | H | —CO-3-CF₃-Ph |
| 1.492 | F | H | F | H | H | —CO-2,4-F₂-Ph |
| 1.493 | F | H | F | H | H | —CH₂—CF₃ |
| 1.494 | F | H | F | H | H | —CH₂—CH₂—CF₃ |
| 1.495 | F | H | F | H | H | —CF₃ |
| 1.496 | F | H | F | H | H | —CONHCH₃ |
| 1.497 | F | H | F | H | H | —CONHC₂H₅ |
| 1.498 | F | H | F | H | H | —CONHⁱPr |
| 1.499 | F | H | F | H | H | —CONHᵗBu |
| 1.500 | F | H | F | H | H | —CONH₂ |
| 1.501 | H | CF₃ | H | H | H | —CH₃ |
| 1.502 | H | CF₃ | H | H | H | —H |
| 1.503 | H | CF₃ | H | H | H | —C₂H₅ |
| 1.504 | H | CF₃ | H | H | H | -ⁱPr |
| 1.505 | H | CF₃ | H | H | H | -ᵗBu |
| 1.506 | H | CF₃ | H | H | H | —CH₂OCH₃ |
| 1.507 | H | CF₃ | H | H | H | —CH₂OC₂H₅ |
| 1.508 | H | CF₃ | H | H | H | —COOCH₃ |
| 1.509 | H | CF₃ | H | H | H | —COOC₂H₅ |
| 1.510 | H | CF₃ | H | H | H | —COOⁱPr |
| 1.511 | H | CF₃ | H | H | H | —COOᵗBu |
| 1.512 | H | CF₃ | H | H | H | —COOCF₃ |
| 1.513 | H | CF₃ | H | H | H | —COOCHF₂ |
| 1.514 | H | CF₃ | H | H | H | —COOCH₂CF₃ |
| 1.515 | H | CF₃ | H | H | H | —COOCH₂CHF₂ |
| 1.516 | H | CF₃ | H | H | H | —COCH₃ |
| 1.517 | H | CF₃ | H | H | H | —COC₂H₅ |
| 1.518 | H | CF₃ | H | H | H | —COⁱPr |
| 1.519 | H | CF₃ | H | H | H | —COᵗBu |
| 1.520 | H | CF₃ | H | H | H | —COCH₂CN |
| 1.521 | H | CF₃ | H | H | H | —COCH₂CH₂CN |
| 1.522 | H | CF₃ | H | H | H | —CH₂COOCH₃ |
| 1.523 | H | CF₃ | H | H | H | —CH₂COOC₂H₅ |
| 1.524 | H | CF₃ | H | H | H | —CH₂COOⁱPr |
| 1.525 | H | CF₃ | H | H | H | -Ph |
| 1.526 | H | CF₃ | H | H | H | -3-F-Ph |
| 1.527 | H | CF₃ | H | H | H | -3-NO₂-Ph |
| 1.528 | H | CF₃ | H | H | H | -3-SO₂Me-Ph |
| 1.529 | H | CF₃ | H | H | H | -3-F-Ph |
| 1.530 | H | CF₃ | H | H | H | -3-CF₃-Ph |
| 1.531 | H | CF₃ | H | H | H | -2,4-F₂-Ph |
| 1.532 | H | CF₃ | H | H | H | -2-CF₃-Ph |
| 1.533 | H | CF₃ | H | H | H | -4-CF₃Ph |
| 1.534 | H | CF₃ | H | H | H | —COCF₃ |

TABLE 1-continued

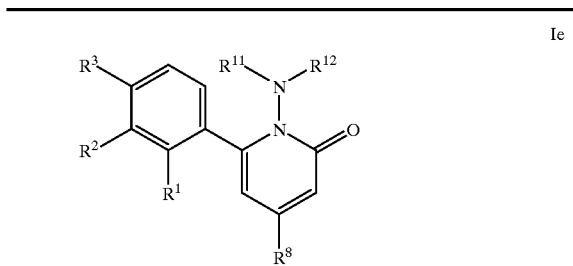

Ie

| No. | R¹ | R² | R³ | R⁸ | R¹² | R¹¹ |
|---|---|---|---|---|---|---|
| 1.535 | H | CF₃ | H | H | H | —COCH₂CF₃ |
| 1.536 | H | CF₃ | H | H | H | —COPh |
| 1.537 | H | CF₃ | H | H | H | —CO-3-Cl-Ph |
| 1.538 | H | CF₃ | H | H | H | —CO-3-F-Ph |
| 1.539 | H | CF₃ | H | H | H | —CO-3-NO₂Ph |
| 1.540 | H | CF₃ | H | H | H | —CO-3-SO₂CH₃-Ph |
| 1.541 | H | CF₃ | H | H | H | —CO-3-CF₃-Ph |
| 1.542 | H | CF₃ | H | H | H | —CO-2,4-F₂-Ph |
| 1.543 | H | CF₃ | H | H | H | —CH₂—CF₃ |
| 1.544 | H | CF₃ | H | H | H | —CH₂—CH₂—CF₃ |
| 1.545 | H | CF₃ | H | H | H | —CF₃ |
| 1.546 | H | CF₃ | H | H | H | —CONHCH₃ |
| 1.547 | H | CF₃ | H | H | H | —CONHC₂H₅ |
| 1.548 | H | CF₃ | H | H | H | —CONHⁱPr |
| 1.549 | H | CF₃ | H | H | H | —CONHᵗBu |
| 1.550 | H | CF₃ | H | H | H | —CONH₂ |
| 1.551 | H | H | H | H | H | —CH₃ |
| 1.552 | H | H | H | H | H | —H |
| 1.553 | H | H | H | H | H | —C₂H₅ |
| 1.554 | H | H | H | H | H | -ⁱPr |
| 1.555 | H | H | H | H | H | -ᵗBu |
| 1.556 | H | H | H | H | H | —CH₂OCH₃ |
| 1.557 | H | H | H | H | H | —CH₂OC₂H₅ |
| 1.558 | H | H | H | H | H | —COOCH₃ |
| 1.559 | H | H | H | H | H | —COOC₂H₅ |
| 1.560 | H | H | H | H | H | —COOⁱPr |
| 1.561 | H | H | H | H | H | —COOᵗBu |
| 1.562 | H | H | H | H | H | —COOCF₃ |
| 1.563 | H | H | H | H | H | —COOCHF₂ |
| 1.564 | H | H | H | H | H | —COOCH₂CF₃ |
| 1.565 | H | H | H | H | H | —COOCH₂CHF₂ |
| 1.566 | H | H | H | H | H | —COCH₃ |
| 1.567 | H | H | H | H | H | —COC₂H₅ |
| 1.568 | H | H | H | H | H | —COⁱPr |
| 1.569 | H | H | H | H | H | —COᵗBu |
| 1.570 | H | H | H | H | H | —COCH₂CN |
| 1.571 | H | H | H | H | H | —COCH₂CH₂CN |
| 1.572 | H | H | H | H | H | —CH₂COOCH₃ |
| 1.573 | H | H | H | H | H | —CH₂COOC₂H₅ |
| 1.574 | H | H | H | H | H | —CH₂COOⁱPr |
| 1.575 | H | H | H | H | H | -Ph |
| 1.576 | H | H | H | H | H | -3-F-Ph |
| 1.577 | H | H | H | H | H | -3-NO₂-Ph |
| 1.578 | H | H | H | H | H | -3-SO₂Me-Ph |
| 1.579 | H | H | H | H | H | -3-F-Ph |
| 1.580 | H | H | H | H | H | -3-CF₃-Ph |
| 1.581 | H | H | H | H | H | -2,4-F₂-Ph |
| 1.582 | H | H | H | H | H | -2-CF₃-Ph |
| 1.583 | H | H | H | H | H | -4-CF₃Ph |
| 1.584 | H | H | H | H | H | —COCF₃ |
| 1.585 | H | H | H | H | H | —COCH₂CF₃ |
| 1.586 | H | H | H | H | H | —COPh |
| 1.587 | H | H | H | H | H | —CO-3-Cl-Ph |
| 1.588 | H | H | H | H | H | —CO-3-F-Ph |
| 1.589 | H | H | H | H | H | —CO-3-NO₂Ph |
| 1.590 | H | H | H | H | H | —CO-3-SO₂CH₃-Ph |
| 1.591 | H | H | H | H | H | —CO-3-CF₃-Ph |
| 1.592 | H | H | H | H | H | —CO-2,4-F₂-Ph |
| 1.593 | H | H | H | H | H | —CH₂—CF₃ |
| 1.594 | H | H | H | H | H | —CH₂—CH₂—CF₃ |
| 1.595 | H | H | H | H | H | —CF₃ |
| 1.596 | H | H | H | H | H | —CONHCH₃ |
| 1.597 | H | H | H | H | H | —CONHC₂H₅ |
| 1.598 | H | H | H | H | H | —CONHⁱPr |
| 1.599 | H | H | H | H | H | —CONHᵗBu |
| 1.600 | H | H | H | H | H | —CONH₂ |
| 1.601 | H | CF₃ | H | CH₃ | H | —COO-cyclohexyl |
| 1.602 | H | CF₃ | H | CH₃ | H | —COOCH₂CCl₃ |
| 1.603 | H | CF₃ | H | CH₃ | H | —COOCH₂CH(CH₃)₂ |
| 1.604 | H | CF₃ | H | CH₃ | H | —COOCH₂CHCH₂ |
| 1.605 | H | CF₃ | H | CH₃ | H | —COOⁿBu |
| 1.606 | H | CF₃ | H | CH₃ | H | —COOCH₂Ph |
| 1.607 | H | CF₃ | H | CH₃ | H | —COOC(=CH₂)CH₃ |
| 1.608 | H | OC₂F₄H | H | CH₃ | H | —COOCH₃ |
| 1.609 | H | OC₂F₄H | H | CH₃ | H | —COOC₂H₅ |
| 1.610 | H | OC₂F₄H | H | CH₃ | H | —COOᵗBu |
| 1.611 | F | H | F | CH₃ | H | —COOCH₂CH(CH₃)₂ |

TABLE 2

Id

| No. | R¹ | R² | R³ | R⁸ | R¹² | R¹¹ |
|---|---|---|---|---|---|---|
| 2.1 | F | H | F | CH₃ | H | —CH₃ |
| 2.2 | F | H | F | CH₃ | H | —H |
| 2.3 | F | H | F | CH₃ | H | —C₂H₅ |
| 2.4 | F | H | F | CH₃ | H | —ⁱPr |
| 2.5 | F | H | F | CH₃ | H | —ᵗBu |
| 2.6 | F | H | F | CH₃ | H | —CH₂OCH₃ |
| 2.7 | F | H | F | CH₃ | H | —CH₂OC₂H₅ |
| 2.8 | F | H | F | CH₃ | H | —COOCH₃ |
| 2.9 | F | H | F | CH₃ | H | —COOC₂H₅ |
| 2.10 | F | H | F | CH₃ | H | —COOⁱPr |
| 2.11 | F | H | F | CH₃ | H | —COOᵗBu |
| 2.12 | F | H | F | CH₃ | H | —COOCF₃ |
| 2.13 | F | H | F | CH₃ | H | —COOCHF₂ |
| 2.14 | F | H | F | CH₃ | H | —COOCH₂CF₃ |
| 2.15 | F | H | F | CH₃ | H | —COOCH₂CHF₂ |
| 2.16 | F | H | F | CH₃ | H | —COCH₃ |
| 2.17 | F | H | F | CH₃ | H | —COC₂H₅ |
| 2.18 | F | H | F | CH₃ | H | —COⁱPr |
| 2.19 | F | H | F | CH₃ | H | —CO₂Bu |
| 2.20 | F | H | F | CH₃ | H | —COCH₂CN |

TABLE 2-continued

![Structure Id with R3, R2, R1 on phenyl, R11, R12 on N-N, R8 on ring]

| No. | R¹ | R² | R³ | R⁸ | R¹² | R¹¹ |
|---|---|---|---|---|---|---|
| 2.21 | F | H | F | CH³ | H | —COCH₂CH₂CN |
| 2.22 | F | H | F | CH₃ | H | —CH₂COOCH₃ |
| 2.23 | F | H | F | CH₃ | H | —CH₂COOC₂H₅ |
| 2.24 | F | H | F | CH₃ | H | —CH₂COOⁱPr |
| 2.25 | F | H | F | CH₃ | H | —Ph |
| 2.26 | F | H | F | CH₃ | H | -3-F—Ph |
| 2.27 | F | H | F | CH₃ | H | -3-NO₂—Ph |
| 2.28 | F | H | F | CH₃ | H | -3-SO₂Me—Ph |
| 2.29 | F | H | F | CH₃ | H | -3-F—Ph |
| 2.30 | F | H | F | CH₃ | H | -3-CF₃—Ph |
| 2.31 | F | H | F | CH₃ | H | -2,4-F₂—Ph |
| 2.32 | F | H | F | CH₃ | H | -2-CF₃—Ph |
| 2.33 | F | H | F | CH₃ | H | -4-CF₃Ph |
| 2.34 | F | H | F | CH₃ | H | —COCF₃ |
| 2.35 | F | H | F | CH₃ | H | —COCH₂CF₃ |
| 2.36 | F | H | F | CH₃ | H | —COPh |
| 2.37 | F | H | F | CH₃ | H | —CO-3-Cl—Ph |
| 2.38 | F | H | F | CH₃ | H | —CO-3-F—Ph |
| 2.39 | F | H | F | CH₃ | H | —CO-3-NO₂Ph |
| 2.40 | F | H | F | CH₃ | H | —CO-3-SO₂CH₃—Ph |
| 2.41 | F | H | F | CH₃ | H | —CO-3-CF₃—Ph |
| 2.42 | F | H | F | CH₃ | H | —CO-2,4-F₂—Ph |
| 2.43 | F | H | F | CH₃ | H | —CH₂—CF₃ |
| 2.44 | F | H | F | CH₃ | H | —CH₂—CH₂—CF₃ |
| 2.45 | F | H | F | CH₃ | H | —CF₃ |
| 2.46 | F | H | F | CH₃ | H | —CONHCH₃ |
| 2.47 | F | H | F | CH₃ | H | —CONHC₂H₅ |
| 2.48 | F | H | F | CH₃ | H | —CONHⁱPr |
| 2.49 | F | H | F | CH₃ | H | —CONHᵗBu |
| 2.50 | F | H | F | CH₃ | H | —CONH₂ |
| 2.51 | F | H | F | CF₃ | H | —CH₃ |
| 2.52 | F | H | F | CF₃ | H | —H |
| 2.53 | F | H | F | CF₃ | H | —C₂H₅ |
| 2.54 | F | H | F | CF₃ | H | —ⁱPr |
| 2.55 | F | H | F | CF₃ | H | —ᵗBu |
| 2.56 | F | H | F | CF₃ | H | —CH₂OCH₃ |
| 2.57 | F | H | F | CF₃ | H | —CH₂OC₂H₅ |
| 2.58 | F | H | F | CF₃ | H | —COOCH₃ |
| 2.59 | F | H | F | CF₃ | H | —COOC₂H₅ |
| 2.60 | F | H | F | CF₃ | H | —COOⁱPr |
| 2.61 | F | H | F | CF₃ | H | —COOᵗBu |
| 2.62 | F | H | F | CF₃ | H | —COOCF₃ |
| 2.63 | F | H | F | CF₃ | H | —COOCHF₂ |
| 2.64 | F | H | F | CF₃ | H | —COOCH₂CF₃ |
| 2.65 | F | H | F | CF₃ | H | —COOCH₂CHF₂ |
| 2.66 | F | H | F | CF₃ | H | —COCH₃ |
| 2.67 | F | H | F | CF₃ | H | —COC₂H₅ |
| 2.68 | F | H | F | CF₃ | H | —COⁱPr |
| 2.69 | F | H | F | CF₃ | H | —COᵗBu |
| 2.70 | F | H | F | CF₃ | H | —COCH₂CN |
| 2.71 | F | H | F | CF₃ | H | —COCH₂CH₂CN |
| 2.72 | F | H | F | CF₃ | H | —CH₂COOCH₃ |
| 2.73 | F | H | F | CF₃ | H | —CH₂COOC₂H₅ |
| 2.74 | F | H | F | CF₃ | H | —CH₂COOⁱPr |
| 2.75 | F | H | F | CF₃ | H | —Ph |
| 2.76 | F | H | F | CF₃ | H | -3-F—Ph |
| 2.77 | F | H | F | CF₃ | H | -3-NO₂—Ph |
| 2.78 | F | H | F | CF₃ | H | -3-SO₂Me—Ph |
| 2.79 | F | H | F | CF₃ | H | -3-F—Ph |
| 2.80 | F | H | F | CF₃ | H | -3-CF₃—Ph |
| 2.81 | F | H | F | CF₃ | H | -2,4-F₂—Ph |
| 2.82 | F | H | F | CF₃ | H | -2-CF₃—Ph |
| 2.83 | F | H | F | CF₃ | H | -4-CF₃Ph |
| 2.84 | F | H | F | CF₃ | H | —COCF₃ |
| 2.85 | F | H | F | CF₃ | H | —COCH₂CF₃ |
| 2.86 | F | H | F | CF₃ | H | —COPh |
| 2.87 | F | H | F | CF₃ | H | —CO-3-Cl—Ph |
| 2.88 | F | H | F | CF₃ | H | —CO-3-F—Ph |
| 2.89 | F | H | F | CF₃ | H | —CO-3-NO₂Ph |
| 2.90 | F | H | F | CF₃ | H | —CO-3-SO₂CH₃—Ph |
| 2.91 | F | H | F | CF₃ | H | —CO-3-CF₃—Ph |
| 2.92 | F | H | F | CF₃ | H | —CO-2,4-F₂—Ph |
| 2.93 | F | H | F | CF₃ | H | —CH₂—CF₃ |
| 2.94 | F | H | F | CF₃ | H | —CH₂—CH₂—CF₃ |
| 2.95 | F | H | F | CF₃ | H | —CF₃ |
| 2.96 | F | H | F | CF₃ | H | —CONHCH₃ |
| 2.97 | F | H | F | CF₃ | H | —CONHC₂H₅ |
| 2.98 | F | H | F | CF₃ | H | —CONHⁱPr |
| 2.99 | F | H | F | CF₃ | H | —CONHᵗBu |
| 2.100 | F | H | F | CF₃ | H | —CONH₂ |
| 2.101 | F | H | F | cPr | H | —CH₃ |
| 2.102 | F | H | F | cPr | H | —H |
| 2.103 | F | H | F | cPr | H | —C₂H₅ |
| 2.104 | F | H | F | cPr | H | —ⁱPr |
| 2.105 | F | H | F | cPr | H | —ᵗBu |
| 2.106 | F | H | F | cPr | H | —CH₂OCH₃ |
| 2.107 | F | H | F | cPr | H | —CH₂OC₂H₅ |
| 2.108 | F | H | F | cPr | H | —COOCH₃ |
| 2.109 | F | H | F | cPr | H | —COOC₂H₅ |
| 2.110 | F | H | F | cPr | H | —COOⁱPr |
| 2.111 | F | H | F | cPr | H | —COOᵗBu |
| 2.112 | F | H | F | cPr | H | —COOCF₃ |
| 2.113 | F | H | F | cPr | H | —COOCHF₂ |
| 2.114 | F | H | F | cPr | H | —COOCH₂CF₃ |
| 2.115 | F | H | F | cPr | H | —COOCH₂CHF₂ |
| 2.116 | F | H | F | cPr | H | —COCH₃ |
| 2.117 | F | H | F | cPr | H | —COC₂H₅ |
| 2.118 | F | H | F | cPr | H | —COⁱPr |
| 2.119 | F | H | F | cPr | H | —COᵗBu |
| 2.120 | F | H | F | cPr | H | —COCH₂CN |
| 2.121 | F | H | F | cPr | H | —COCH₂CH₂CN |
| 2.122 | F | H | F | cPr | H | —CH₂COOCH₃ |
| 2.123 | F | H | F | cPr | H | —CH₂COOC₂H₅ |
| 2.124 | F | H | F | cPr | H | —CH₂COOⁱPr |
| 2.125 | F | H | F | cPr | H | —Ph |
| 2.126 | F | H | F | cPr | H | -3-F—Ph |
| 2.127 | F | H | F | cPr | H | -3-NO₂—Ph |
| 2.128 | F | H | F | cPr | H | -3-SO₂Me—Ph |
| 2.129 | F | H | F | cPr | H | -3-F—Ph |
| 2.130 | F | H | F | cPr | H | -3-CF₃—Ph |
| 2.131 | F | H | F | cPr | H | -2,4-F₂—Ph |
| 2.132 | F | H | F | cPr | H | -2-CF₃—Ph |
| 2.133 | F | H | F | cPr | H | -4-CF₃Ph |
| 2.134 | F | H | F | cPr | H | —COCF₃ |
| 2.135 | F | H | F | cPr | H | —COCH₂CF₃ |
| 2.136 | F | H | F | cPr | H | —COPh |
| 2.137 | F | H | F | cPr | H | —CO-3-Cl—Ph |
| 2.138 | F | H | F | cPr | H | —CO-3-F—Ph |
| 2.139 | F | H | F | cPr | H | —CO-3-NO₂Ph |
| 2.140 | F | H | F | cPr | H | —CO-3-SO₂CH₃—Ph |
| 2.141 | F | H | F | cPr | H | —CO-3-CF₃—Ph |
| 2.142 | F | H | F | cPr | H | —CO-2,4-F₂—Ph |
| 2.143 | F | H | F | cPr | H | —CH₂—CF₃ |
| 2.144 | F | H | F | cPr | H | —CH₂—CH₂—CF₃ |
| 2.145 | F | H | F | cPr | H | —CF₃ |
| 2.146 | F | H | F | cPr | H | —CONHCH₃ |
| 2.147 | F | H | F | cPr | H | —CONHC₂H₅ |
| 2.148 | F | H | F | cPr | H | —CONHⁱPr |

TABLE 2-continued

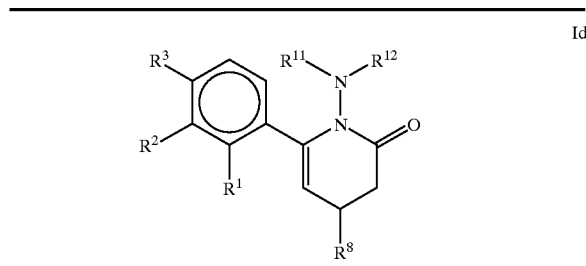

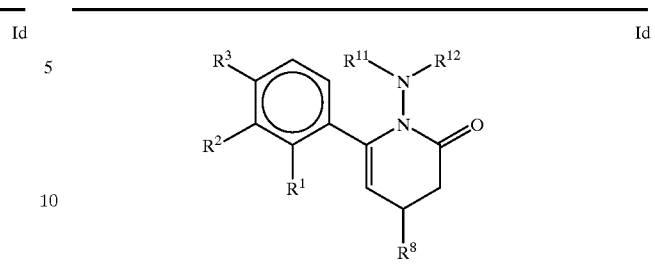

| No. | R¹ | R² | R³ | R⁸ | R¹² | R¹¹ |
|---|---|---|---|---|---|---|
| 2.149 | F | H | F | cPr | H | —CONH$^t$Bu |
| 2.150 | F | H | F | cPr | H | —CONH$_2$ |
| 2.151 | H | CF$_3$ | H | CH$_3$ | H | —CH$_3$ |
| 2.152 | H | CF$_3$ | H | CH$_3$ | H | —H |
| 2.153 | H | CF$_3$ | H | CH$_3$ | H | —C$_2$H$_5$ |
| 2.154 | H | CF$_3$ | H | CH$_3$ | H | —$^i$Pr |
| 2.155 | H | CF$_3$ | H | CH$_3$ | H | —$^t$Bu |
| 2.156 | H | CF$_3$ | H | CH$_3$ | H | —CH$_2$OCH$_3$ |
| 2.157 | H | CF$_3$ | H | CH$_3$ | H | —CH$_2$OC$_2$H$_5$ |
| 2.158 | H | CF$_3$ | H | CH$_3$ | H | —COOCH$_3$ |
| 2.159 | H | CF$_3$ | H | CH$_3$ | H | —COOC$_2$H$_5$ |
| 2.160 | H | CF$_3$ | H | CH$_3$ | H | —COO$^i$Pr |
| 2.161 | H | CF$_3$ | H | CH$_3$ | H | —COO$^t$Bu |
| 2.162 | H | CF$_3$ | H | CH$_3$ | H | —COOCF$_3$ |
| 2.163 | H | CF$_3$ | H | CH$_3$ | H | —COOCHF$_2$ |
| 2.164 | H | CF$_3$ | H | CH$_3$ | H | —COOCH$_2$CF$_3$ |
| 2.165 | H | CF$_3$ | H | CH$_3$ | H | —COOCH$_2$CHF$_2$ |
| 2.166 | H | CF$_3$ | H | CH$_3$ | H | —COCH$_3$ |
| 2.167 | H | CF$_3$ | H | CH$_3$ | H | —COC$_2$H$_5$ |
| 2.168 | H | CF$_3$ | H | CH$_3$ | H | —CO$^i$Pr |
| 2.169 | H | CF$_3$ | H | CH$_3$ | H | —CO$^t$Bu |
| 2.170 | H | CF$_3$ | H | CH$_3$ | H | —COCH$_2$CN |
| 2.171 | H | CF$_3$ | H | CH$_3$ | H | —COCH$_2$CH$_2$CN |
| 2.172 | H | CF$_3$ | H | CH$_3$ | H | —CH$_2$COOCH$_3$ |
| 2.173 | H | CF$_3$ | H | CH$_3$ | H | —CH$_2$COOC$_2$H$_5$ |
| 2.174 | H | CF$_3$ | H | CH$_3$ | H | —CH$_2$COO$^i$Pr |
| 2.175 | H | CF$_3$ | H | CH$_3$ | H | —Ph |
| 2.176 | H | CF$_3$ | H | CH$_3$ | H | -3-F—Ph |
| 2.177 | H | CF$_3$ | H | CH$_3$ | H | -3-NO$_2$—Ph |
| 2.178 | H | CF$_3$ | H | CH$_3$ | H | -3-SO$_2$Me—Ph |
| 2.179 | H | CF$_3$ | H | CH$_3$ | H | -3-F—Ph |
| 2.180 | H | CF$_3$ | H | CH$_3$ | H | -3-CF$_3$—Ph |
| 2.181 | H | CF$_3$ | H | CH$_3$ | H | -2,4-F$_2$—Ph |
| 2.182 | H | CF$_3$ | H | CH$_3$ | H | -2-CF$_3$—Ph |
| 2.183 | H | CF$_3$ | H | CH$_3$ | H | -4-CF$_3$Ph |
| 2.184 | H | CF$_3$ | H | CH$_3$ | H | —COCF$_3$ |
| 2.185 | H | CF$_3$ | H | CH$_3$ | H | —COCH$_2$CF$_3$ |
| 2.186 | H | CF$_3$ | H | CH$_3$ | H | —COPh |
| 2.187 | H | CF$_3$ | H | CH$_3$ | H | —CO-3-Cl—Ph |
| 2.188 | H | CF$_3$ | H | CH$_3$ | H | —CO-3-F—Ph |
| 2.189 | H | CF$_3$ | H | CH$_3$ | H | —CO-3-NO$_2$Ph |
| 2.190 | H | CF$_3$ | H | CH$_3$ | H | —CO-3-SO$_2$CH$_3$—Ph |
| 2.191 | H | CF$_3$ | H | CH$_3$ | H | —CO-3-CF$_3$—Ph |
| 2.192 | H | CF$_3$ | H | CH$_3$ | H | —CO-2,4-F$_2$—Ph |
| 2.193 | H | CF$_3$ | H | CH$_3$ | H | —CH$_2$—CF$_3$ |
| 2.194 | H | CF$_3$ | H | CH$_3$ | H | —CH$_2$—CH$_2$—CF$_3$ |
| 2.195 | H | CF$_3$ | H | CH$_3$ | H | —CF$_3$ |
| 2.196 | H | CF$_3$ | H | CH$_3$ | H | —CONHCH$_3$ |
| 2.197 | H | CF$_3$ | H | CH$_3$ | H | —CONHC$_2$H$_5$ |
| 2.198 | H | CF$_3$ | H | CH$_3$ | H | —CONH$^i$Pr |
| 2.199 | H | CF$_3$ | H | CH$_3$ | H | —CONH$^t$Bu |
| 2.200 | H | CF$_3$ | H | CH$_3$ | H | —CONH$_2$ |
| 2.201 | H | CF$_3$ | H | CF$_3$ | H | —CH$_3$ |
| 2.202 | H | CF$_3$ | H | CF$_3$ | H | —H |
| 2.203 | H | CF$_3$ | H | CF$_3$ | H | —C$_2$H$_5$ |
| 2.204 | H | CF$_3$ | H | CF$_3$ | H | —$^i$Pr |
| 2.205 | H | CF$_3$ | H | CF$_3$ | H | —$^t$Bu |
| 2.206 | H | CF$_3$ | H | CF$_3$ | H | —CH$_2$OCH$_3$ |
| 2.207 | H | CF$_3$ | H | CF$_3$ | H | —CH$_2$OC$_2$H$_5$ |
| 2.208 | H | CF$_3$ | H | CF$_3$ | H | —COOCH$_3$ |
| 2.209 | H | CF$_3$ | H | CF$_3$ | H | —COOC$_2$H$_5$ |
| 2.210 | H | CF$_3$ | H | CF$_3$ | H | —COO$^i$Pr |
| 2.211 | H | CF$_3$ | H | CF$_3$ | H | —COO$^t$Bu |
| 2.212 | H | CF$_3$ | H | CF$_3$ | H | —COOCF$_3$ |
| 2.213 | H | CF$_3$ | H | CF$_3$ | H | —COOCHF$_2$ |
| 2.214 | H | CF$_3$ | H | CF$_3$ | H | —COOCH$_2$CF$_3$ |
| 2.215 | H | CF$_3$ | H | CF$_3$ | H | —COOCH$_2$CHF$_2$ |
| 2.216 | H | CF$_3$ | H | CF$_3$ | H | —COCH$_3$ |
| 2.217 | H | CF$_3$ | H | CF$_3$ | H | —COC$_2$H$_5$ |
| 2.218 | H | CF$_3$ | H | CF$_3$ | H | —CO$^i$Pr |
| 2.219 | H | CF$_3$ | H | CF$_3$ | H | —CO$^t$Bu |
| 2.220 | H | CF$_3$ | H | CF$_3$ | H | —COCH$_2$CN |
| 2.221 | H | CF$_3$ | H | CF$_3$ | H | —COCH$_2$CH$_2$CN |
| 2.222 | H | CF$_3$ | H | CF$_3$ | H | —CH$_2$COOCH$_3$ |
| 2.223 | H | CF$_3$ | H | CF$_3$ | H | —CH$_2$COOC$_2$H$_5$ |
| 2.224 | H | CF$_3$ | H | CF$_3$ | H | —CH$_2$COO$^i$Pr |
| 2.225 | H | CF$_3$ | H | CF$_3$ | H | —Ph |
| 2.226 | H | CF$_3$ | H | CF$_3$ | H | -3-F—Ph |
| 2.227 | H | CF$_3$ | H | CF$_3$ | H | -3-NO$_2$—Ph |
| 2.228 | H | CF$_3$ | H | CF$_3$ | H | -3-SO$_2$Me—Ph |
| 2.229 | H | CF$_3$ | H | CF$_3$ | H | -3-F—Ph |
| 2.230 | H | CF$_3$ | H | CF$_3$ | H | -3-CF$_3$—Ph |
| 2.231 | H | CF$_3$ | H | CF$_3$ | H | -2,4-F$_2$—Ph |
| 2.232 | H | CF$_3$ | H | CF$_3$ | H | -2-CF$_3$—Ph |
| 2.233 | H | CF$_3$ | H | CF$_3$ | H | -4-CF$_3$Ph |
| 2.234 | H | CF$_3$ | H | CF$_3$ | H | —COCF$_3$ |
| 2.235 | H | CF$_3$ | H | CF$_3$ | H | —COCH$_2$CF$_3$ |
| 2.236 | H | CF$_3$ | H | CF$_3$ | H | —COPh |
| 2.237 | H | CF$_3$ | H | CF$_3$ | H | —CO-3-Cl—Ph |
| 2.238 | H | CF$_3$ | H | CF$_3$ | H | —CO-3-F—Ph |
| 2.239 | H | CF$_3$ | H | CF$_3$ | H | —CO-3-NO$_2$Ph |
| 2.240 | H | CF$_3$ | H | CF$_3$ | H | —CO-3-SO$_2$CH$_3$—Ph |
| 2.241 | H | CF$_3$ | H | CF$_3$ | H | —CO-3-CF$_3$—Ph |
| 2.242 | H | CF$_3$ | H | CF$_3$ | H | —CO-2,4-F$_2$—Ph |
| 2.243 | H | CF$_3$ | H | CF$_3$ | H | —CH$_2$—CF$_3$ |
| 2.244 | H | CF$_3$ | H | CF$_3$ | H | —CH$_2$—CH$_2$—CF$_3$ |
| 2.245 | H | CF$_3$ | H | CF$_3$ | H | —CF$_3$ |
| 2.246 | H | CF$_3$ | H | CF$_3$ | H | —CONHCH$_3$ |
| 2.247 | H | CF$_3$ | H | CF$_3$ | H | —CONHC$_2$H$_5$ |
| 2.248 | H | CF$_3$ | H | CF$_3$ | H | —CONH$^i$Pr |
| 2.249 | H | CF$_3$ | H | CF$_3$ | H | —CONH$^t$Bu |
| 2.250 | H | CF$_3$ | H | CF$_3$ | H | —CONH$_2$ |
| 2.251 | H | CF$_3$ | H | cPr | H | —CH$_3$ |
| 2.252 | H | CF$_3$ | H | cPr | H | —H |
| 2.253 | H | CF$_3$ | H | cPr | H | —C$_2$H$_5$ |
| 2.254 | H | CF$_3$ | H | cPr | H | —$^i$Pr |
| 2.255 | H | CF$_3$ | H | cPr | H | —$^t$Bu |
| 2.256 | H | CF$_3$ | H | cPr | H | —CH$_2$OCH$_3$ |
| 2.257 | H | CF$_3$ | H | cPr | H | —CH$_2$OC$_2$H$_5$ |
| 2.258 | H | CF$_3$ | H | cPr | H | —COOCH$_3$ |
| 2.259 | H | CF$_3$ | H | cPr | H | —COOC$_2$H$_5$ |
| 2.260 | H | CF$_3$ | H | cPr | H | —COO$^i$Pr |
| 2.261 | H | CF$_3$ | H | cPr | H | —COO$^t$Bu |
| 2.262 | H | CF$_3$ | H | cPr | H | —COOCF$_3$ |
| 2.263 | H | CF$_3$ | H | cPr | H | —COOCHF$_2$ |
| 2.264 | H | CF$_3$ | H | cPr | H | —COOCH$_2$CF$_3$ |
| 2.265 | H | CF$_3$ | H | cPr | H | —COOCH$_2$CHF$_2$ |
| 2.266 | H | CF$_3$ | H | cPr | H | —COCH$_3$ |
| 2.267 | H | CF$_3$ | H | cPr | H | —COC$_2$H$_5$ |
| 2.268 | H | CF$_3$ | H | cPr | H | —CO$^i$Pr |
| 2.269 | H | CF$_3$ | H | cPr | H | —CO$^t$Bu |
| 2.270 | H | CF$_3$ | H | cPr | H | —COCH$_2$CN |
| 2.271 | H | CF$_3$ | H | cPr | H | —COCH$_2$CH$_2$CN |
| 2.272 | H | CF$_3$ | H | cPr | H | —CH$_2$COOCH$_3$ |
| 2.273 | H | CF$_3$ | H | cPr | H | —CH$_2$COOC$_2$H$_5$ |
| 2.274 | H | CF$_3$ | H | cPr | H | —CH$_2$COO$^i$Pr |
| 2.275 | H | CF$_3$ | H | cPr | H | —Ph |
| 2.276 | H | CF$_3$ | H | cPr | H | -3-F—Ph |

TABLE 2-continued

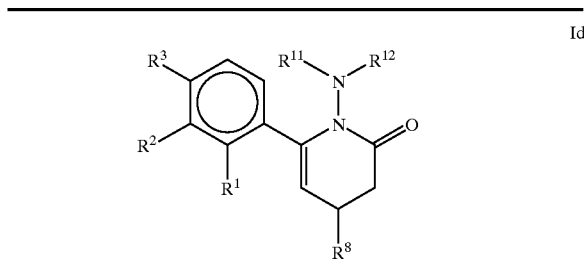

Id

| No. | R¹ | R² | R³ | R⁸ | R¹² | R¹¹ |
|---|---|---|---|---|---|---|
| 2.277 | H | CF³ | H | cPr | H | -3-NO₂—Ph |
| 2.278 | H | CF₃ | H | cPr | H | -3-SO₂Me—Ph |
| 2.279 | H | CF₃ | H | cPr | H | -3-F—Ph |
| 2.280 | H | CF₃ | H | cPr | H | -3-CF₃—Ph |
| 2.281 | H | CF₃ | H | cPr | H | -2,4-F₂—Ph |
| 2.282 | H | CF₃ | H | cPr | H | -2-CF₃—Ph |
| 2.283 | H | CF₃ | H | cPr | H | -4-CF₃Ph |
| 2.284 | H | CF₃ | H | cPr | H | —COCF₃ |
| 2.285 | H | CF₃ | H | cPr | H | —COCH₂CF₃ |
| 2.286 | H | CF₃ | H | cPr | H | —COPh |
| 2.287 | H | CF₃ | H | cPr | H | —CO-3-Cl—Ph |
| 2.288 | H | CF₃ | H | cPr | H | —CO-3-F—Ph |
| 2.289 | H | CF₃ | H | cPr | H | —CO-3-NO₂Ph |
| 2.290 | H | CF₃ | H | cPr | H | —CO-3-SO₂CH₃—Ph |
| 2.291 | H | CF₃ | H | cPr | H | —CO-3-CF₃—Ph |
| 2.292 | H | CF₃ | H | cPr | H | —CO-2,4-F₂—Ph |
| 2.293 | H | CF₃ | H | cPr | H | —CH₂—CF₃ |
| 2.294 | H | CF₃ | H | cPr | H | —CH₂—CH₂—CF₃ |
| 2.295 | H | CF₃ | H | cPr | H | —CF₃ |
| 2.296 | H | CF₃ | H | cPr | H | —CONHCH₃ |
| 2.297 | H | CF₃ | H | cPr | H | —CONHC₂H₅ |
| 2.298 | H | CF₃ | H | cPr | H | —CONHⁱPr |
| 2.299 | H | CF₃ | H | cPr | H | —CONHᵗBu |
| 2.300 | H | CF₃ | H | cPr | H | —CONH₂ |
| 2.301 | H | H | H | CH₃ | H | —CH₃ |
| 2.302 | H | H | H | CH₃ | H | —H |
| 2.303 | H | H | H | CH₃ | H | —C₂H₅ |
| 2.304 | H | H | H | CH₃ | H | —ⁱPr |
| 2.305 | H | H | H | CH₃ | H | —ᵗBu |
| 2.306 | H | H | H | CH₃ | H | —CH₂OCH₃ |
| 2.307 | H | H | H | CH₃ | H | —CH₂OC₂H₅ |
| 2.308 | H | H | H | CH₃ | H | —COOCH₃ |
| 2.309 | H | H | H | CH₃ | H | —COOC₂H₅ |
| 2.310 | H | H | H | CH₃ | H | —COOⁱPr |
| 2.311 | H | H | H | CH₃ | H | —COOᵗBu |
| 2.312 | H | H | H | CH₃ | H | —COOCF₃ |
| 2.313 | H | H | H | CH₃ | H | —COOCHF₂ |
| 2.314 | H | H | H | CH₃ | H | —COOCH₂CF₃ |
| 2.315 | H | H | H | CH₃ | H | —COOCH₂CHF₂ |
| 2.316 | H | H | H | CH₃ | H | —COCH₃ |
| 2.317 | H | H | H | CH₃ | H | —COC₂H₅ |
| 2.318 | H | H | H | CH₃ | H | —COⁱPr |
| 2.319 | H | H | H | CH₃ | H | —COᵗBu |
| 2.320 | H | H | H | CH₃ | H | —COCH₂CN |
| 2.321 | H | H | H | CH₃ | H | —COCH₂CH₂CN |
| 2.322 | H | H | H | CH₃ | H | —CH₂COOCH₃ |
| 2.323 | H | H | H | CH₃ | H | —CH₂COOC₂H₅ |
| 2.324 | H | H | H | CH₃ | H | —CH₂COOⁱPr |
| 2.325 | H | H | H | CH₃ | H | —Ph |
| 2.326 | H | H | H | CH₃ | H | -3-F—Ph |
| 2.327 | H | H | H | CH₃ | H | -3-NO₂—Ph |
| 2.328 | H | H | H | CH₃ | H | -3-SO₂Me—Ph |
| 2.329 | H | H | H | CH₃ | H | -3-F—Ph |
| 2.330 | H | H | H | CH₃ | H | -3-CF₃—Ph |
| 2.331 | H | H | H | CH₃ | H | -2,4-F₂—Ph |
| 2.332 | H | H | H | CH₃ | H | -2-CF₃—Ph |
| 2.333 | H | H | H | CH₃ | H | -4-CF₃Ph |
| 2.334 | H | H | H | CH₃ | H | —COCF₃ |
| 2.335 | H | H | H | CH₃ | H | —COCH₂CF₃ |
| 2.336 | H | H | H | CH₃ | H | —COPh |
| 2.337 | H | H | H | CH₃ | H | —CO-3-Cl—Ph |
| 2.338 | H | H | H | CH₃ | H | —CO-3-F—Ph |
| 2.339 | H | H | H | CH₃ | H | —CO-3-NO₂Ph |
| 2.340 | H | H | H | CH₃ | H | —CO-3-SO₂CH₃—Ph |
| 2.341 | H | H | H | CH³ | H | —CO-3-CF₃—Ph |
| 2.342 | H | H | H | CH₃ | H | —CO-2,4-F₂—Ph |
| 2.343 | H | H | H | CH₃ | H | —CH₂—CF₃ |
| 2.344 | H | H | H | CH₃ | H | —CH₂—CH₂—CF₃ |
| 2.345 | H | H | H | CH₃ | H | —CF₃ |
| 2.346 | H | H | H | CH₃ | H | —CONHCH₃ |
| 2.347 | H | H | H | CH₃ | H | —CONHC₂H₅ |
| 2.348 | H | H | H | CH₃ | H | —CONHⁱPr |
| 2.349 | H | H | H | CH₃ | H | —CONHᵗBu |
| 2.350 | H | H | H | CH₃ | H | —CONH₂ |
| 2.351 | H | H | H | CF₃ | H | —CH₃ |
| 2.352 | H | H | H | CF₃ | H | —H |
| 2.353 | H | H | H | CF₃ | H | —C₂H₅ |
| 2.354 | H | H | H | CF₃ | H | —ⁱPr |
| 2.355 | H | H | H | CF₃ | H | —ᵗBu |
| 2.356 | H | H | H | CF₃ | H | —CH₂OCH₃ |
| 2.357 | H | H | H | CF₃ | H | —CH₂OC₂H₅ |
| 2.358 | H | H | H | CF₃ | H | —COOCH₃ |
| 2.359 | H | H | H | CF₃ | H | —COOC₂H₅ |
| 2.360 | H | H | H | CF₃ | H | —COOⁱPr |
| 2.361 | H | H | H | CF₃ | H | —COOᵗBu |
| 2.362 | H | H | H | CF₃ | H | —COOCF₃ |
| 2.363 | H | H | H | CF₃ | H | —COOCHF₂ |
| 2.364 | H | H | H | CF₃ | H | —COOCH₂CF₃ |
| 2.365 | H | H | H | CF₃ | H | —COOCH₂CHF₂ |
| 2.366 | H | H | H | CF₃ | H | —COCH₃ |
| 2.367 | H | H | H | CF₃ | H | —COC₂H₅ |
| 2.368 | H | H | H | CF₃ | H | —COⁱPr |
| 2.369 | H | H | H | CF₃ | H | —COᵗBu |
| 2.370 | H | H | H | CF₃ | H | —COCH₂CN |
| 2.371 | H | H | H | CF₃ | H | —COCH₂CH₂CN |
| 2.372 | H | H | H | CF₃ | H | —CH₂COOCH₃ |
| 2.373 | H | H | H | CF₃ | H | —CH₂COOC₂H₅ |
| 2.374 | H | H | H | CF₃ | H | —CH₂COOⁱPr |
| 2.375 | H | H | H | CF₃ | H | —Ph |
| 2.376 | H | H | H | CF₃ | H | -3-F—Ph |
| 2.377 | H | H | H | CF₃ | H | -3-NO₂—Ph |
| 2.378 | H | H | H | CF₃ | H | -3-SO₂Me—Ph |
| 2.379 | H | H | H | CF₃ | H | -3-F—Ph |
| 2.380 | H | H | H | CF₃ | H | -3-CF₃—Ph |
| 2.381 | H | H | H | CF₃ | H | -2,4-F₂—Ph |
| 2.382 | H | H | H | CF₃ | H | -2-CF₃—Ph |
| 2.383 | H | H | H | CF₃ | H | -4-CF₃Ph |
| 2.384 | H | H | H | CF₃ | H | —COCF₃ |
| 2.385 | H | H | H | CF₃ | H | —COCH₂CF₃ |
| 2.386 | H | H | H | CF₃ | H | —COPh |
| 2.387 | H | H | H | CF₃ | H | —CO-3-Cl—Ph |
| 2.388 | H | H | H | CF₃ | H | —CO-3-F—Ph |
| 2.389 | H | H | H | CF₃ | H | —CO-3-NO₂Ph |
| 2.390 | H | H | H | CF₃ | H | —CO-3-SO₂CH₃—Ph |
| 2.391 | H | H | H | CF₃ | H | —CO-3-CF₃—Ph |
| 2.392 | H | H | H | CF₃ | H | —CO-2,4-F₂—Ph |
| 2.393 | H | H | H | CF₃ | H | —CH₂—CF₃ |
| 2.394 | H | H | H | CF₃ | H | —CH₂—CH₂—CF₃ |
| 2.395 | H | H | H | CF₃ | H | —CF₃ |
| 2.396 | H | H | H | CF₃ | H | —CONHCH₃ |
| 2.397 | H | H | H | CF₃ | H | —CONHC₂H₅ |
| 2.398 | H | H | H | CF₃ | H | —CONHⁱPr |
| 2.399 | H | H | H | CF₃ | H | —CONHᵗBu |
| 2.400 | H | H | H | CF₃ | H | —CONH₂ |
| 2.401 | H | H | H | cPr | H | —CH₃ |
| 2.402 | H | H | H | cPr | H | —H |
| 2.403 | H | H | H | cPr | H | —C₂H₅ |
| 2.404 | H | H | H | cPr | H | —ⁱPr |

TABLE 2-continued

Id (structure: phenyl with R3, R2, R1 substituents connected to a pyridinone ring bearing N-NR11R12 and R8 substituent)

| No. | R¹ | R² | R³ | R⁸ | R¹² | R¹¹ |
|---|---|---|---|---|---|---|
| 2.405 | H | H | H | cPr | H | —ᵗBu |
| 2.406 | H | H | H | cPr | H | —CH₂OCH₃ |
| 2.407 | H | H | H | cPr | H | —CH₂OC₂H₅ |
| 2.408 | H | H | H | cPr | H | —COOCH₃ |
| 2.409 | H | H | H | cPr | H | —COOC₂H₅ |
| 2.410 | H | H | H | cPr | H | —COOⁱPr |
| 2.411 | H | H | H | cPr | H | —COOᵗBu |
| 2.412 | H | H | H | cPr | H | —COOCF₃ |
| 2.413 | H | H | H | cPr | H | —COOCHF₂ |
| 2.414 | H | H | H | cPr | H | —COOCH₂CF₃ |
| 2.415 | H | H | H | cPr | H | —COOCH₂CHF₂ |
| 2.416 | H | H | H | cPr | H | —COCH₃ |
| 2.417 | H | H | H | cPr | H | —COC₂H₅ |
| 2.418 | H | H | H | cPr | H | —COⁱPr |
| 2.419 | H | H | H | cPr | H | —COᵗBu |
| 2.420 | H | H | H | cPr | H | —COCH₂CN |
| 2.421 | H | H | H | cPr | H | —COCH₂CH₂CN |
| 2.422 | H | H | H | cPr | H | —CH₂COOCH₃ |
| 2.423 | H | H | H | cPr | H | —CH₂COOC₂H₅ |
| 2.424 | H | H | H | cPr | H | —CH₂COOⁱPr |
| 2.425 | H | H | H | cPr | H | —Ph |
| 2.426 | H | H | H | cPr | H | -3-F—Ph |
| 2.427 | H | H | H | cPr | H | -3-NO₂—Ph |
| 2.428 | H | H | H | cPr | H | -3-SO₂Me—Ph |
| 2.429 | H | H | H | cPr | H | -3-F—Ph |
| 2.430 | H | H | H | cPr | H | -3-CF₃—Ph |
| 2.431 | H | H | H | cPr | H | -2,4-F₂—Ph |
| 2.432 | H | H | H | cPr | H | -2-CF₃—Ph |
| 2.433 | H | H | H | cPr | H | -4-CF₃Ph |
| 2.434 | H | H | H | cPr | H | —COCF₃ |
| 2.435 | H | H | H | cPr | H | —COCH₂CF₃ |
| 2.436 | H | H | H | cPr | H | —COPh |
| 2.437 | H | H | H | cPr | H | —CO-3-Cl—Ph |
| 2.438 | H | H | H | cPr | H | —CO-3-F—Ph |
| 2.439 | H | H | H | cPr | H | —CO-3-NO₂Ph |
| 2.440 | H | H | H | cPr | H | —CO-3-SO₂CH₃—Ph |
| 2.441 | H | H | H | cPr | H | —CO-3-CF₃—Ph |
| 2.442 | H | H | H | cPr | H | —CO-2,4-F₂—Ph |
| 2.443 | H | H | H | cPr | H | —CH₂—CF₃ |
| 2.444 | H | H | H | cPr | H | —CH₂—CH₂—CF₃ |
| 2.445 | H | H | H | cPr | H | —CF₃ |
| 2.446 | H | H | H | cPr | H | —CONHCH₃ |
| 2.447 | H | H | H | cPr | H | —CONHC₂H₅ |
| 2.448 | H | H | H | cPr | H | —CONHⁱPr |
| 2.449 | H | H | H | cPr | H | —CONHᵗBu |
| 2.450 | H | H | H | cPr | H | —CONH₂ |
| 2.451 | F | H | F | H | H | —CH₃ |
| 2.452 | F | H | F | H | H | —H |
| 2.453 | F | H | F | H | H | —C₂H₅ |
| 2.454 | F | H | F | H | H | —ⁱPr |
| 2.455 | F | H | F | H | H | —ᵗBu |
| 2.456 | F | H | F | H | H | —CH₂OCH₃ |
| 2.457 | F | H | F | H | H | —CH₂OC₂H₅ |
| 2.458 | F | H | F | H | H | —COOCH₃ |
| 2.459 | F | H | F | H | H | —COOC₂H₅ |
| 2.460 | F | H | F | H | H | —COOⁱPr |
| 2.461 | F | H | F | H | H | —COOᵗBu |
| 2.462 | F | H | F | H | H | —COOCF₃ |
| 2.463 | F | H | F | H | H | —COOCHF₂ |
| 2.464 | F | H | F | H | H | —COOCH₂CF₃ |
| 2.465 | F | H | F | H | H | —COOCH₂CHF₂ |
| 2.466 | F | H | F | H | H | —COCH₃ |
| 2.467 | F | H | F | H | H | —COC₂H₅ |
| 2.468 | F | H | F | H | H | —COⁱPr |
| 2.469 | F | H | F | H | H | —COᵗBu |
| 2.470 | F | H | F | H | H | —COCH₂CN |
| 2.471 | F | H | F | H | H | —COCH₂CH₂CN |
| 2.472 | F | H | F | H | H | —CH₂COOCH₃ |
| 2.473 | F | H | F | H | H | —CH₂COOC₂H₅ |
| 2.474 | F | H | F | H | H | —CH₂COOⁱPr |
| 2.475 | F | H | F | H | H | —Ph |
| 2.476 | F | H | F | H | H | -3-F—Ph |
| 2.477 | F | H | F | H | H | -3-NO₂—Ph |
| 2.478 | F | H | F | H | H | -3-SO₂Me—Ph |
| 2.479 | F | H | F | H | H | -3-F—Ph |
| 2.480 | F | H | F | H | H | -3-CF₃—Ph |
| 2.481 | F | H | F | H | H | -2,4-F₂—Ph |
| 2.482 | F | H | F | H | H | -2-CF₃—Ph |
| 2.483 | F | H | F | H | H | -4-CF₃Ph |
| 2.484 | F | H | F | H | H | —COCF₃ |
| 2.485 | F | H | F | H | H | —COCH₂CF₃ |
| 2.486 | F | H | F | H | H | —COPh |
| 2.487 | F | H | F | H | H | —CO-3-Cl—Ph |
| 2.488 | F | H | F | H | H | —CO-3-F—Ph |
| 2.489 | F | H | F | H | H | —CO-3-NO₂Ph |
| 2.490 | F | H | F | H | H | —CO-3-SO₂CH₃—Ph |
| 2.491 | F | H | F | H | H | —CO-3-CF₃—Ph |
| 2.492 | F | H | F | H | H | —CO-2,4-F₂—Ph |
| 2.493 | F | H | F | H | H | —CH₂—CF₃ |
| 2.494 | F | H | F | H | H | —CH₂—CH₂—CF₃ |
| 2.495 | F | H | F | H | H | —CF₃ |
| 2.496 | F | H | F | H | H | —CONHCH₃ |
| 2.497 | F | H | F | H | H | —CONHC₂H₅ |
| 2.498 | F | H | F | H | H | —CONHⁱPr |
| 2.499 | F | H | F | H | H | —CONHᵗBu |
| 2.500 | F | H | F | H | H | —CONH₂ |
| 2.501 | H | CF₃ | H | H | H | —CH₃ |
| 2.502 | H | CF₃ | H | H | H | —H |
| 2.503 | H | CF₃ | H | H | H | —C₂H₅ |
| 2.504 | H | CF₃ | H | H | H | —ⁱPr |
| 2.505 | H | CF₃ | H | H | H | —ᵗBu |
| 2.506 | H | CF₃ | H | H | H | —CH₂OCH₃ |
| 2.507 | H | CF₃ | H | H | H | —CH₂OC₂H₅ |
| 2.508 | H | CF₃ | H | H | H | —COOCH₃ |
| 2.509 | H | CF₃ | H | H | H | —COOC₂H₅ |
| 2.510 | H | CF₃ | H | H | H | —COOⁱPr |
| 2.511 | H | CF₃ | H | H | H | —COOᵗBu |
| 2.512 | H | CF₃ | H | H | H | —COOCF₃ |
| 2.513 | H | CF₃ | H | H | H | —COOCHF₂ |
| 2.514 | H | CF₃ | H | H | H | —COOCH₂CF₃ |
| 2.515 | H | CF₃ | H | H | H | —COOCH₂CHF₂ |
| 2.516 | H | CF₃ | H | H | H | —COCH₃ |
| 2.517 | H | CF₃ | H | H | H | —COC₂H₅ |
| 2.518 | H | CF₃ | H | H | H | —COⁱPr |
| 2.519 | H | CF₃ | H | H | H | —COᵗBu |
| 2.520 | H | CF₃ | H | H | H | —COCH₂CN |
| 2.521 | H | CF₃ | H | H | H | —COCH₂CH₂CN |
| 2.522 | H | CF₃ | H | H | H | —CH₂COOCH₃ |
| 2.523 | H | CF₃ | H | H | H | —CH₂COOC₂H₅ |
| 2.524 | H | CF₃ | H | H | H | —CH₂COOⁱPr |
| 2.525 | H | CF₃ | H | H | H | —Ph |
| 2.526 | H | CF₃ | H | H | H | -3-F—Ph |
| 2.527 | H | CF₃ | H | H | H | -3-NO₂—Ph |
| 2.528 | H | CF₃ | H | H | H | -3-SO₂Me—Ph |
| 2.529 | H | CF₃ | H | H | H | -3-F—Ph |
| 2.530 | H | CF₃ | H | H | H | -3-CF₃—Ph |
| 2.531 | H | CF₃ | H | H | H | -2,4-F₂—Ph |
| 2.532 | H | CF₃ | H | H | H | -2-CF₃—Ph |

TABLE 2-continued

Structure Id: 6-(substituted phenyl)-1-(N,N-disubstituted amino)-4-R8-3,4-dihydro-2(1H)-pyridinone with R1, R2, R3 on phenyl and R11, R12 on nitrogen.

| No. | R1 | R2 | R3 | R8 | R12 | R11 |
|---|---|---|---|---|---|---|
| 2.533 | H | CF3 | H | H | H | -4-CF3Ph |
| 2.534 | H | CF3 | H | H | H | —COCF3 |
| 2.535 | H | CF3 | H | H | H | —COCH2CF3 |
| 2.536 | H | CF3 | H | H | H | —COPh |
| 2.537 | H | CF3 | H | H | H | —CO-3-Cl—Ph |
| 2.538 | H | CF3 | H | H | H | —CO-3-F—Ph |
| 2.539 | H | CF3 | H | H | H | —CO-3-NO2Ph |
| 2.540 | H | CF3 | H | H | H | —CO-3-SO2CH3—Ph |
| 2.541 | H | CF3 | H | H | H | —CO-3-CF3—Ph |
| 2.542 | H | CF3 | H | H | H | —CO-2,4-F2—Ph |
| 2.543 | H | CF3 | H | H | H | —CH2—CF3 |
| 2.544 | H | CF3 | H | H | H | —CH2—CH2—CF3 |
| 2.545 | H | CF3 | H | H | H | —CF3 |
| 2.546 | H | CF3 | H | H | H | —CONHCH3 |
| 2.547 | H | CF3 | H | H | H | —CONHC2H5 |
| 2.548 | H | CF3 | H | H | H | —CONHiPr |
| 2.549 | H | CF3 | H | H | H | —CONHtBu |
| 2.550 | H | CF3 | H | H | H | —CONH2 |
| 2.551 | H | H | H | H | H | —CH3 |
| 2.552 | H | H | H | H | H | —H |
| 2.553 | H | H | H | H | H | —C2H5 |
| 2.554 | H | H | H | H | H | —iPr |
| 2.555 | H | H | H | H | H | —tBu |
| 2.556 | H | H | H | H | H | —CH2OCH3 |
| 2.557 | H | H | H | H | H | —CH2OC2H5 |
| 2.558 | H | H | H | H | H | —COOCH3 |
| 2.559 | H | H | H | H | H | —COOC2H5 |
| 2.560 | H | H | H | H | H | —COOiPr |
| 2.561 | H | H | H | H | H | —COOtBu |
| 2.562 | H | H | H | H | H | —COOCF3 |
| 2.563 | H | H | H | H | H | —COOCHF2 |
| 2.564 | H | H | H | H | H | —COOCH2CF3 |
| 2.565 | H | H | H | H | H | —COOCH2CHF2 |
| 2.566 | H | H | H | H | H | —COCH3 |
| 2.567 | H | H | H | H | H | —COC2H5 |
| 2.568 | H | H | H | H | H | —COiPr |
| 2.569 | H | H | H | H | H | —COtBu |
| 2.570 | H | H | H | H | H | —COCH2CN |
| 2.571 | H | H | H | H | H | —COCH2CH2CN |
| 2.572 | H | H | H | H | H | —CH2COOCH3 |
| 2.573 | H | H | H | H | H | —CH2COOC2H5 |
| 2.574 | H | H | H | H | H | —CH2COOiPr |
| 2.575 | H | H | H | H | H | —Ph |
| 2.576 | H | H | H | H | H | -3-F—Ph |
| 2.577 | H | H | H | H | H | -3-NO2—Ph |
| 2.578 | H | H | H | H | H | -3-SO2Me—Ph |
| 2.579 | H | H | H | H | H | -3-F—Ph |
| 2.580 | H | H | H | H | H | -3-CF3—Ph |
| 2.581 | H | H | H | H | H | -2,4-F2—Ph |
| 2.582 | H | H | H | H | H | -2-CF3—Ph |
| 2.583 | H | H | H | H | H | -4-CF3Ph |
| 2.584 | H | H | H | H | H | —COCF3 |
| 2.585 | H | H | H | H | H | —COCH2CF3 |
| 2.586 | H | H | H | H | H | —COPh |
| 2.587 | H | H | H | H | H | —CO-3-Cl—Ph |
| 2.588 | H | H | H | H | H | —CO-3-F—Ph |
| 2.589 | H | H | H | H | H | —CO-3-NO2Ph |
| 2.590 | H | H | H | H | H | —CO-3-SO2CH3—Ph |
| 2.591 | H | H | H | H | H | —CO-3-CF3—Ph |
| 2.592 | H | H | H | H | H | —CO-2,4-F2—Ph |
| 2.593 | H | H | H | H | H | —CH2—CF3 |
| 2.594 | H | H | H | H | H | —CH2—CH2—CF3 |
| 2.595 | H | H | H | H | H | —CF3 |
| 2.596 | H | H | H | H | H | —CONHCH3 |
| 2.597 | H | H | H | H | H | —CONHC2H5 |
| 2.598 | H | H | H | H | H | —CONHiPr |
| 2.599 | H | H | H | H | H | —CONHtBu |
| 2.600 | H | H | H | H | H | —CONH2 |
| 2.601 | H | CF3 | H | CH3 | H | —COnC4H9 |
| 2.602 | H | CF3 | H | CH3 | H | —CO-3,4-Cl2Ph |
| 2.603 | H | CF3 | H | CH3 | H | —CO-4-CH3Ph |
| 2.604 | H | CF3 | H | CH3 | H | —CO-4-FPh |
| 2.605 | H | OC2F4H | H | CH3 | H | —COOCH3 |
| 2.606 | H | OC2F4H | H | CH3 | H | —COOC2H5 |
| 2.607 | H | OC2F4H | H | CH3 | H | —COOtBu |

TABLE 3

Structure Ih: 6-(2,2-difluoro-1,3-benzodioxol-4-yl)-1-(N,N-disubstituted amino)-4-R8-3,4-dihydro-2(1H)-pyridinone.

| No. | R8 | R12 | R11 |
|---|---|---|---|
| 3.1 | CH3 | H | —CH3 |
| 3.2 | CH3 | H | —H |
| 3.3 | CH3 | H | —C2H5 |
| 3.4 | CH3 | H | —iPr |
| 3.5 | CH3 | H | —tBu |
| 3.6 | CH3 | H | —CH2OCH3 |
| 3.7 | CH3 | H | —CH2OC2H5 |
| 3.8 | CH3 | H | —COOCH3 |
| 3.9 | CH3 | H | —COOC2H5 |
| 3.10 | CH3 | H | —COOiPr |
| 3.11 | CH3 | H | —COOtBu |
| 3.12 | CH3 | H | —COOCF3 |
| 3.13 | CH3 | H | —COOCHF2 |
| 3.14 | CH3 | H | —COOCH2CF3 |
| 3.15 | CH3 | H | —COOCH2CHF2 |
| 3.16 | CH3 | H | —COCH3 |
| 3.17 | CH3 | H | —COC2H5 |
| 3.18 | CH3 | H | —COiPr |
| 3.19 | CH3 | H | —COtBu |
| 3.20 | CH3 | H | —COCH2CN |
| 3.21 | CH3 | H | —CH2COOCH3 |
| 3.22 | CH3 | H | —CH2COOC2H5 |
| 3.23 | CH3 | H | —CH2COOiPr |
| 3.24 | CH3 | H | —Ph |
| 3.25 | CH3 | H | -3-F—Ph |
| 3.26 | CH3 | H | -3-NO2—Ph |
| 3.27 | CH3 | H | -3-SO2Me—Ph |
| 3.28 | CH3 | H | -3-F—Ph |
| 3.29 | CH3 | H | -3-CF3—Ph |
| 3.30 | CH3 | H | -2,4-F2—Ph |
| 3.31 | CH3 | H | -4-CF3Ph |
| 3.32 | CH3 | H | —COCF3 |
| 3.33 | CH3 | H | —COCH2CF3 |

TABLE 3-continued

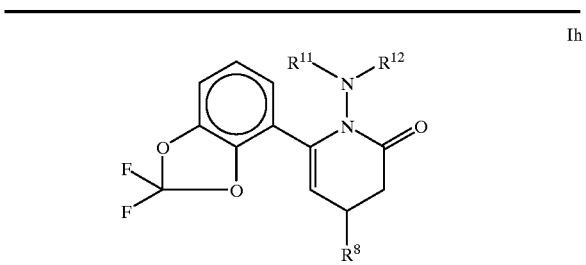

Ih

| No. | R⁸ | R¹² | R¹¹ |
|---|---|---|---|
| 3.34 | CH₃ | H | —COPh |
| 3.35 | CH₃ | H | —CO-3-Cl—Ph |
| 3.36 | CH₃ | H | —CO-3-F—Ph |
| 3.37 | CH₃ | H | —CO-3-NO₂Ph |
| 3.38 | CH₃ | H | —CO-3-CF₃—Ph |
| 3.39 | CH₃ | H | —CO-2,4-F₂—Ph |
| 3.40 | CH₃ | H | —CH₂—CF₃ |
| 3.41 | CH₃ | H | —CH₂—CH₂—CF₃ |
| 3.42 | CH₃ | H | —CF₃ |
| 3.43 | CH₃ | H | —CONHCH₃ |
| 3.44 | CH₃ | H | —CONHC₂H₅ |
| 3.45 | CH₃ | H | —CONHⁱPr |
| 3.46 | CH₃ | H | —CONHᵗBu |
| 3.47 | CH₃ | H | —CONH₂ |
| 3.48 | CF₃ | H | —CH₃ |
| 3.49 | CF₃ | H | —H |
| 3.50 | CF₃ | H | —C₂H₅ |
| 3.51 | CF₃ | H | —ⁱPr |
| 3.52 | CF₃ | H | —ᵗBu |
| 3.53 | CF₃ | H | —CH₂OCH₃ |
| 3.54 | CF₃ | H | —CH₂OC₂H₅ |
| 3.55 | CF₃ | H | —COOCH₃ |
| 3.56 | CF₃ | H | —COOC₂H₅ |
| 3.57 | CF₃ | H | —COOⁱPr |
| 3.58 | CF₃ | H | —COOᵗBu |
| 3.59 | CF₃ | H | —COOCF₃ |
| 3.60 | CF₃ | H | —COOCHF₂ |
| 3.61 | CF₃ | H | —COOCH₂CF₃ |
| 3.62 | CF₃ | H | —COOCH₂CHF₂ |
| 3.63 | CF₃ | H | —COCH₃ |
| 3.64 | CF₃ | H | —COC₂H₅ |
| 3.65 | CF₃ | H | —COⁱPr |
| 3.66 | CF₃ | H | —COCH₂CN |
| 3.67 | CF₃ | H | —COCH₂CH₂CN |
| 3.68 | CF₃ | H | —CH₂COOCH₃ |
| 3.69 | CF₃ | H | —CH₂COOC₂H₅ |
| 3.70 | CF₃ | H | —CH₂COOⁱPr |
| 3.71 | CF₃ | H | —Ph |
| 3.72 | CF₃ | H | -3-F—Ph |
| 3.73 | CF₃ | H | -3-NO₂—Ph |
| 3.74 | CF₃ | H | -3-SO₂Me—Ph |
| 3.75 | CF₃ | H | -3-F—Ph |
| 3.76 | CF₃ | H | -3-CF₃—Ph |
| 3.77 | CF₃ | H | -2,4-F₂—Ph |
| 3.78 | CF₃ | H | -2-CF₃—Ph |
| 3.79 | CF₃ | H | -4-CF₃Ph |
| 3.80 | CF₃ | H | —COCF₃ |
| 3.81 | CF₃ | H | —COCH₂CF₃ |
| 3.82 | CF₃ | H | —COPh |
| 3.83 | CF₃ | H | —CO-3-Cl—Ph |
| 3.84 | CF₃ | H | —CO-3-F—Ph |
| 3.85 | CF₃ | H | —CO-3-NO₂Ph |
| 3.86 | CF₃ | H | —CO-3-CF₃—Ph |
| 3.87 | CF₃ | H | —CO-2,4-F₂—Ph |
| 3.88 | CF₃ | H | —CH₂—CF₃ |
| 3.89 | CF₃ | H | —CH₂—CH₂—CF₃ |
| 3.90 | CF₃ | H | —CF₃ |
| 3.91 | CF₃ | H | —CONHCH₃ |
| 3.92 | CF₃ | H | —CONHC₂H₅ |
| 3.93 | CF₃ | H | —CONHⁱPr |
| 3.94 | CF₃ | H | —CONHᵗBu |
| 3.95 | CF₃ | H | —CONH₂ |
| 3.96 | cPr | H | —CH₃ |
| 3.97 | cPr | H | —H |
| 3.98 | cPr | H | —C₂H₅ |
| 3.99 | cPr | H | —ⁱPr |
| 3.100 | cPr | H | —ᵗBu |
| 3.101 | cPr | H | —CH₂OCH₃ |
| 3.102 | cPr | H | —CH₂OC₂H₅ |
| 3.103 | cPr | H | —COOCH₃ |
| 3.104 | cPr | H | —COOC₂H₅ |
| 3.105 | cPr | H | —COOⁱPr |
| 3.106 | cPr | H | —COOᵗBu |
| 3.107 | cPr | H | —COOCF₃ |
| 3.108 | cPr | H | —COOCHF₂ |
| 3.109 | cPr | H | —COOCH₂CF₃ |
| 3.110 | cPr | H | —COOCH₂CHF₂ |
| 3.111 | cPr | H | —COCH₃ |
| 3.112 | cPr | H | —COC₂H₅ |
| 3.113 | cPr | H | —COⁱPr |
| 3.114 | cPr | H | —COᵗBu |
| 3.115 | cPr | H | —COCH₂CN |
| 3.116 | cPr | H | —COCH₂CH₂CN |
| 3.117 | cPr | H | —CH₂COOCH₃ |
| 3.118 | cPr | H | —CH₂COOC₂H₅ |
| 3.119 | cPr | H | —CH₂COOⁱPr |
| 3.120 | cPr | H | —Ph |
| 3.121 | cPr | H | -3-F—Ph |
| 3.122 | cPr | H | -3-NO₂—Ph |
| 3.123 | cPr | H | -3-SO₂Me—Ph |
| 3.124 | cPr | H | -3-F—Ph |
| 3.125 | cPr | H | -3-CF₃—Ph |
| 3.126 | cPr | H | -2,4-F₂—Ph |
| 3.127 | cPr | H | -2-CF₃—Ph |
| 3.128 | cPr | H | -4-CF₃Ph |
| 3.129 | cPr | H | —COCF₃ |
| 3.130 | cPr | H | —COCH₂CF₃ |
| 3.131 | cPr | H | —COPh |
| 3.132 | cPr | H | —CO-3-Cl—Ph |
| 3.133 | cPr | H | —CO-3-F—Ph |
| 3.134 | cPr | H | —CO-3-NO₂Ph |
| 3.135 | cPr | H | —CO-3-SO₂CH₃—Ph |
| 3.136 | cPr | H | —CO-3-CF₃—Ph |
| 3.137 | cPr | H | —CO-2,4-F₂—Ph |
| 3.138 | cPr | H | —CH₂—CF₃ |
| 3.139 | cPr | H | —CF₃ |
| 3.140 | cPr | H | —CONHCH₃ |
| 3.141 | cPr | H | —CONHC₂H₅ |
| 3.142 | cPr | H | —CONHⁱPr |
| 3.143 | cPr | H | —CONHᵗBu |
| 3.144 | cPr | H | —CONH₂ |
| 3.145 | H | H | —CH₃ |
| 3.146 | H | H | —H |
| 3.147 | H | H | —C₂H₅ |
| 3.148 | H | H | —ⁱPr |
| 3.149 | H | H | —ᵗBu |
| 3.150 | H | H | —CH₂OCH₃ |
| 3.151 | H | H | —CH₂OC₂H₅ |
| 3.152 | H | H | —COOCH₃ |
| 3.153 | H | H | —COOC₂H₅ |
| 3.154 | H | H | —COOⁱPr |
| 3.155 | H | H | —COOᵗBu |
| 3.156 | H | H | —COOCF₃ |
| 3.157 | H | H | —COOCHF₂ |
| 3.158 | H | H | —COOCH₂CF₃ |
| 3.159 | H | H | —COOCH₂CHF₂ |
| 3.160 | H | H | —COCH₃ |
| 3.161 | H | H | —COC₂H₅ |

TABLE 3-continued

Ih: structure with difluoro-benzodioxole connected to pyridinone bearing $R^{11}R^{12}N$— and $R^8$ substituents (dihydropyridinone)

| No. | $R^8$ | $R^{12}$ | $R^{11}$ |
|---|---|---|---|
| 3.162 | H | H | —CO$^i$Pr |
| 3.163 | H | H | —CO$^t$Bu |
| 3.164 | H | H | —COCH$_2$CN |
| 3.165 | H | H | —CH$_2$COOCH$_3$ |
| 3.166 | H | H | —CH$_2$COOC$_2$H$_5$ |
| 3.167 | H | H | —CH$_2$COO$^i$Pr |
| 3.168 | H | H | —Ph |
| 3.169 | H | H | -3-F—Ph |
| 3.170 | H | H | -3-NO$_2$—Ph |
| 3.171 | H | H | -3-SO$_2$Me—Ph |
| 3.172 | H | H | -3-F—Ph |
| 3.173 | H | H | -3-CF$_3$—Ph |
| 3.174 | H | H | -2,4-F$_2$—Ph |
| 3.175 | H | H | -4-CF$_3$Ph |
| 3.176 | H | H | —COCF$_3$ |
| 3.177 | H | H | —COCH$_2$CF$_3$ |
| 3.178 | H | H | —COPh |
| 3.179 | H | H | —CO-3-Cl—Ph |
| 3.180 | H | H | —CO-3-F—Ph |
| 3.181 | H | H | —CO-3-NO$_2$Ph |
| 3.182 | H | H | —CO-3-CF$_3$—Ph |
| 3.183 | H | H | —CO-2,4-F$_2$—Ph |
| 3.184 | H | H | —CH$_2$—CF$_3$ |
| 3.185 | H | H | —CH$_2$—CH$_2$—CF$_3$ |
| 3.186 | H | H | —CF$_3$ |
| 3.187 | H | H | —CONHCH$_3$ |
| 3.188 | H | H | —CONHC$_2$H$_5$ |
| 3.189 | H | H | —CONH$^i$Pr |
| 3.190 | H | H | —CONH$^t$Bu |
| 3.191 | H | H | —CONH$_2$ |

TABLE 4

Ii: structure with difluoro-benzodioxole connected to pyridinone bearing $R^{11}R^{12}N$— and $R^8$ substituents (pyridinone)

| No. | $R^8$ | $R^{12}$ | $R^{11}$ |
|---|---|---|---|
| 4.1 | CH$_3$ | H | —CH$_3$ |
| 4.2 | CH$_3$ | H | —H |
| 4.3 | CH$_3$ | H | —C$_2$H$_5$ |
| 4.4 | CH$_3$ | H | —$^i$Pr |
| 4.5 | CH$_3$ | H | —$^t$Bu |
| 4.6 | CH$_3$ | H | —CH$_2$OCH$_3$ |
| 4.7 | CH$_3$ | H | —CH$_2$OC$_2$H$_5$ |
| 4.8 | CH$_3$ | H | —COOCH$_3$ |
| 4.9 | CH$_3$ | H | —COOC$_2$H$_5$ |
| 4.10 | CH$_3$ | H | —COO$^i$Pr |
| 4.11 | CH$_3$ | H | —COO$^t$Bu |
| 4.12 | CH$_3$ | H | —COOCF$_3$ |
| 4.13 | CH$_3$ | H | —COOCHF$_2$ |
| 4.14 | CH$_3$ | H | —COOCH$_2$CF$_3$ |
| 4.15 | CH$_3$ | H | —COOCH$_2$CHF$_2$ |
| 4.16 | CH$_3$ | H | —COCH$_3$ |
| 4.17 | CH$_3$ | H | —COC$_2$H$_5$ |
| 4.18 | CH$_3$ | H | —CO$^i$Pr |
| 4.19 | CH$_3$ | H | —CO$^t$Bu |
| 4.20 | CH$_3$ | H | —COCH$_2$CN |
| 4.21 | CH$_3$ | H | —CH$_2$COOCH$_3$ |
| 4.22 | CH$_3$ | H | —CH$_2$COOC$_2$H$_5$ |
| 4.23 | CH$_3$ | H | —CH$_2$COO$^i$Pr |
| 4.24 | CH$_3$ | H | —Ph |
| 4.25 | CH$_3$ | H | -3-F—Ph |
| 4.26 | CH$_3$ | H | -3-NO$_2$—Ph |
| 4.27 | CH$_3$ | H | -3-SO$_2$Me—Ph |
| 4.28 | CH$_3$ | H | -3-F—Ph |
| 4.29 | CH$_3$ | H | -3-CF$_3$—Ph |
| 4.30 | CH$_3$ | H | -2,4-F$_2$—Ph |
| 4.31 | CH$_3$ | H | -4-CF$_3$Ph |
| 4.32 | CH$_3$ | H | —COCF$_3$ |
| 4.33 | CH$_3$ | H | —COCH$_2$CF$_3$ |
| 4.34 | CH$_3$ | H | —COPh |
| 4.35 | CH$_3$ | H | —CO-3-Cl—Ph |
| 4.36 | CH$_3$ | H | —CO-3-F—Ph |
| 4.37 | CH$_3$ | H | —CO-3-NO$_2$Ph |
| 4.38 | CH$_3$ | H | —CO-3-CF$_3$—Ph |
| 4.39 | CH$_3$ | H | —CO-2,4-F$_2$—Ph |
| 4.40 | CH$_3$ | H | —CH$_2$—CF$_3$ |
| 4.41 | CH$_3$ | H | —CH$_2$—CH$_2$—CF$_3$ |
| 4.42 | CH$_3$ | H | —CF$_3$ |
| 4.43 | CH$_3$ | H | —CONHCH$_3$ |
| 4.44 | CH$_3$ | H | —CONHC$_2$H$_5$ |
| 4.45 | CH$_3$ | H | —CONH$^i$Pr |
| 4.46 | CH$_3$ | H | —CONH$^t$Bu |
| 4.47 | CH$_3$ | H | —CONH$_2$ |
| 4.48 | CF$_3$ | H | —CH$_3$ |
| 4.49 | CF$_3$ | H | —H |
| 4.50 | CF$_3$ | H | —C$_2$H$_5$ |
| 4.51 | CF$_3$ | H | —$^i$Pr |
| 4.52 | CF$_3$ | H | —$^t$Bu |
| 4.53 | CF$_3$ | H | —CH$_2$OCH$_3$ |
| 4.54 | CF$_3$ | H | —CH$_2$OC$_2$H$_5$ |
| 4.55 | CF$_3$ | H | —COOCH$_3$ |
| 4.56 | CF$_3$ | H | —COOC$_2$H$_5$ |
| 4.57 | CF$_3$ | H | —COO$^i$Pr |
| 4.58 | CF$_3$ | H | —COO$^t$Bu |
| 4.59 | CF$_3$ | H | —COOCF$_3$ |
| 4.60 | CF$_3$ | H | —COOCHF$_2$ |
| 4.61 | CF$_3$ | H | —COOCH$_2$CF$_3$ |
| 4.62 | CF$_3$ | H | —COOCH$_2$CHF$_2$ |
| 4.63 | CF$_3$ | H | —COCH$_3$ |
| 4.64 | CF$_3$ | H | —COC$_2$H$_5$ |
| 4.65 | CF$_3$ | H | —CO$^i$Pr |
| 4.66 | CF$_3$ | H | —COCH$_2$CN |
| 4.67 | CF$_3$ | H | —COCH$_2$CH$_2$CN |
| 4.68 | CF$_3$ | H | —CH$_2$COOCH$_3$ |
| 4.69 | CF$_3$ | H | —CH$_2$COOC$_2$H$_5$ |
| 4.70 | CF$_3$ | H | —CH$_2$COO$^i$Pr |
| 4.71 | CF$_3$ | H | —Ph |
| 4.72 | CF$_3$ | H | -3-F—Ph |
| 4.73 | CF$_3$ | H | -3-NO$_2$—Ph |
| 4.74 | CF$_3$ | H | -3-SO$_2$Me—Ph |
| 4.75 | CF$_3$ | H | -3-F—Ph |
| 4.76 | CF$_3$ | H | -3-CF$_3$—Ph |
| 4.77 | CF$_3$ | H | -2,4-F$_2$—Ph |
| 4.78 | CF$_3$ | H | -2-CF$_3$—Ph |

TABLE 4-continued

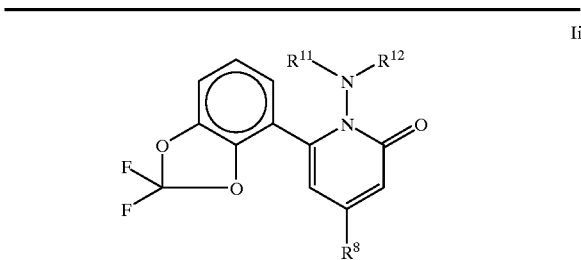

| No. | R⁸ | R¹² | R¹¹ |
|---|---|---|---|
| 4.79 | CF³ | H | -4-CF₃Ph |
| 4.80 | CF₃ | H | —COCF₃ |
| 4.81 | CF₃ | H | —COCH₂CF₃ |
| 4.82 | CF₃ | H | —COPh |
| 4.83 | CF₃ | H | —CO-3-Cl—Ph |
| 4.84 | CF₃ | H | —CO-3-F—Ph |
| 4.85 | CF₃ | H | —CO-3-NO₂Ph |
| 4.86 | CF₃ | H | —CO-3-CF₃—Ph |
| 4.87 | CF₃ | H | —CO-2,4-F₂—Ph |
| 4.88 | CF₃ | H | —CH₂—CF₃ |
| 4.89 | CF₃ | H | —CH₂—CH₂—CF₃ |
| 4.90 | CF₃ | H | —CF₃ |
| 4.91 | CF₃ | H | —CONHCH₃ |
| 4.92 | CF₃ | H | —CONHC₂H₅ |
| 4.93 | CF₃ | H | —CONHⁱPr |
| 4.94 | CF₃ | H | —CONHᵗBu |
| 4.95 | CF₃ | H | —CONH₂ |
| 4.96 | cPr | H | —CH₃ |
| 4.97 | cPr | H | —H |
| 4.98 | cPr | H | —C₂H₅ |
| 4.99 | cPr | H | —ⁱPr |
| 4.100 | cPr | H | —ᵗBu |
| 4.101 | cPr | H | —CH₂OCH₃ |
| 4.102 | cPr | H | —CH₂OC₂H₅ |
| 4.103 | cPr | H | —COOCH₃ |
| 4.104 | cPr | H | —COOC₂H₅ |
| 4.105 | cPr | H | —COOⁱPr |
| 4.106 | cPr | H | —COOᵗBu |
| 4.107 | CF₃ | H | —COOCF₃ |
| 4.108 | CF₃ | H | —COOCHF₂ |
| 4.109 | CF₃ | H | —COOCH₂CF₃ |
| 4.110 | CF₃ | H | —COOCH₂CHF₂ |
| 4.111 | cPr | H | —COCH₃ |
| 4.112 | cPr | H | —COC₂H₅ |
| 4.113 | cPr | H | —COⁱPr |
| 4.114 | cPr | H | —COᵗBu |
| 4.115 | cPr | H | —COCH₂CN |
| 4.116 | cPr | H | —COCH₂CH₂CN |
| 4.117 | cPr | H | —CH₂COOCH₃ |
| 4.118 | cPr | H | —CH₂COOC₂H₅ |
| 4.119 | cPr | H | —CH₂COOⁱPr |
| 4.120 | cPr | H | —Ph |
| 4.121 | cPr | H | -3-F—Ph |
| 4.122 | cPr | H | -3-NO₂—Ph |
| 4.123 | cPr | H | -3-SO₂Me—Ph |
| 4.124 | cPr | H | -3-F—Ph |
| 4.125 | cPr | H | -3-CF₃—Ph |
| 4.126 | cPr | H | -2,4-F₂—Ph |
| 4.127 | cPr | H | -2-CF₃—Ph |
| 4.128 | cPr | H | -4-CF₃Ph |
| 4.129 | cPr | H | —COCF₃ |
| 4.130 | cPr | H | —COCH₂CF₃ |
| 4.131 | cPr | H | —COPh |
| 4.132 | cPr | H | —CO-3-Cl—Ph |
| 4.133 | cPr | H | —CO-3-F—Ph |
| 4.134 | cPr | H | —CO-3-NO₂Ph |
| 4.135 | cPr | H | —CO-3-SO₂CH₃—Ph |
| 4.136 | cPr | H | —CO-3-CF₃—Ph |
| 4.137 | cPr | H | —CO-2,4-F₂—Ph |
| 4.138 | cPr | H | —CH₂—CF₃ |
| 4.139 | cPr | H | —CF₃ |
| 4.140 | cPr | H | —CONHCH₃ |
| 4.141 | cPr | H | —CONHC₂H₅ |
| 4.142 | cPr | H | —CONHⁱPr |

TABLE 4-continued

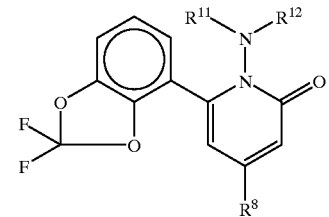

| No. | R⁸ | R¹² | R¹¹ |
|---|---|---|---|
| 4.143 | cPr | H | —CONHᵗBu |
| 4.144 | cPr | H | —CONH₂ |
| 4.145 | H | H | —CH₃ |
| 4.146 | H | H | —H |
| 4.147 | H | H | —C₂H₅ |
| 4.148 | H | H | —ⁱPr |
| 4.149 | H | H | —ᵗBu |
| 4.150 | H | H | —CH₂OCH₃ |
| 4.151 | H | H | —CH₂OC₂H₅ |
| 4.152 | H | H | —COOCH₃ |
| 4.153 | H | H | —COOC₂H₅ |
| 4.154 | H | H | —COOⁱPr |
| 4.155 | H | H | —COOᵗBu |
| 4.156 | H | H | —COOCF₃ |
| 4.157 | H | H | —COOCHF₂ |
| 4.158 | H | H | —COOCH₂CF₃ |
| 4.159 | H | H | —COOCH₂CHF₂ |
| 4.160 | H | H | —COCH₃ |
| 4.161 | H | H | —COC₂H₅ |
| 4.162 | H | H | —COⁱPr |
| 4.163 | H | H | —COᵗBu |
| 4.164 | H | H | —COCH₂CN |
| 4.165 | H | H | —CH₂COOCH₃ |
| 4.166 | H | H | —CH₂COOC₂H₅ |
| 4.167 | H | H | —CH₂COOⁱPr |
| 4.168 | H | H | —Ph |
| 4.169 | H | H | -3-F—Ph |
| 4.170 | H | H | -3-NO₂—Ph |
| 4.171 | H | H | -3-SO₂Me—Ph |
| 4.172 | H | H | -3-F—Ph |
| 4.173 | H | H | -3-CF₃—Ph |
| 4.174 | H | H | -2,4-F₂—Ph |
| 4.175 | H | H | -4-CF₃Ph |
| 4.176 | H | H | —COCF₃ |
| 4.177 | H | H | —COCH₂CF₃ |
| 4.178 | H | H | —COPh |
| 4.179 | H | H | —CO-3-Cl—Ph |
| 4.180 | H | H | —CO-3-F—Ph |
| 4.181 | H | H | —CO-3-NO₂Ph |
| 4.182 | H | H | —CO-3-CF₃—Ph |
| 4.183 | H | H | —CO-2,4-F₂—Ph |
| 4.184 | H | H | —CH₂—CF₃ |
| 4.185 | H | H | —CH₂—CH₂—CF₃ |
| 4.186 | H | H | —CF₃ |
| 4.187 | H | H | —CONHCH₃ |
| 4.188 | H | H | —CONHC₂H₅ |
| 4.189 | H | H | —CONHⁱPr |
| 4.190 | H | H | —CONHᵗBu |
| 4.191 | H | H | —CONH₂ |

EXAMPLES

The preparation of some compounds which are provided by the present invention is described in the following text:

Example 1

5-Keto-3-methyl-5(3'trifluoromethylphenyl)pentanoic acid IIIa

A few drops of 3-trifluoromethylbromobenzene are added to a suspension of 0.72 g (0.03 mol) of magnesium filings and catalytic amounts of iodine in 10 ml of dry diethyl ether. After the solution has been heated using a hairdryer until the red color of the iodine has disappeared, a solution of 6.75 g (0.03 mol) of trifluoromethylbromobenzene in 50 ml of dry diethyl ether is slowly added dropwise. When all of the magnesium has reacted, the Grignard complex prepared is slowly added dropwise to a solution of 3.84 g (0.03 mol) of 3-methylglutaric anhydride in 80 ml of dry diethyl ether. The solution is refluxed for 4 hours and subsequently stirred overnight. For working-up, the reaction solution is poured into $H_2O$ and acidified by adding dilute HCl to destroy the Grignard complex. The pH of the aqueous phase is subsequently brought to 10 using semi-concentrated NaOH and washed three times using diethyl ether. After the aqueous phase has been acidified using concentrated HCl, the desired product is obtained by extracting the mixture three times using diethyl ether and subsequently drying the organic phases over $Na_2SO_4$.

Yield: 6.1 g $^1$H NMR (300 MHz, $CDCl_3$) δ in ppm: 1.12(d); 2.47(m); 2.73(m); 2.94(AB); 3.20(AB); 7.63(t); 7.84(d); 8.18(d); 8.26 (s); 9.37(br.).

Example 2

1-(Ethoxycarbonyl)amino-3,4-dihydro-4-methyl-6-(3'-trifluoromethylphenyl)-2-(1H)-pyridone (2.159):

A solution of 4 g (16 mmol) of 3,4-dihydro-4-methyl-6-(3'-trifluoromethylphenyl)-2-(1H)-pyrone in 100 ml dichloromethane is treated with 5.6 ml of triethylamine and 7.31 g (70 mmol) of ethyl hydrazinoformate, and the mixture is refluxed for 8 hours. After cooling, the reaction solution is washed alternately with distilled $H_2O$, dilute HCl and distilled $H_2O$, dried over $Na_2SO_4$ and concentrated on a rotary evaporator. The oil which remains is taken up in 150 ml of toluene, the solution is treated with a spatula-tip full of PTSA and the mixture is refluxed on a water separator until the reaction is complete. For working-up, the reaction solution is washed first with dilute $K_2CO_3$ solution and then with distilled $H_2O$ and subsequently dried over $Na_2SO_4$. The oil obtained after the solvent has been evaporated in vacuo is purified by column chromatography on silica gel (eluent: toluene:acetone=95:5).

Yield: 3.1 g $^1$H NMR (300 MHz, $CDCl_3$) δ in ppm: 1.19 (s); 1.23 (s); 2.55 (m), 2.80 (m); 4.13 (m); 5.36 (m); 7.20 (m); 7.24 (m); 7.53 (m); 7.59 (m).

Example 3

1-(Ethoxycarbonyl)amino-4-methyl-6-(3'-trifluoromethylphenyl)-2-(1H)-pyridone (1.159):

A solution of 2.6 g (8 mmol) of 1-(ethoxycarbonyl)amino-3,4-dihydro-4-methyl-6-(3'-trifluoromethylphenyl)-2-(1H)-pyridone in 75 ml of toluene is treated with 2.3 g (10 mmol) of DDQ and the mixture is refluxed for 6 hours. After cooling, the reaction solution is filtered off by suction through Alox n and the filtrated is evaporated on a rotary evaporator. The oil which remains is purified by column chromatography on Alox n (eluent: ethyl acetate:methanol= 95:5).

Yield: 1.4 g

M.p.: 106–109° C.

The compounds I or the herbicidal compositions comprising them and their environmentally compatible salts of, for example, alkali metals, alkaline earth metals or ammonia and amines, or the herbicidal compositions comprising them in this form, can effect a very good control of broad-leaf weeds and grass weeds in crops such as wheat, rice, maize, soya bean and cotton without inflicting damage to the crop plants, an effect which above all is even present when low rates are applied.

Taking into consideration the various application methods, the compounds I, or compositions comprising them, can also be employed in a further number of crop plants for eliminating undesirable plants. Examples of suitable crops are the following:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays.*

In addition, the compounds I can also be used in crops which have been made tolerant against the action of herbicides by means of breeding, including genetic engineering methods.

The herbicidal compositions, or the active ingredients, can be applied pre- or post-emergence. If the active ingredients are less well tolerated by certain crop plants, application techniques may be used in which the herbicidal compositions are sprayed, with the aid of the spraying equipment, in such a way that the leaves of the sensitive crop plants come into as little contact with the active ingredients as possible while the active ingredients reach the leaves of undesirable plants which grow under them, or the naked soil surface (post-directed, lay-by).

The compounds I, or the herbicidal compositions comprising them, can be applied by spraying, atomizing, dusting, spreading or pouring, for example in the form of directly sprayable aqueous solutions, powders, suspensions, also high-percentage aqueous, oily or other suspensions or dispersions, emulsions, oil dispersions, pastes, dusts, materials for spreading, or granules. The use forms depend on the intended purpose; in any case, they should guarantee the finest possible distribution of the active ingredients according to the invention.

Suitable inert additives are mineral oil fractions of medium to high boiling point, such as kerosene or diesel oil, furthermore coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of a wetting agent, tackifier, dispersant or emulsifier. Alternatively, it is possible to prepare concentrates composed of active ingredient, wetting agent, tackifier, dispersant or emulsifier and, if desired, solvent or oil, and these concentrates are suitable for dilution with water.

Suitable surfactants are the alkali metal, alkaline earth metal and ammonium salts of aromatic sulfonic acids, eg. lignosulfonic acid, phenolsulfonic acid, naphthalenesulfonic acid and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensation products of sulfonated naphthalene and its derivatives with formaldehyde, condensation products of naphthalene, or naphthalenesulfonic acids, with phenyl and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, material for spreading, and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal, nutshell meal, cellulose powder, or other solid carriers.

In general, the formulations comprise from 0.01 to 95% by weight, preferably from 0.5 to 90% by weight, of active ingredient. The active ingredients are employed in a purity from 90% to 100%, preferably 95% to 100% (according to NMR spectrum).

The compounds I according to the invention can be formulated for example as follows:

I 20 parts by weight of compound No. 1.159 are dissolved in a mixture composed of 80 parts by weight of alkylated benzene, 10 parts by weight of the adduct of 8 to 10 mol of ethylene oxide to 1 mol of the oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

II 20 parts by weight of compound No. 1.159 are dissolved in a mixture composed of 40 parts by weight of cyclohexanone, 30 parts by weight of isobutanol, 20 parts by weight of the adduct of 7 mol of ethylene oxide to 1 mol of isooctylphenyl and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

III 20 parts by weight of the active ingredient No. 1.159 are dissolved in a mixture, composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqeous dispersion comprising 0.02% by weight of the active ingredient.

IV 20 parts by weight of the active ingredient No. 1.159 are mixed thoroughly with 3 parts by weight of sodium diisobutylnaphthalene-α-sulfonate, 17 parts by weight of sodium lignosulfonate from a sulfite waste liquor and 60 parts by weight of pulverulent silica gel and the mixture is ground in a hammer mill. Finely distributing the mixture in 20,000 parts by weight of water gives a spray mixture comprising 0.1% by weight of the active ingredient.

V 3 parts by weight of the active ingredient No. 1.159 are mixed with 97 parts by weight of finely divided kaolin. This gives a dust which comprises 3% by weight of the active ingredient.

VI 20 parts by weight of the active ingredient No. 1.159 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

To widen the spectrum of action and to achieve synergistic effects, the N-aminopyridone derivatives of the formula I may be mixed with a large number of representatives of other groups of herbicidal or growth-regulating active ingredients and then applied concomitantly. Suitable components for mixtures are, for example, diazines, 4H-1,3-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives having attached to them in the 2-position for example a carboxyl or carbimino group, or quinolinecarboxylic acid derivatives, imidazolinones, sulfonamides, sulfonylureas, aryloxy- or heteroaryloxyphenoxypropionic acids and their salts, esters and amides, and others.

It may furthermore be advantageous to apply the compounds I, alone or in combination with other herbicides, together with further crop protection agents, for example with pesticides or agents for controlling phytopathogenic fungi or bacteria. Also of interest is the miscibility with mineral salt solutions, which are employed for treating nutrient and trace element deficiencies. Non-phytotoxic oils and oil concentrates may also be added.

Depending on the intended aim, the season, the target plants and the growth stage, the application rates of active ingredient are from 0.001 to 3.0, preferably 0.01 to 1.0, kg of active ingredient (a.i.) per ha.

Use Examples

The herbicidal action of the N-aminopyridone derivatives of the formula I was demonstrated by greenhouse experiments:

The culture containers used were plastic flowerpots containing loamy sand with approximately 3.0% of humus as the substrate. The seeds of the test plants were sown separately for each species.

In the case of pre-emergence treatment, the active ingredients, which were suspended or emulsified in water, were applied directly after sowing by means of finely distributing nozzles. The containers were irrigated slightly to promote germination and growth and subsequently covered with translucent plastic hoods until the plants had rooted. This cover results in uniform germination of the test plants, unless germination was adversely affected by the active ingredients. The application rate for the pre-emergence treatment is 0.5 or 0.25 kg of a.i. per ha.

For the post-emergence treatment, the test plants were first grown to a plant height of from 3 to 15 cm, depending on the growth form, and only then treated with the active ingredients which were suspended or emulsified in water. To this end, the test plants were either sown directly or grown in the same containers, or grown separately as seedlings and transplanted to the test containers a few days prior to treatment. The application rate for the post-emergence treatment is 0.5 or 0.25 kg of a.i. per ha.

Depending on the species, the plants were kept at from 10–25° C. or 20–35° C. The test period extended from 2 to 4 weeks. During this time, the plants were tended, and their response to the individual treatments was evaluated.

A scale from 0 to 100 was used for the assessment. 100 means no plant emergence, or complete destruction of at least the aerial parts, and 0 means no damage, or normal course of growth.

The plants used in the greenhouse experiments comprise the following species:

| Latin Name | Common Name |
| --- | --- |
| *Echinochloa crus-galli* | Barnyard grass |
| *Setaria faberii* | Giant foxtail |
| *Setaria viridis* | Green foxtail |

TABLE 5

Post-emergence application: herbicidal activity under greenhouse conditions

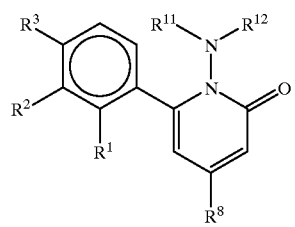

(Ex. No. 1.159: $R^1=R^3=H$, $R^2=CF_3$, $R^8=CH_3$, $R^{11}=COOC_2H_5$, $R^{12}=H$).

| Ex. No. 1.159 | | |
| --- | --- | --- |
| Application rate (kg of a.i. per ha | 0.5 | 0.25 |
| Test plants | Damage in % | |
| ECHCG | 90 | 80 |
| SETVI | 90 | 85 |
| SOLNI | 98 | 98 |

TABLE 6

Pre-emergence application: herbicidal activity under greenhouse conditions

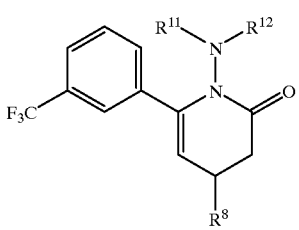

Ie (Ex. No. 1.159: $R^1=R^3=H$, $R^2=CF_3$, $R^8=CH_3$, $R^{11}=COOC_2H_5$, $R^{12}=H$).

| Ex. No. 1.159 | | |
| --- | --- | --- |
| Application rate (kg/ha a.S.) | 0.5 | 0.25 |
| Test plants | Damage in % | |
| ECHCG | 100 | 100 |
| SETFA | 95 | 95 |

TABLE 7

If

| Ex. No. | $R^8$ | $R^{11}$ | $R^{12}$ | $^1$H-NMR (300 MHz, CDCl$_3$) δ in ppm: | M.p. [° C.] |
| --- | --- | --- | --- | --- | --- |
| 2.187 | CH$_3$ | —CO—mCl—Ph | H | 1.27(3H); 1.43(1H); 3.06(2H); 5.48(1H); 7.15–7.82(8H); 10.28(1H). | — |
| 2.158 | CH$_3$ | —COOCH$_3$ | H | 1.11(3H); 2.58(1H); 2.79(2H); 3.72(3H); 5.35(1H); 6.75(1H); 7.40–7.59(4H). | — |
| 2.161 | CH$_3$ | —COO$^t$Bu | H | 1.12(3H); 1.42(9H); 2.55(1H); 2.78(2H); 5.29(1H); 6.49(1H); 7.11–7.56(4H). | — |
| 2.170 | CH$_3$ | —COCH$_2$CN | H | 1.23(3H); 2.58(1H); 2.79(2H); 3.25(2H); 5.42(1H); 7.41–7.62(4H); 8.52(1H). | — |
| 2.159 | CH$_3$ | —COOC$_2$H$_5$ | H | 1.08(3H); 1.12(3H); 2.55(1H); 2.80(2H); 4.13(2H); 5.36(1H); 6.80(1H); 7.20–7.59(4H). | — |
| 2.173 | CH$_3$ | —CH$_2$—COOC$_2$H$_5$ | H | 1.08(3H); 1.12(3H); 2.44(1H); 2.72(2H); 3.41(2H); 4.12(2H); 5.31(1H); 5.55(1H); 7.46–7.62(4H). | — |

TABLE 7-continued

Structure If: 6-(3-(trifluoromethyl)phenyl)-1-(NR¹¹R¹²)-4-R⁸-3,4-dihydropyridin-2(1H)-one

| Ex. No. | R⁸ | R¹¹ | R¹² | ¹H-NMR (300 MHz, CDCl₃) δ in ppm: | M.p. [° C.] |
|---|---|---|---|---|---|
| 2.601 | CH₃ | —COⁿC₄H₉ | H | 0.7(3H); 0.9(2H); 1.3(5H); 2.0(2H; 2.8(3H); 5.4(1H); 7.5(3H); 7.6(1H); 8.2(1H) | — |
| 2.186 | CH₃ | —COPh | H |  | 78–85 |
| 2.602 | CH₃ | —CO-3,4-Cl₂Ph | H | 1.3(3H); 2.8(3H); 5.5(1H); 7.2(2H); 7.5(4H); 7.7(1H); 10.0(1H) | — |
| 2.603 | CH₃ | —CO-4-CH₃Ph | H | — | 60–65 |
| 2.604 | CH₃ | —CO-4-FPh | H | — | 60–65 |

TABLE 8

Structure Ig: 6-(3-(trifluoromethyl)phenyl)-1-(NR¹¹R¹²)-4-R⁸-pyridin-2(1H)-one

| Ex. No. | R⁸ | R¹¹ | R¹² | M.p. [° C.] |
|---|---|---|---|---|
| 1.187 | CH₃ | —CO-mCl-Ph | H | 215 |
| 1.158 | CH₃ | —COOCH₃ | H | 164–165 |
| 1.161 | CH₃ | —COOᵗBu | H | 146–148 |
| 1.159 | CH₃ | —COOC₂H₅ | H | 121–122 |
| 1.152 | CH₃ | H | H | 136–138 |
| 1.601 | CH₃ | —COO-cyclohexyl | H | 181–186 |
| 1.602 | CH₃ | —COOCH₂CCl₃ | H | 157–161 |
| 1.603 | CH₃ | —COOCH₂CH(CH₃)₂ | H | 148–150 |
| 1.604 | CH₃ | —COOCH₂CHCH₂ | H | 114–117 |
| 1.605 | CH₃ | —COOⁿBu | H | 152–153 |
| 1.606 | CH₃ | —COOCH₂Ph | H | 192–193 |
| 1.607 | CH₃ | —COO-C(=CH₂)CH₃ | H | 130–131 |

TABLE 9

Structure Id: 6-(2-R¹-3-R²-4-R³-phenyl)-1-(NR¹¹R¹²)-4-R⁸-3,4-dihydropyridin-2(1H)-one

| No. | R¹ | R² | R³ | R⁸ | R¹¹ | R¹² | ¹H-NMR (300 MHz, CDCl₃) δ in ppm: |
|---|---|---|---|---|---|---|---|
| 2.605 | H | —OC₂F₄H | H | CH₃ | —COOCH₃ | H | 1.17(3H), 2.56(1H); 2.76(2H); 3.65(3H); 5.35(1H); 5.92(1H); 6.79(1H); 7.13–7.28(4H). |
| 2.606 | H | —OC₂F₄H | H | CH₃ | —COOC₂H₅ | H | 1.16(3H); 1.28(3H), 2.55(1H); 2.74(2H), 4.10(2H); 5.32(1H); 5.91(1H); 6.70(1H); 7.13–7.40(4H). |
| 2.607 | H | —OC₂F₄H | H | CH₃ | —COOᵗBu | H | 1.18(3H); 1.36(9H); 2.49(1H); 2.72(2H); 5.27(1H); 5.88(1H); 6.59(1H); 7.09–7.36(4H). |

TABLE 10

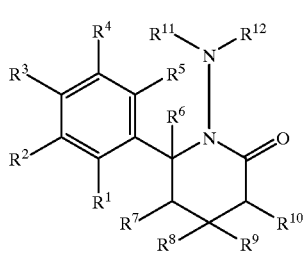

| No. | R¹ | R² | R³ | R⁸ | R¹¹ | R¹² | ¹H-NMR (300 MHz, CDCl₃) δ in ppm: |
|---|---|---|---|---|---|---|---|
| 1.608 | H | —OC₂F₄H | H | CH₃ | —COOCH₃ | H | 2.13(3H); 3.61(3H); 5.97(1H); 6.09(1H); 6.44(1H); 7.22–7.43(4H); 8.72(1H). |
| 1.609 | H | —OC₂F₄H | H | CH₃ | —COOC₂H₅ | H | 1.17(3H); 2.23(3H); 4.11(2H); 5.94(1H); 6.08(1H); 6.46(1H); 7.25–7.43(4H); 8.24(1H). |
| 1.610 | H | —OC₂F₄H | H | CH₃ | —COOᵗBu | H | 1.30(9H); 2.26(3H); 5.89(1H); 6.10(1H); 6.57(1H); 7.21–7.44(4H). |

TABLE 11

Ih

| Ex. No. | R⁸ | R¹¹ | R¹² | M.p. [° C.] |
|---|---|---|---|---|
| 1.2 | CH₃ | H | H | 147–148 |
| 1.611 | CH₃ | —COOCH₂CH(CH₃)₂ | H | 154–156 |

We claim:

1. An N-aminopyridone derivative of the formula I:

I where the substituents have the following meanings:
R¹–R⁵ are identical or different substituents selected from the group consisting of hydrogen, CN, halogen, OR¹⁵, C₁–C₄-alkyl, C₁–C₄-alkoxy, wherein the alkyl moieties are linear or branched and to have attached to them in each case one to five halogen atoms;
or two adjacent radicals of R¹ to R⁵ are part of a cyclic acetal having five ring members, wherein a ring carbon atom is optionally substituted by one to two halogen atoms;

Z is a bond;

R⁶ and R⁷ are in each case hydrogen or together form a bond;

R⁹ and R¹⁰ are in each case hydrogen or together form a bond;

R⁸ is hydrogen, C₁–C₄-alkyl;

R¹¹ is hydrogen, C₁–C₄-alkyl, wherein alkyl moieties are linear or branched;

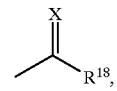

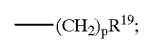

R¹² is hydrogen or C₁–C₄-alkyl;

X is O;

R¹⁷ is hydrogen, C₁–C₄-alkoxy, C₁–C₄-alkyl, or branched wherein the alkyl moieties are linear;

R¹⁶ is hydrogen, C₁–C₈-alkyl, C₁–C₆-alkoxy or C₃–C₆-cycloalkoxy wherein the alkyl moieties are linear or branched and to have attached to them in each case one to five halogen atoms and/or one to two of the following groups: cyano, phenyl;
phenyl optionally substituted by one to five of the following substituents: halogen, C₁–C₄-alkyl, it being possible for the alkyl radicals to be unbranched or branched;

R¹⁹ is ZCOR¹⁷;

p=1 to 4.

2. An N-aminopyridone derivative of the formula Id

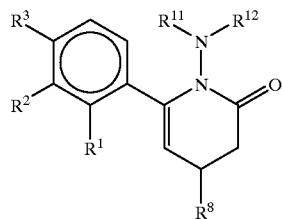

where the substituents $R^1$, $R^2$, $R^3$, $R^8$, $R^{11}$ and $R^{12}$ have the meanings given in claim 1.

3. N-Aminopyridone derivatives of the formula Ie

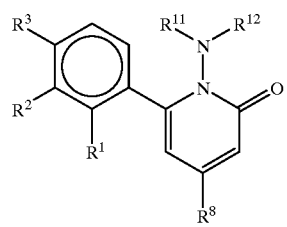

where the substituents $R^1$, $R^2$, $R^3$, $R^8$, $R^{11}$ and $R^{12}$ have the meanings given in claim 1.

4. An N-aminopyridone derivative of the formula If

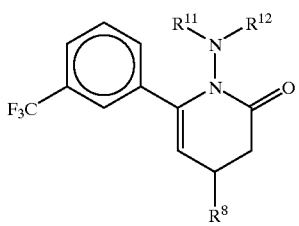

where the substituents $R^8$, $R^{11}$ and $R^{12}$ have the meanings given in claim 1.

5. An N-aminopyridone derivative of the formula Ig

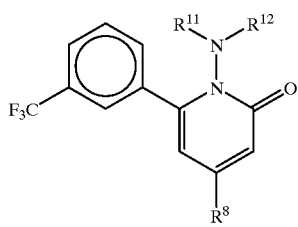

where the substsituents $R^8$, $R^{11}$ and $R^{12}$ have the meanings given in claim 1.

6. An N-aminopyridone derivative of the formula Ij

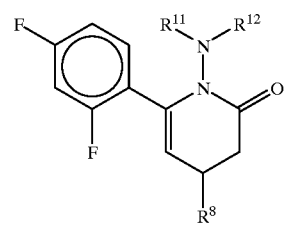

where the substituents $R^8$, $R^{11}$ and $R^{12}$ have the meanings given in claim 1.

7. An N-aminopyridone derivative of the formula Ik

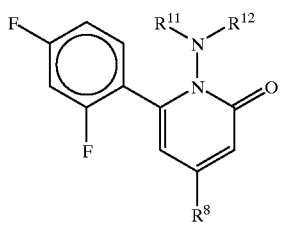

where the substituents $R^8$, $R^{11}$ and $R^{12}$ have the meaenings given in claim 1.

8. An N-aminopyridine derivative of the formula Il

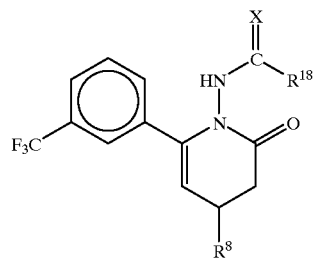

where the substituents $R^{8, X \text{ and } R^{18}}$ have the meaning given in claim 1.

9. An N-aminopyridone derivative of the formula Im

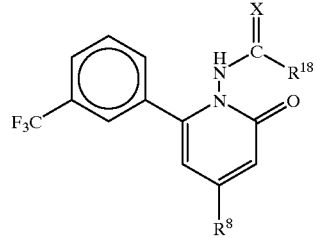

where the substituents $R^8$, X and $R^{18}$ have the meanings given in claim 1.

10. A herbicidal composition comprising a N-aminopyridone derivative as claimed in claim 1 and inert additives.

11. A method of controlling undesirable vegetation, which comprises applying a herbicidally active amount of an N-aminopyridone derivative as claimed in claim 1 to the plants or their environment.

12. A process for the preparation of N-aminodihydropyridones of the formula Ia where the radicals $R^1$ to $R^5$, $R^8$, $R^{11}$ and $R^{12}$ have the meanings given in claim 1, which comprises reacting dihydropyrones of the structure II with hydrazine/hydrazide hydrochlorides in the presence of an auxiliary base, such as tert-alkylamine or pyridine, and subsequently condensing the product with p-toluenesulfonic acid (PTSA) in toluene under reflux benzenes XI and subsequently reacting the product with 3-substituted glutaric anhydrides XII to give 3-substituted 5-phenyl-5-ketocarboxylic acids III and finally subjecting the latter to ring closure to give the dihydropyrones II

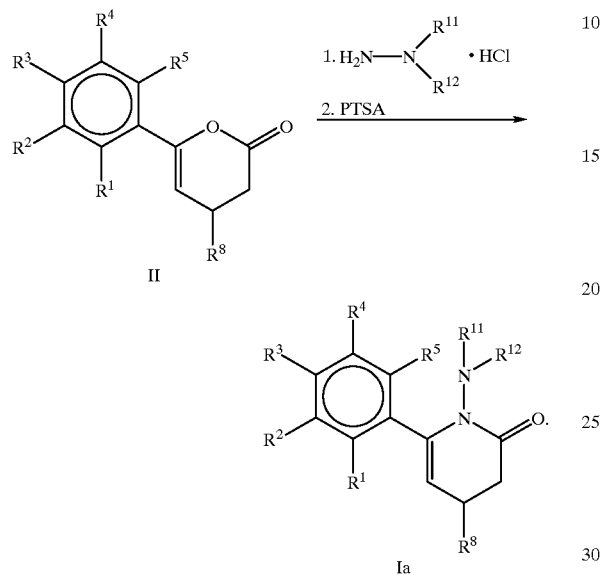

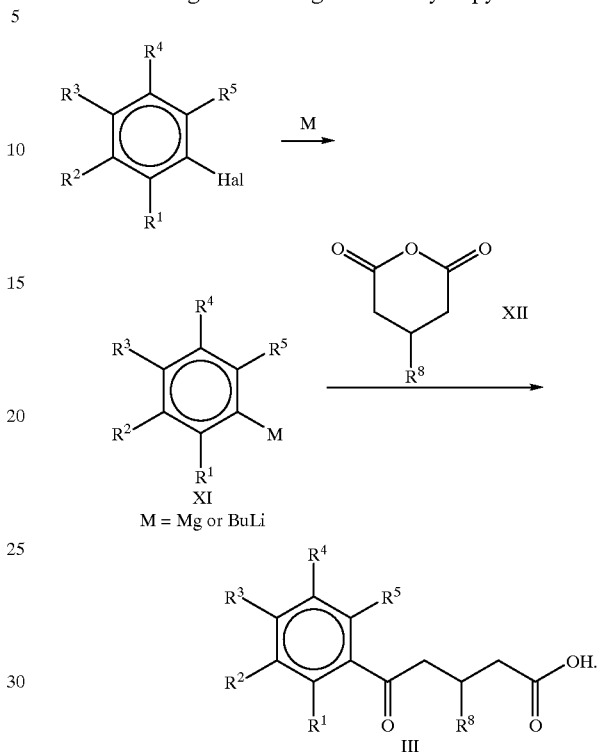

13. A process as defined in claim 17, wherein the dihydropyrones of the formula II are prepared by converting substituted halobenzenes with magnesium or butyllithium in ether or THF as the solvent into metallated substituted

* * * * *

UNITED STATES PATENT AND TRADEMARK OFFICE
CERTIFICATE OF CORRECTION

PATENT NO.: 6,028,033

DATED: February 22, 2000

INVENTOR(S): HILL et al.

It is certified that error appears in the above-identified patent and that said Letters Patent is hereby corrected as shown below:

Column 66, claim 8, line 44, delete "X and R18" and insert --,X and $R^{18}$--.

Column 67, claim 13, line 34, delete "claim 17" insert --claim 12 --.

Signed and Sealed this

Twenty-sixth Day of December, 2000

Attest:

Q. TODD DICKINSON

*Attesting Officer*   *Director of Patents and Trademarks*